US008771989B2

(12) United States Patent
Choi

(10) Patent No.: US 8,771,989 B2
(45) Date of Patent: Jul. 8, 2014

(54) VECTORS AND YEAST STRAINS FOR PROTEIN PRODUCTION: CA2+ ATPASE OVEREXPRESSION

(71) Applicant: GlycoFi, Inc., Lebanon, NH (US)

(72) Inventor: Byung-Kwon Choi, Norwich, VT (US)

(73) Assignee: GlycoFi, Inc., Lebanon, NH (US)

( * ) Notice: Subject to any disclaimer, the term of this patent is extended or adjusted under 35 U.S.C. 154(b) by 0 days.

(21) Appl. No.: 13/938,603

(22) Filed: Jul. 10, 2013

(65) Prior Publication Data

US 2013/0316403 A1 Nov. 28, 2013

Related U.S. Application Data

(62) Division of application No. 13/057,807, filed as application No. PCT/US2009/053247 on Aug. 10, 2009, now Pat. No. 8,507,224.

(60) Provisional application No. 61/188,761, filed on Aug. 12, 2008.

(51) Int. Cl.
*C07K 16/00* (2006.01)
*C12P 21/00* (2006.01)
*C12N 1/15* (2006.01)
*C12N 1/19* (2006.01)
*C12N 15/81* (2006.01)

(52) U.S. Cl.
CPC .............. *C07K 16/00* (2013.01); *C12N 15/815* (2013.01); *C12P 21/005* (2013.01)
USPC ................... 435/69.6; 435/69.1; 435/254.21; 435/254; 435/22

(58) Field of Classification Search
None
See application file for complete search history.

(56) References Cited

U.S. PATENT DOCUMENTS

| | | | |
|---|---|---|---|
| 4,818,700 | A | 4/1989 | Cregg et al. |
| 5,268,364 | A | 12/1993 | Kojima et al. |
| 5,714,377 | A | 2/1998 | Tanner et al. |
| 6,103,501 | A | 8/2000 | Boime et al. |
| 7,029,872 | B2 | 4/2006 | Gerngross |
| 7,105,554 | B2 | 9/2006 | Orchard et al. |
| 7,198,921 | B2 | 4/2007 | Miura et al. |
| 7,259,007 | B2 | 8/2007 | Bobrowicz et al. |
| 7,479,389 | B2 | 1/2009 | Nett et al. |
| 2002/0068325 | A1 | 6/2002 | Ng et al. |
| 2002/0128235 | A1 | 9/2002 | Konrad et al. |
| 2002/0160408 | A1 | 10/2002 | Pelletier et al. |
| 2003/0186850 | A1 | 10/2003 | Clausen et al. |
| 2004/0018590 | A1 | 1/2004 | Gerngross et al. |
| 2004/0074458 | A1 | 4/2004 | Nakamura et al. |
| 2004/0229306 | A1 | 11/2004 | Nett |
| 2004/0230042 | A1 | 11/2004 | Hamilton |
| 2005/0170452 | A1 | 8/2005 | Wildt et al. |
| 2005/0260729 | A1 | 11/2005 | Hamilton |
| 2006/0040353 | A1 | 2/2006 | Davidson et al. |
| 2006/0211085 | A1 | 9/2006 | Bobrowicz |
| 2006/0286637 | A1 | 12/2006 | Hamilton |
| 2007/0037248 | A1 | 2/2007 | Bobrowicz et al. |
| 2007/0072262 | A1 | 3/2007 | Nett et al. |
| 2011/0312032 | A1 | 12/2011 | Choi |

FOREIGN PATENT DOCUMENTS

| | | |
|---|---|---|
| WO | 94/04687 | 3/1994 |
| WO | 2007/061631 | 5/2007 |
| WO | 2007/136865 | 11/2007 |
| WO | 2009/085135 | 7/2009 |

OTHER PUBLICATIONS

Lin Cereghino, "New selectable marker/auxotrophic host strain combinations . . . ", Gene (2001), vol. 263, pp. 159-169.
Bobrowicz, "Isolation of three contiguous genes . . . ", Yeast (1997), vol. 13, pp. 819-828.
Borrebaeck, "Does endogenous glycosylation prevent the use . . . ", Immunol. Today (1993), vol. 14, pp. 477-479.
Cabanes-Macheteau, "N-Glycosylation of a mouse IgG expressed . . . ", Glycobiology (1999), vol. 9, pp. 365-372.
Choi, "Use of combinatorial genetic libraries to humanize . . . ", PNAS (2003), vol. 100, pp. 5022-5027.
Cigan, "Sequence and structural features associated with translational . . . ", Gene (1987), vol. 59, pp. 1-18.
Cosano, "Cloning and sequence analysis of the *Pichia pastoris* . . . ", Yeast (1998), vol. 14, pp. 861-867.
Hamilton, "Production of complex human glycoproteins . . . ", Science (2003), vol. 301, pp. 1244-1246.
Harvey, "Matrix-assisted laser desorption/ionization . . . ", Mass Spectrometry Rev. (1999), vol. 18, pp. 349-451.
Li, "Optimization of humanized IgGs in glycoengineered . . . ", Nature Biotech. (2006), vol. 24, pp. 210-215.
Lis, "Protein glycosylation", Eur. J. Biochem. (1993), vol. 218, pp. 1-27.
Wysocki, "The *Saccharomyces cerevisiae* ACR3 gene . . . ", J. Biol. Chem. (1997), vol. 272, pp. 30061-30066.
Wilson, Amino acid distributions around O-linked . . . , Biochem. J. (1991), vol. 275, pp. 529-534.
Varki, "Biological roles of oligosaccharides . . . ", Glycobiology (1993), vol. 3, pp. 97-130.
Van Den Steen, "Concepts and principles of O-linked . . . ", Critical Rev. in Biochem. & Molec. Biol., (1998), vol. 33, pp. 151-208.
Nett, "Cloning and disruption of the PpURA5 gene . . . ", Yeast (2003), vol. 20, pp. 1279-1290.
Mille, "Identification of a new family of genes . . . ", J. Biol. Chem. (2008), vol. 283, pp. 9724-9736.
Kaufman, "Depletion of manganese within the secretory pathway . . . ", Biochemistry (1994), vol. 33, pp. 9813-9819.
Bates, "*Candida albicans* Pmr1p, a secretory pathway . . . ", J. Biol. Chem. (2005), vol. 280, pp. 23408-23415.
Durr, "The medial-Golgi ion pump Pmr1 supplies the yeast . . . ", Molecular Biology of the Cell (1998), vol. 9, pp. 1149-1162.
GenBank Accession No. X56180, "*P. pastoris* HIS4 gene for trifunctional enzyme . . . ", Apr. 18, 2005.

*Primary Examiner* — Kagnew H Gebreyesus
(74) *Attorney, Agent, or Firm* — Immac J. Thampoe; John David Reilly

(57) ABSTRACT

Lower eukaryote host cells in which an endogenous or heterologous $Ca^{2+}$ ATPase is overexpressed are described. Also described are lower eukaryote host cells in which a calreticulin and/or ERp57 protein are overexpressed. These host cells are useful for producing recombinant glycoproteins that have reduced O-glycosylation.

7 Claims, 12 Drawing Sheets

Genealogy of Chaperone-humanized Strains

SEQUENCE LISTING

<160> NUMBER OF SEQ ID NOS: 50

<210> SEQ ID NO 1
<211> LENGTH: 30
<212> TYPE: DNA
<213> ORGANISM: Artificial Sequence
<220> FEATURE:
<223> OTHER INFORMATION: PCR primer hPDI/UP1

<400> SEQUENCE: 1
agcgctgacg cccccgagga ggaggaccac        30

<210> SEQ ID NO 2
<211> LENGTH: 42
<212> TYPE: DNA
<213> ORGANISM: Artificial Sequence
<220> FEATURE:
<223> OTHER INFORMATION: PCR primer hPDI/LP-PacI

<400> SEQUENCE: 2
ccttaattaa ttacagttca tcatgcacag ctttctgatc at        42

<210> SEQ ID NO 3
<211> LENGTH: 47
<212> TYPE: DNA
<213> ORGANISM: Artificial Sequence
<220> FEATURE:
<223> OTHER INFORMATION: PCR primer PB248

<400> SEQUENCE: 3
atgaattcag gccatatcgg ccattgttta ctgtgcgccc acagtag        47

<210> SEQ ID NO 4
<211> LENGTH: 35
<212> TYPE: DNA
<213> ORGANISM: Artificial Sequence
<220> FEATURE:
<223> OTHER INFORMATION: PCR primer PB249

<400> SEQUENCE: 4
atgtttaaac gtgaggatta ctggtgatga aagac        35

<210> SEQ ID NO 5
<211> LENGTH: 34
<212> TYPE: DNA
<213> ORGANISM: Artificial Sequence
<220> FEATURE:
<223> OTHER INFORMATION: PCR primer PB250

<400> SEQUENCE: 5
agactagtct atttggagac attgacggat ccac        34

<210> SEQ ID NO 6
<211> LENGTH: 46
<212> TYPE: DNA
<213> ORGANISM: Artificial Sequence
<220> FEATURE:
<223> OTHER INFORMATION: PCR primer PB251

<400> SEQUENCE: 6
atctcgagag gccatgcagg ccaaccacaa gatgaatcaa attttg        46

<210> SEQ ID NO 7
<211> LENGTH: 34
<212> TYPE: DNA
<213> ORGANISM: Artificial Sequence

```
<220> FEATURE:
<223> OTHER INFORMATION: PCR primer PpPDI/UPi-1

<400> SEQUENCE: 7
ggtgaggttg aggtcccaag tgactatcaa ggtc                                    34

<210> SEQ ID NO 8
<211> LENGTH: 34
<212> TYPE: DNA
<213> ORGANISM: Artificial Sequence
<220> FEATURE:
<223> OTHER INFORMATION: PCR primer PpPDI/LPi-1

<400> SEQUENCE: 8
gaccttgata gtcacttggg acctcaacct cacc                                    34

<210> SEQ ID NO 9
<211> LENGTH: 34
<212> TYPE: DNA
<213> ORGANISM: Artificial Sequence
<220> FEATURE:
<223> OTHER INFORMATION: PCR primer PpPDI/UPi-2

<400> SEQUENCE: 9
cgccaatgat gaggatgcct cttcaaaggt tgtg                                    34

<210> SEQ ID NO 10
<211> LENGTH: 34
<212> TYPE: DNA
<213> ORGANISM: Artificial Sequence
<220> FEATURE:
<223> OTHER INFORMATION: PCR primer PpPDI/LPi-2

<400> SEQUENCE: 10
cacaaccttt gaagaggcat cctcatcatt ggcg                                    34

<210> SEQ ID NO 11
<211> LENGTH: 24
<212> TYPE: DNA
<213> ORGANISM: Artificial Sequence
<220> FEATURE:
<223> OTHER INFORMATION: PCR primer PpPDI-5'/UP

<400> SEQUENCE: 11
ggcgattgca ttcgcgactg tatc                                               24

<210> SEQ ID NO 12
<211> LENGTH: 23
<212> TYPE: DNA
<213> ORGANISM: Artificial Sequence
<220> FEATURE:
<223> OTHER INFORMATION: PCR primer hPDI-3'/LP

<400> SEQUENCE: 12
cctagagagc ggtggccaag atg                                                23

<210> SEQ ID NO 13
<211> LENGTH: 25
<212> TYPE: DNA
<213> ORGANISM: Artificial Sequence
<220> FEATURE:
<223> OTHER INFORMATION: PCR primer hPDI/UP

<400> SEQUENCE: 13
gtggccacac caggggggcat ggaac                                             25
```

```
<210> SEQ ID NO 14
<211> LENGTH: 23
<212> TYPE: DNA
<213> ORGANISM: Artificial Sequence
<220> FEATURE:
<223> OTHER INFORMATION: PCR primer hPDI-3'/LP

<400> SEQUENCE: 14
cctagagagc ggtggccaag atg                                          23

<210> SEQ ID NO 15
<211> LENGTH: 37
<212> TYPE: DNA
<213> ORGANISM: Artificial Sequence
<220> FEATURE:
<223> OTHER INFORMATION: PCR primer hGRP94/UP1

<400> SEQUENCE: 15
agcgctgacg atgaagttga tgtggatggt acagtag                           37

<210> SEQ ID NO 16
<211> LENGTH: 38
<212> TYPE: DNA
<213> ORGANISM: Artificial Sequence
<220> FEATURE:
<223> OTHER INFORMATION: PCR primer hGRP94/LP1

<400> SEQUENCE: 16
ggccggcctt acaattcatc atgttcagct gtagattc                          38

<210> SEQ ID NO 17
<211> LENGTH: 57
<212> TYPE: DNA
<213> ORGANISM: Artificial Sequence
<220> FEATURE:
<223> OTHER INFORMATION: Saccharomyces cerevisiae mating factor
      pre-signal peptide

<400> SEQUENCE: 17
atgagattcc catccatctt cactgctgtt ttgttcgctg cttcttctgc tttggct     57

<210> SEQ ID NO 18
<211> LENGTH: 19
<212> TYPE: PRT
<213> ORGANISM: Artificial Sequence
<220> FEATURE:
<223> OTHER INFORMATION: Saccharomyces cerevisiae mating factor
      pre-signal peptide

<400> SEQUENCE: 18

Met Arg Phe Pro Ser Ile Phe Thr Ala Val Leu Phe Ala Ala Ser Ser
1               5                   10                  15

Ala Leu Ala

<210> SEQ ID NO 19
<211> LENGTH: 1476
<212> TYPE: DNA
<213> ORGANISM: Artificial Sequence
<220> FEATURE:
<223> OTHER INFORMATION: human PDI without leader

<400> SEQUENCE: 19
gacgcccccg aggaggagga ccacgtcttg gtgctgcgga aaagcaactt cgcggaggcg    60
ctggcggccc acaagtaccc gccggtggag ttccatgccc cctggtgtgg ccactgcaag   120
```

| | | |
|---|---|---|
| gctctggccc ctgagtatgc caaagccgct gggaagctga aggcagaagg ttccgagatc | 180 |
| aggttggcca aggtggacgc cacggaggag tctgacctag cccagcagta cggcgtgcgc | 240 |
| ggctatccca ccatcaagtt cttcaggaat ggagacacgg cttcccccaa ggaatataca | 300 |
| gctggcagag aggctgatga catcgtgaac tggctgaaga gcgcacggg cccggctgcc | 360 |
| accaccctgc ctgacggcgc agctgcagag tccttggtgg agtccagcga ggtggccgtc | 420 |
| atcggcttct tcaaggacgt ggagtcggac tctgccaagc agttttttgca ggcagcagag | 480 |
| gccatcgatg acataccatt tgggatcact tccaacagtg acgtgttctc caaataccag | 540 |
| ctcgacaaag atggggttgt cctctttaag aagtttgatg aaggccggaa caactttgaa | 600 |
| ggggaggtca ccaaggagaa cctgctggac tttatcaaac acaaccagct gcccttgtc | 660 |
| atcgagttca ccgagcagac agccccgaag atttttggag gtgaaatcaa gactcacatc | 720 |
| ctgctgttct tgcccaagag tgtgtctgac tatgacggca aactgagcaa cttcaaaaca | 780 |
| gcagccgaga gcttcaaggg caagatcctg ttcatcttca tcgacagcga ccacaccgac | 840 |
| aaccagcgca tcctcgagtt cttttggcctg aagaaggaag agtgcccggc cgtgcgcctc | 900 |
| atcaccttgg aggaggagat gaccaagtac aagcccgaat cggaggagct gacggcagag | 960 |
| aggatcacag agttctgcca ccgcttcctg gagggcaaaa tcaagcccca cctgatgagc | 1020 |
| caggagctgc cggaggactg ggacaagcag cctgtcaagg tgcttgttgg gaagaacttt | 1080 |
| gaagacgtgg cttttgatga aaaaaaaaac gtctttgtgg agttctatgc ccatggtgt | 1140 |
| ggtcactgca acagttggc tcccatttgg gataaactgg agagacgta caaggaccat | 1200 |
| gagaacatcg tcatcgccaa gatggactcg actgccaacg aggtggaggc cgtcaaagtg | 1260 |
| cacggcttcc ccacactcgg gttctttcct gccagtgccg acaggacggt cattgattac | 1320 |
| aacggggaac gcacgctgga tggttttaag aaattcctag agagcggtgg ccaagatggg | 1380 |
| gcaggggatg ttgacgacct cgaggacctc gaagaagcag aggagccaga catggaggaa | 1440 |
| gacgatgacc agaaagctgt gaaagatgaa ctgtaa | 1476 |

<210> SEQ ID NO 20
<211> LENGTH: 491
<212> TYPE: PRT
<213> ORGANISM: Artificial Sequence
<220> FEATURE:
<223> OTHER INFORMATION: human PDI without leader

<400> SEQUENCE: 20

Asp Ala Pro Glu Glu Asp His Val Leu Val Leu Arg Lys Ser Asn
1               5                   10                  15

Phe Ala Glu Ala Leu Ala Ala His Lys Tyr Pro Pro Val Glu Phe His
            20                  25                  30

Ala Pro Trp Cys Gly His Cys Lys Ala Leu Ala Pro Glu Tyr Ala Lys
        35                  40                  45

Ala Ala Gly Lys Leu Lys Ala Glu Gly Ser Glu Ile Arg Leu Ala Lys
    50                  55                  60

Val Asp Ala Thr Glu Glu Ser Asp Leu Ala Gln Gln Tyr Gly Val Arg
65                  70                  75                  80

Gly Tyr Pro Thr Ile Lys Phe Phe Arg Asn Gly Asp Thr Ala Ser Pro
                85                  90                  95

Lys Glu Tyr Thr Ala Gly Arg Glu Ala Asp Asp Ile Val Asn Trp Leu
            100                 105                 110

Lys Lys Arg Thr Gly Pro Ala Ala Thr Thr Leu Pro Asp Gly Ala Ala
        115                 120                 125

Ala Glu Ser Leu Val Glu Ser Glu Val Ala Val Ile Gly Phe Phe
130                 135                 140

Lys Asp Val Glu Ser Asp Ser Ala Lys Gln Phe Leu Gln Ala Ala Glu
145                 150                 155                 160

Ala Ile Asp Asp Ile Pro Phe Gly Ile Thr Ser Asn Ser Asp Val Phe
                165                 170                 175

Ser Lys Tyr Gln Leu Asp Lys Asp Gly Val Val Leu Phe Lys Lys Phe
            180                 185                 190

Asp Glu Gly Arg Asn Asn Phe Glu Gly Glu Val Thr Lys Glu Asn Leu
        195                 200                 205

Leu Asp Phe Ile Lys His Asn Gln Leu Pro Leu Val Ile Glu Phe Thr
210                 215                 220

Glu Gln Thr Ala Pro Lys Ile Phe Gly Gly Glu Ile Lys Thr His Ile
225                 230                 235                 240

Leu Leu Phe Leu Pro Lys Ser Val Ser Asp Tyr Asp Gly Lys Leu Ser
                245                 250                 255

Asn Phe Lys Thr Ala Ala Glu Ser Phe Lys Gly Lys Ile Leu Phe Ile
            260                 265                 270

Phe Ile Asp Ser Asp His Thr Asp Asn Gln Arg Ile Leu Glu Phe Phe
        275                 280                 285

Gly Leu Lys Lys Glu Glu Cys Pro Ala Val Arg Leu Ile Thr Leu Glu
290                 295                 300

Glu Glu Met Thr Lys Tyr Lys Pro Glu Ser Glu Leu Thr Ala Glu
305                 310                 315                 320

Arg Ile Thr Glu Phe Cys His Arg Phe Leu Gly Lys Ile Lys Pro
                325                 330                 335

His Leu Met Ser Gln Glu Leu Pro Glu Asp Trp Asp Lys Gln Pro Val
            340                 345                 350

Lys Val Leu Val Gly Lys Asn Phe Glu Asp Val Ala Phe Asp Glu Lys
        355                 360                 365

Lys Asn Val Phe Val Glu Phe Tyr Ala Pro Trp Cys Gly His Cys Lys
370                 375                 380

Gln Leu Ala Pro Ile Trp Asp Lys Leu Gly Glu Thr Tyr Lys Asp His
385                 390                 395                 400

Glu Asn Ile Val Ile Ala Lys Met Asp Ser Thr Ala Asn Glu Val Glu
                405                 410                 415

Ala Val Lys Val His Gly Phe Pro Thr Leu Gly Phe Phe Pro Ala Ser
            420                 425                 430

Ala Asp Arg Thr Val Ile Asp Tyr Asn Gly Glu Arg Thr Leu Asp Gly
        435                 440                 445

Phe Lys Lys Phe Leu Glu Ser Gly Gly Gln Asp Gly Ala Gly Asp Val
450                 455                 460

Asp Asp Leu Glu Asp Leu Glu Glu Ala Glu Glu Pro Asp Met Glu Glu
465                 470                 475                 480

Asp Asp Asp Gln Lys Ala Val His Asp Glu Leu
                485                 490

<210> SEQ ID NO 21
<211> LENGTH: 1554
<212> TYPE: DNA
<213> ORGANISM: Pichia pastoris
<220> FEATURE:
<221> NAME/KEY: CDS
<222> LOCATION: (1)..(1554)
<220> FEATURE:

```
<221> NAME/KEY: Pichia pastoris PDI1 Gene
<222> LOCATION: (1)..(1554)

<400> SEQUENCE: 21 atg caa ttc aac tgg aat att aaa act gtg gca agt att ttg tcc gct      48
Met Gln Phe Asn Trp Asn Ile Lys Thr Val Ala Ser Ile Leu Ser Ala
1               5                  10                  15 ctc aca cta gca caa gca agt gat cag gag gct att gct cca gag gac      96
Leu Thr Leu Ala Gln Ala Ser Asp Gln Glu Ala Ile Ala Pro Glu Asp
            20                  25                  30 tct cat gtc gtc aaa ttg act gaa gcc act ttt gag tct ttc atc acc     144
Ser His Val Val Lys Leu Thr Glu Ala Thr Phe Glu Ser Phe Ile Thr
        35                  40                  45 agt aat cct cac gtt ttg gca gag ttt ttt gcc cct tgg tgt ggt cac     192
Ser Asn Pro His Val Leu Ala Glu Phe Phe Ala Pro Trp Cys Gly His
    50                  55                  60 tgt aag aag ttg ggc cct gaa ctt gtt tct gct gcc gag atc tta aag     240
Cys Lys Lys Leu Gly Pro Glu Leu Val Ser Ala Ala Glu Ile Leu Lys
65                  70                  75                  80 gac aat gag cag gtt aag att gct caa att gat tgt acg gag gag aag     288
Asp Asn Glu Gln Val Lys Ile Ala Gln Ile Asp Cys Thr Glu Glu Lys
                85                  90                  95 gaa tta tgt caa ggc tac gaa att aaa ggg tat cct act ttg aag gtg     336
Glu Leu Cys Gln Gly Tyr Glu Ile Lys Gly Tyr Pro Thr Leu Lys Val
            100                 105                 110 ttc cat ggt gag gtt gag gtc cca agt gac tat caa ggt caa aga cag     384
Phe His Gly Glu Val Glu Val Pro Ser Asp Tyr Gln Gly Gln Arg Gln
        115                 120                 125 agc caa agc att gtc agc tat atg cta aag cag agt tta ccc cct gtc     432
Ser Gln Ser Ile Val Ser Tyr Met Leu Lys Gln Ser Leu Pro Pro Val
    130                 135                 140 agt gaa atc aat gca acc aaa gat tta gac gac aca atc gcc gag gca     480
Ser Glu Ile Asn Ala Thr Lys Asp Leu Asp Asp Thr Ile Ala Glu Ala
145                 150                 155                 160 aaa gag ccc gtg att gtg caa gta cta ccg gaa gat gca tcc aac ttg     528
Lys Glu Pro Val Ile Val Gln Val Leu Pro Glu Asp Ala Ser Asn Leu
                165                 170                 175 gaa tct aac acc aca ttt tac gga gtt gcc ggt act ctc aga gag aaa     576
Glu Ser Asn Thr Thr Phe Tyr Gly Val Ala Gly Thr Leu Arg Glu Lys
            180                 185                 190 ttc act ttt gtc tcc act aag tct act gat tat gcc aaa aaa tac act     624
Phe Thr Phe Val Ser Thr Lys Ser Thr Asp Tyr Ala Lys Lys Tyr Thr
        195                 200                 205 agc gac tcg act cct gcc tat ttg ctt gtc aga cct ggc gag gaa cct     672
Ser Asp Ser Thr Pro Ala Tyr Leu Leu Val Arg Pro Gly Glu Glu Pro
    210                 215                 220 agt gtt tac tct ggt gag gag tta gat gag act cat ttg gtg cac tgg     720
Ser Val Tyr Ser Gly Glu Glu Leu Asp Glu Thr His Leu Val His Trp
225                 230                 235                 240 att gat att gag tcc aaa cct cta ttt gga gac att gac gga tcc acc     768
Ile Asp Ile Glu Ser Lys Pro Leu Phe Gly Asp Ile Asp Gly Ser Thr
                245                 250                 255 ttc aaa tca tat gct gaa gct aac atc cct tta gcc tac tat ttc tat     816
Phe Lys Ser Tyr Ala Glu Ala Asn Ile Pro Leu Ala Tyr Tyr Phe Tyr
            260                 265                 270 gag aac gaa gaa caa cgt gct gct gct gcc gat att att aaa cct ttt     864
Glu Asn Glu Glu Gln Arg Ala Ala Ala Ala Asp Ile Ile Lys Pro Phe
        275                 280                 285 gct aaa gag caa cgt ggc aaa att aac ttt gtt ggc tta gat gcc gtt     912
Ala Lys Glu Gln Arg Gly Lys Ile Asn Phe Val Gly Leu Asp Ala Val
```

```
                        290                     295                     300
aaa ttc ggt aag cat gcc aag aac tta aac atg gat gaa gag aaa ctc      960
Lys Phe Gly Lys His Ala Lys Asn Leu Asn Met Asp Glu Glu Lys Leu
305                     310                     315                 320 cct cta ttt gtc att cat gat ttg gtg agc aac aag aag ttt gga gtt     1008
Pro Leu Phe Val Ile His Asp Leu Val Ser Asn Lys Lys Phe Gly Val
                325                     330                 335 cct caa gac caa gaa ttg acg aac aaa gat gtg acc gag ctg att gag     1056
Pro Gln Asp Gln Glu Leu Thr Asn Lys Asp Val Thr Glu Leu Ile Glu
        340                     345                 350 aaa ttc atc gca gga gag gca gaa cca att gtg aaa tca gag cca att     1104
Lys Phe Ile Ala Gly Glu Ala Glu Pro Ile Val Lys Ser Glu Pro Ile
355                     360                     365 cca gaa att caa gaa gag aaa gtc ttc aag cta gtc gga aag gcc cac     1152
Pro Glu Ile Gln Glu Glu Lys Val Phe Lys Leu Val Gly Lys Ala His
                370                     375                 380 gat gaa gtt gtc ttc gat gaa tct aaa gat gtt cta gtc aag tac tac     1200
Asp Glu Val Val Phe Asp Glu Ser Lys Asp Val Leu Val Lys Tyr Tyr
385                     390                     395                 400 gcc cct tgg tgt ggt cac tgt aag aga atg gct cct gct tat gag gaa     1248
Ala Pro Trp Cys Gly His Cys Lys Arg Met Ala Pro Ala Tyr Glu Glu
                    405                     410              415 ttg gct act ctt tac gcc aat gat gag gat gcc tct tca aag gtt gtg     1296
Leu Ala Thr Leu Tyr Ala Asn Asp Glu Asp Ala Ser Ser Lys Val Val
                420                     425                 430 att gca aaa ctt gat cac act ttg aac gat gtc gac aac gtt gat att     1344
Ile Ala Lys Leu Asp His Thr Leu Asn Asp Val Asp Asn Val Asp Ile
        435                     440                 445 caa ggt tat cct act ttg atc ctt tat cca gct ggt gat aaa tcc aat     1392
Gln Gly Tyr Pro Thr Leu Ile Leu Tyr Pro Ala Gly Asp Lys Ser Asn
450                     455                     460 cct caa ctg tat gat gga tct cgt gac cta gaa tca ttg gct gag ttt     1440
Pro Gln Leu Tyr Asp Gly Ser Arg Asp Leu Glu Ser Leu Ala Glu Phe
465                     470                     475                 480 gta aag gag aga gga acc cac aaa gtg gat gcc cta gca ctc aga cca     1488
Val Lys Glu Arg Gly Thr His Lys Val Asp Ala Leu Ala Leu Arg Pro
                    485                     490              495 gtc gag gaa gaa aag gaa gct gaa gaa gaa gct gaa agt gag gca gac     1536
Val Glu Glu Glu Lys Glu Ala Glu Glu Glu Ala Glu Ser Glu Ala Asp
                500                     505                 510 gct cac gac gag ctt taa                                             1554
Ala His Asp Glu Leu
        515
```

<210> SEQ ID NO 22
<211> LENGTH: 517
<212> TYPE: PRT
<213> ORGANISM: Pichia pastoris

<400> SEQUENCE: 22

```
Met Gln Phe Asn Trp Asn Ile Lys Thr Val Ala Ser Ile Leu Ser Ala
1               5                   10                  15

Leu Thr Leu Ala Gln Ala Ser Asp Gln Glu Ala Ile Ala Pro Glu Asp
            20                  25                  30

Ser His Val Val Lys Leu Thr Glu Ala Thr Phe Glu Ser Phe Ile Thr
        35                  40                  45

Ser Asn Pro His Val Leu Ala Glu Phe Phe Ala Pro Trp Cys Gly His
    50                  55                  60

Cys Lys Lys Leu Gly Pro Glu Leu Val Ser Ala Ala Glu Ile Leu Lys
```

```
                65                  70                  75                  80
Asp Asn Glu Gln Val Lys Ile Ala Gln Ile Asp Cys Thr Glu Glu Lys
                        85                  90                  95

Glu Leu Cys Gln Gly Tyr Glu Ile Lys Gly Tyr Pro Thr Leu Lys Val
               100                 105                 110

Phe His Gly Glu Val Glu Val Pro Ser Asp Tyr Gln Gly Gln Arg Gln
               115                 120                 125

Ser Gln Ser Ile Val Ser Tyr Met Leu Lys Gln Ser Leu Pro Pro Val
           130                 135                 140

Ser Glu Ile Asn Ala Thr Lys Asp Leu Asp Asp Thr Ile Ala Glu Ala
145                 150                 155                 160

Lys Glu Pro Val Ile Val Gln Val Leu Pro Glu Asp Ala Ser Asn Leu
                   165                 170                 175

Glu Ser Asn Thr Thr Phe Tyr Gly Val Ala Gly Thr Leu Arg Glu Lys
               180                 185                 190

Phe Thr Phe Val Ser Thr Lys Ser Thr Asp Tyr Ala Lys Lys Tyr Thr
           195                 200                 205

Ser Asp Ser Thr Pro Ala Tyr Leu Leu Val Arg Pro Gly Glu Glu Pro
       210                 215                 220

Ser Val Tyr Ser Gly Glu Glu Leu Asp Glu Thr His Leu Val His Trp
225                 230                 235                 240

Ile Asp Ile Glu Ser Lys Pro Leu Phe Gly Asp Ile Asp Gly Ser Thr
                   245                 250                 255

Phe Lys Ser Tyr Ala Glu Ala Asn Ile Pro Leu Ala Tyr Tyr Phe Tyr
               260                 265                 270

Glu Asn Glu Glu Gln Arg Ala Ala Ala Asp Ile Ile Lys Pro Phe
           275                 280                 285

Ala Lys Glu Gln Arg Gly Lys Ile Asn Phe Val Gly Leu Asp Ala Val
       290                 295                 300

Lys Phe Gly Lys His Ala Lys Asn Leu Asn Met Asp Glu Glu Lys Leu
305                 310                 315                 320

Pro Leu Phe Val Ile His Asp Leu Val Ser Asn Lys Lys Phe Gly Val
                   325                 330                 335

Pro Gln Asp Gln Glu Leu Thr Asn Lys Asp Val Thr Glu Leu Ile Glu
               340                 345                 350

Lys Phe Ile Ala Gly Glu Ala Glu Pro Ile Val Lys Ser Glu Pro Ile
           355                 360                 365

Pro Glu Ile Gln Glu Glu Lys Val Phe Lys Leu Val Gly Lys Ala His
       370                 375                 380

Asp Glu Val Val Phe Asp Glu Ser Lys Asp Val Leu Val Lys Tyr Tyr
385                 390                 395                 400

Ala Pro Trp Cys Gly His Cys Lys Arg Met Ala Pro Ala Tyr Glu Glu
                   405                 410                 415

Leu Ala Thr Leu Tyr Ala Asn Asp Glu Asp Ala Ser Ser Lys Val Val
               420                 425                 430

Ile Ala Lys Leu Asp His Thr Leu Asn Asp Val Asp Asn Val Asp Ile
           435                 440                 445

Gln Gly Tyr Pro Thr Leu Ile Leu Tyr Pro Ala Gly Asp Lys Ser Asn
       450                 455                 460

Pro Gln Leu Tyr Asp Gly Ser Arg Asp Leu Glu Ser Leu Ala Glu Phe
465                 470                 475                 480

Val Lys Glu Arg Gly Thr His Lys Val Asp Ala Leu Ala Leu Arg Pro
                   485                 490                 495
```

-continued

```
Val Glu Glu Glu Lys Glu Ala Glu Glu Ala Glu Ser Glu Ala Asp
            500                 505                 510

Ala His Asp Glu Leu
        515

<210> SEQ ID NO 23
<211> LENGTH: 1554
<212> TYPE: PRT
<213> ORGANISM: Pichia pastoris

<400> SEQUENCE: 23

Ala Thr Gly Cys Ala Ala Thr Thr Cys Ala Ala Cys Thr Gly Gly Ala
1               5                   10                  15

Ala Thr Ala Thr Thr Ala Ala Ala Ala Cys Thr Gly Thr Gly Gly Cys
            20                  25                  30

Ala Ala Gly Thr Ala Thr Thr Thr Gly Thr Cys Cys Gly Cys Thr
        35                  40                  45

Cys Thr Cys Ala Cys Ala Cys Thr Ala Gly Cys Ala Cys Ala Ala Gly
    50                  55                  60

Cys Ala Ala Gly Thr Gly Ala Thr Cys Ala Gly Gly Ala Gly Gly Cys
65                  70                  75                  80

Thr Ala Thr Thr Gly Cys Thr Cys Ala Gly Ala Gly Gly Ala Cys
                85                  90                  95

Thr Cys Thr Cys Ala Thr Gly Thr Cys Gly Thr Cys Ala Ala Ala Thr
            100                 105                 110

Thr Gly Ala Cys Thr Gly Ala Ala Gly Cys Cys Ala Cys Thr Thr Thr
        115                 120                 125

Thr Gly Ala Gly Thr Cys Thr Thr Thr Cys Ala Thr Cys Ala Cys Cys
    130                 135                 140

Ala Gly Thr Ala Ala Thr Cys Cys Thr Cys Ala Cys Gly Thr Thr Thr
145                 150                 155                 160

Thr Gly Gly Cys Ala Gly Ala Gly Thr Thr Thr Thr Thr Gly Cys
                165                 170                 175

Cys Cys Cys Thr Thr Gly Gly Thr Gly Thr Gly Gly Thr Cys Ala Cys
            180                 185                 190

Thr Gly Thr Ala Ala Gly Ala Ala Gly Thr Thr Gly Gly Cys Cys
        195                 200                 205

Cys Thr Gly Ala Ala Cys Thr Thr Gly Thr Thr Thr Cys Thr Gly Cys
    210                 215                 220

Thr Gly Cys Cys Gly Ala Gly Ala Thr Cys Thr Thr Ala Ala Ala Gly
225                 230                 235                 240

Gly Ala Cys Ala Ala Thr Gly Ala Gly Cys Ala Gly Gly Thr Thr Ala
                245                 250                 255

Ala Gly Ala Thr Thr Gly Cys Thr Cys Ala Ala Ala Thr Thr Gly Ala
            260                 265                 270

Thr Thr Gly Thr Ala Cys Gly Gly Ala Gly Gly Ala Gly Ala Ala Gly
        275                 280                 285

Gly Ala Ala Thr Thr Ala Thr Gly Thr Cys Ala Ala Gly Gly Cys Thr
    290                 295                 300

Ala Cys Gly Ala Ala Ala Thr Ala Ala Ala Gly Gly Gly Thr Ala
305                 310                 315                 320

Thr Cys Cys Thr Ala Cys Thr Thr Gly Ala Ala Gly Gly Thr Gly
                325                 330                 335

Thr Thr Cys Cys Ala Thr Gly Gly Thr Gly Ala Gly Gly Thr Thr Gly
```

-continued

```
            340                 345                 350

Ala Gly Gly Thr Cys Cys Cys Ala Ala Gly Thr Gly Ala Cys Thr Ala
        355                 360                 365

Thr Cys Ala Ala Gly Gly Thr Cys Ala Ala Ala Gly Ala Cys Ala Gly
    370                 375                 380

Ala Gly Cys Cys Ala Ala Ala Gly Cys Ala Thr Thr Gly Thr Cys Ala
385                 390                 395                 400

Gly Cys Thr Ala Thr Ala Thr Gly Cys Thr Ala Ala Ala Gly Cys Ala
                405                 410                 415

Gly Ala Gly Thr Thr Thr Ala Cys Cys Cys Cys Cys Thr Gly Thr Cys
            420                 425                 430

Ala Gly Thr Gly Ala Ala Ala Thr Cys Ala Ala Thr Gly Cys Ala Ala
        435                 440                 445

Cys Cys Ala Ala Ala Gly Ala Thr Thr Thr Ala Gly Ala Cys Gly Ala
    450                 455                 460

Cys Ala Cys Ala Ala Thr Cys Gly Cys Cys Gly Ala Gly Gly Cys Ala
465                 470                 475                 480

Ala Ala Ala Gly Ala Gly Cys Cys Cys Gly Thr Gly Ala Thr Thr Gly
                485                 490                 495

Thr Gly Cys Ala Ala Gly Thr Ala Cys Thr Ala Cys Cys Gly Gly Ala
            500                 505                 510

Ala Gly Ala Thr Gly Cys Ala Thr Cys Cys Ala Ala Cys Thr Thr Gly
        515                 520                 525

Gly Ala Ala Thr Cys Thr Ala Ala Cys Ala Cys Cys Ala Cys Ala Thr
    530                 535                 540

Thr Thr Thr Ala Cys Gly Gly Ala Gly Thr Thr Gly Cys Cys Gly Gly
545                 550                 555                 560

Thr Ala Cys Thr Cys Thr Cys Ala Gly Ala Gly Ala Gly Ala Ala Ala
                565                 570                 575

Thr Thr Cys Ala Cys Thr Thr Thr Thr Gly Thr Cys Thr Cys Cys Ala
            580                 585                 590

Cys Thr Ala Ala Gly Thr Cys Thr Ala Cys Thr Gly Ala Thr Thr Ala
        595                 600                 605

Thr Gly Cys Cys Ala Ala Ala Ala Ala Ala Thr Ala Cys Ala Cys Thr
    610                 615                 620

Ala Gly Cys Gly Ala Cys Thr Cys Gly Ala Cys Thr Cys Cys Thr Gly
625                 630                 635                 640

Cys Cys Thr Ala Thr Thr Thr Gly Cys Thr Thr Gly Thr Cys Ala Gly
                645                 650                 655

Ala Cys Cys Thr Gly Gly Cys Gly Ala Gly Gly Ala Ala Cys Cys Thr
            660                 665                 670

Ala Gly Thr Gly Thr Thr Thr Ala Cys Thr Cys Thr Gly Gly Thr Gly
        675                 680                 685

Ala Gly Gly Ala Gly Thr Thr Ala Gly Ala Thr Gly Ala Gly Ala Cys
    690                 695                 700

Thr Cys Ala Thr Thr Thr Gly Gly Thr Gly Cys Ala Cys Thr Gly Gly
705                 710                 715                 720

Ala Thr Thr Gly Ala Thr Ala Thr Thr Gly Ala Gly Thr Cys Cys Ala
                725                 730                 735

Ala Ala Cys Cys Thr Cys Thr Ala Thr Thr Thr Gly Gly Ala Gly Ala
            740                 745                 750

Cys Ala Thr Thr Gly Ala Cys Gly Gly Ala Thr Cys Cys Ala Cys Cys
        755                 760                 765
```

-continued

Thr Thr Cys Ala Ala Thr Cys Ala Thr Thr Gly Cys Thr Gly
770                 775                 780

Ala Ala Gly Cys Thr Ala Ala Cys Ala Thr Cys Cys Thr Thr Thr
785                 790                 795                 800

Ala Gly Cys Cys Thr Ala Cys Thr Ala Thr Thr Cys Thr Ala Thr
                805                 810                 815

Gly Ala Gly Ala Ala Cys Gly Ala Ala Gly Ala Ala Cys Ala Ala Cys
                820                 825                 830

Gly Thr Gly Cys Thr Gly Cys Thr Gly Cys Thr Gly Cys Cys Gly Ala
                835                 840                 845

Thr Ala Thr Thr Ala Thr Thr Ala Ala Ala Cys Cys Thr Thr Thr Thr
850                 855                 860

Gly Cys Thr Ala Ala Gly Ala Gly Cys Ala Ala Cys Gly Thr Gly
865                 870                 875                 880

Gly Cys Ala Ala Ala Ala Thr Thr Ala Ala Cys Thr Thr Thr Gly Thr
                885                 890                 895

Thr Gly Gly Cys Thr Thr Ala Gly Ala Thr Gly Cys Cys Gly Thr Thr
                900                 905                 910

Ala Ala Ala Thr Thr Cys Gly Gly Thr Ala Ala Gly Cys Ala Thr Gly
                915                 920                 925

Cys Cys Ala Ala Gly Ala Ala Cys Thr Thr Ala Ala Ala Cys Ala Thr
                930                 935                 940

Gly Gly Ala Thr Gly Ala Ala Gly Ala Gly Ala Ala Ala Cys Thr Cys
945                 950                 955                 960

Cys Cys Thr Cys Thr Ala Thr Thr Thr Gly Thr Cys Ala Thr Thr Cys
                965                 970                 975

Ala Thr Gly Ala Thr Thr Thr Gly Gly Thr Gly Ala Gly Cys Ala Ala
                980                 985                 990

Cys Ala Ala Gly Ala Ala Gly Thr Thr Thr Gly Gly Ala Gly Thr Thr
                995                 1000                1005

Cys Cys Thr Cys Ala Ala Gly Ala Cys Ala Ala Gly Ala Ala
                1010                1015                1020

Thr Thr Gly Ala Cys Gly Ala Ala Cys Ala Ala Ala Gly Ala Thr
                1025                1030                1035

Gly Thr Gly Ala Cys Cys Gly Ala Gly Cys Thr Gly Ala Thr Thr
                1040                1045                1050

Gly Ala Gly Ala Ala Ala Thr Thr Cys Ala Thr Cys Gly Cys Ala
                1055                1060                1065

Gly Gly Ala Gly Ala Gly Gly Cys Ala Gly Ala Ala Cys Cys Ala
                1070                1075                1080

Ala Thr Thr Gly Thr Gly Ala Ala Ala Thr Cys Ala Gly Ala Gly
                1085                1090                1095

Cys Cys Ala Ala Thr Thr Cys Cys Ala Gly Ala Ala Ala Thr Thr
                1100                1105                1110

Cys Ala Ala Gly Ala Ala Gly Ala Gly Ala Ala Ala Gly Thr Cys
                1115                1120                1125

Thr Thr Cys Ala Ala Gly Cys Thr Ala Gly Thr Cys Gly Gly Ala
                1130                1135                1140

Ala Ala Gly Gly Cys Cys Cys Ala Cys Gly Ala Thr Gly Ala Ala
                1145                1150                1155

Gly Thr Thr Gly Thr Cys Thr Thr Cys Gly Ala Thr Gly Ala Ala
                1160                1165                1170

```
Thr Cys Thr Ala Ala Ala Gly Ala Thr Thr  Cys Thr Ala
    1175                1180               1185

Gly Thr Cys Ala Ala Gly Thr  Ala Cys Thr Ala Cys  Gly Cys Cys
    1190                1195                1200

Cys Cys Thr Thr Gly Gly Thr  Gly Thr Gly Gly Thr  Cys Ala Cys
    1205                1210                1215

Thr Gly Thr Ala Ala Gly Ala  Gly Ala Ala Thr Gly  Gly Cys Thr
    1220                1225                1230

Cys Cys Thr Gly Cys Thr Thr  Ala Thr Gly Ala Gly  Gly Ala Ala
    1235                1240                1245

Thr Thr Gly Gly Cys Thr Ala  Cys Thr Cys Thr Thr  Thr Ala Cys
    1250                1255                1260

Gly Cys Cys Ala Ala Thr Gly  Ala Thr Gly Ala Gly  Gly Ala Thr
    1265                1270                1275

Gly Cys Cys Thr Cys Thr Thr  Cys Ala Ala Ala Gly  Gly Thr Thr
    1280                1285                1290

Gly Thr Gly Ala Thr Thr Gly  Cys Ala Ala Ala Cys  Thr Thr
    1295                1300                1305

Gly Ala Thr Cys Ala Cys Ala  Cys Thr Thr Thr Gly  Ala Ala Cys
    1310                1315                1320

Gly Ala Thr Gly Thr Cys Gly  Ala Cys Ala Ala Cys  Gly Thr Thr
    1325                1330                1335

Gly Ala Thr Ala Thr Thr Cys  Ala Ala Gly Gly Thr  Thr Ala Thr
    1340                1345                1350

Cys Cys Thr Ala Cys Thr Thr  Thr Gly Ala Thr Cys  Cys Thr Thr
    1355                1360                1365

Thr Ala Thr Cys Cys Ala Gly  Cys Thr Gly Gly Thr  Gly Ala Thr
    1370                1375                1380

Ala Ala Ala Thr Cys Cys Ala  Ala Thr Cys Cys Thr  Cys Ala Ala
    1385                1390                1395

Cys Thr Gly Thr Ala Thr Gly  Ala Thr Gly Gly Ala  Thr Cys Thr
    1400                1405                1410

Cys Gly Thr Gly Ala Cys Cys  Thr Ala Gly Ala Ala  Thr Cys Ala
    1415                1420                1425

Thr Thr Gly Gly Cys Thr Gly  Ala Gly Thr Thr Thr  Gly Thr Ala
    1430                1435                1440

Ala Ala Gly Gly Ala Gly Ala  Gly Ala Gly Gly Ala  Ala Cys Cys
    1445                1450                1455

Cys Ala Cys Ala Ala Ala Gly  Thr Gly Gly Ala Thr  Gly Cys Cys
    1460                1465                1470

Cys Thr Ala Gly Cys Ala Cys  Thr Cys Ala Gly Ala  Cys Cys Ala
    1475                1480                1485

Gly Thr Cys Gly Ala Gly Gly  Ala Ala Gly Ala Ala  Ala Ala Gly
    1490                1495                1500

Gly Ala Ala Gly Cys Thr Gly  Ala Ala Gly Ala Ala  Gly Ala Ala
    1505                1510                1515

Gly Cys Thr Gly Ala Ala Ala  Gly Thr Gly Ala Gly  Gly Cys Ala
    1520                1525                1530

Gly Ala Cys Gly Cys Thr Cys  Ala Cys Gly Ala Cys  Gly Ala Gly
    1535                1540                1545

Cys Thr Thr Thr Ala Ala
    1550
```

<210> SEQ ID NO 24
<211> LENGTH: 1337
<212> TYPE: DNA
<213> ORGANISM: Artificial Sequence
<220> FEATURE:
<223> OTHER INFORMATION: human ERO1alpha without leader

<400> SEQUENCE: 24

```
gaagaacaac caccagagac tgctgctcag agatgcttct gtcaggtttc cggttacttg      60
gacgactgta cttgtgacgt tgagactatc gacagattca acaactacag attgttccca     120
agattgcaga agttgttgga gtccgactac ttcagatact acaaggttaa cttgaagaga     180
ccatgtccat tctggaacga catttcccag tgtggtagaa gagactgtgc tgttaagcca     240
tgtcaatccg acgaagttcc agacggtatt aagtccgctt cctacaagta ctctgaagag     300
gctaacaact tgatcgaaga gtgtgagcaa gctgaaagat gggtgctgt tgacgaatct     360
ttgtccgaga gactcagaag gctgttttgc agtggactaa gcacgatgat tcctccgaca     420
acttctgtga agctgacgac attcaatctc cagaggctga gtacgttgac ttgttgttga     480
acccagagag atacactggt tacaagggtc agacgcttg aagatttgg aacgttatct     540
acgaagagaa ctgtttcaag ccacagacta tcaagagacc attgaaccca ttggcttccg     600
gacagggaac ttctgaagag aacactttct actcttggtt ggagggtttg tgtgttgaga     660
agagagcttt ctacagattg atctccggat gcacgcttc tatcaacgtt cacttgtccg     720
ctagatactt gttgcaagag acttggttgg aaaagaagtg gggtcacaac attactgagt     780
tccagcagag attcgacggt attttgactg aaggtgaagg tccaagaaga ttgaagaact     840
tgtactttt gtacttgatc gagttgagag ctttgtccaa ggttttgcca ttcttcgaga     900
gaccagactt ccaattgttc actggtaaca agatccagga cgaagagaac aagatgttgt     960
tgttggagat tttgcacgag atcaagtcct ttccattgca cttcgacgag aactcatttt    1020
tcgctggtga caagaaagaa gctcacaagt tgaaagagga cttcagattg cacttcagaa    1080
atatctccag aatcatggac tgtgttggtt gtttcaagtg tagattgtgg ggtaagttgc    1140
agactcaagg attgggtact gctttgaaga ttttgttctc cgagaagttg atcgctaaca    1200
tgcctgaatc tggtccatct tacgagttcc acttgactag acaagagatc gtttccttgt    1260
tcaacgcttt cggtagaatc tccacttccg ttaaagagtt ggagaacttc agaaacttgt    1320
tgcagaacat ccactaa                                                   1337
```

<210> SEQ ID NO 25
<211> LENGTH: 445
<212> TYPE: PRT
<213> ORGANISM: Artificial Sequence
<220> FEATURE:
<223> OTHER INFORMATION: human ERO1alpha without leader

<400> SEQUENCE: 25

```
Glu Glu Gln Pro Pro Glu Thr Ala Ala Gln Arg Cys Phe Cys Gln Val
1               5                   10                  15

Ser Gly Tyr Leu Asp Asp Cys Thr Cys Asp Val Glu Thr Ile Asp Arg
            20                  25                  30

Phe Asn Asn Tyr Arg Leu Phe Pro Arg Leu Gln Lys Leu Leu Glu Ser
        35                  40                  45

Asp Tyr Phe Arg Tyr Tyr Lys Val Asn Leu Lys Arg Pro Cys Pro Phe
    50                  55                  60

Trp Asn Asp Ile Ser Gln Cys Gly Arg Arg Asp Cys Ala Val Lys Pro
65                  70                  75                  80
```

```
Cys Gln Ser Asp Glu Val Pro Asp Gly Ile Lys Ser Ala Ser Tyr Lys
                 85                  90                  95

Tyr Ser Glu Glu Ala Asn Asn Leu Ile Glu Glu Cys Glu Gln Ala Glu
            100                 105                 110

Arg Leu Gly Ala Val Asp Glu Ser Leu Ser Glu Thr Gln Lys Ala
        115                 120                 125

Val Leu Gln Trp Thr Lys His Asp Asp Ser Ser Asp Asn Phe Cys Glu
130                 135                 140

Ala Asp Asp Ile Gln Ser Pro Glu Ala Glu Tyr Val Asp Leu Leu Leu
145                 150                 155                 160

Asn Pro Glu Arg Tyr Thr Gly Tyr Lys Gly Pro Asp Ala Trp Lys Ile
                165                 170                 175

Trp Asn Val Ile Tyr Glu Glu Asn Cys Phe Lys Pro Gln Thr Ile Lys
            180                 185                 190

Arg Pro Leu Asn Pro Leu Ala Ser Gly Gln Gly Thr Ser Glu Glu Asn
        195                 200                 205

Thr Phe Tyr Ser Trp Leu Glu Gly Leu Cys Val Glu Lys Arg Ala Phe
210                 215                 220

Tyr Arg Leu Ile Ser Gly Leu His Ala Ser Ile Asn Val His Leu Ser
225                 230                 235                 240

Ala Arg Tyr Leu Leu Gln Glu Thr Trp Leu Glu Lys Lys Trp Gly His
                245                 250                 255

Asn Ile Thr Glu Phe Gln Gln Arg Phe Asp Gly Ile Leu Thr Glu Gly
            260                 265                 270

Glu Gly Pro Arg Arg Leu Lys Asn Leu Tyr Phe Leu Tyr Leu Ile Glu
        275                 280                 285

Leu Arg Ala Leu Ser Lys Val Leu Pro Phe Glu Arg Pro Asp Phe
290                 295                 300

Gln Leu Phe Thr Gly Asn Lys Ile Gln Asp Glu Glu Asn Lys Met Leu
305                 310                 315                 320

Leu Leu Glu Ile Leu His Glu Ile Lys Ser Phe Pro Leu His Phe Asp
                325                 330                 335

Glu Asn Ser Phe Phe Ala Gly Asp Lys Lys Glu Ala His Lys Leu Lys
            340                 345                 350

Glu Asp Phe Arg Leu His Phe Arg Asn Ile Ser Arg Ile Met Asp Cys
        355                 360                 365

Val Gly Cys Phe Lys Cys Arg Leu Trp Gly Lys Leu Gln Thr Gln Gly
370                 375                 380

Leu Gly Thr Ala Leu Lys Ile Leu Phe Ser Glu Lys Leu Ile Ala Asn
385                 390                 395                 400

Met Pro Glu Ser Gly Pro Ser Tyr Glu Phe His Leu Thr Arg Gln Glu
                405                 410                 415

Ile Val Ser Leu Phe Asn Ala Phe Gly Arg Ile Ser Thr Ser Val Lys
            420                 425                 430

Glu Leu Glu Asn Phe Arg Asn Leu Leu Gln Asn Ile His
        435                 440                 445

<210> SEQ ID NO 26
<211> LENGTH: 2349
<212> TYPE: DNA
<213> ORGANISM: Artificial Sequence
<220> FEATURE:
<223> OTHER INFORMATION: human GRP94 without leader

<400> SEQUENCE: 26
```

```
gatgatgaag ttgacgttga cggtactgtt gaagaggact tgggaaagtc tagagagggt    60
tccagaactg acgacgaagt tgttcagaga gaggaagagg ctattcagtt ggacggattg   120
aacgcttccc aaatcagaga gttgagagag aagtccgaga agttcgcttt ccaagctgag   180
gttaacagaa tgatgaaatt gattatcaac tccttgtaca agaacaaaga gattttcttg   240
agagagttga tctctaacgc ttctgacgct ttggacaaga tcagattgat ctccttgact   300
gacgaaaacg ctttgtccgg taacgaagag ttgactgtta agatcaagtg tgacaaagag   360
aagaacttgt tgcacgttac tgacactggt gttggaatga ctagagaaga gttggttaag   420
aacttgggta ctatcgctaa gtctggtact tccgagttct tgaacaagat gactgaggct   480
caagaagatg gtcaatccac ttccgagttg attggtcagt tcggtgttgg tttctactcc   540
gctttcttgg ttgctgacaa ggttatcgtt acttccaagc acaacaacga cactcaacac   600
atttgggaat ccgattccaa cgagttctcc gttattgctg acccaagagg taacactttg   660
ggtagaggta ctactatcac tttggttttg aaagaagagg cttccgacta cttggagttg   720
gacactatca agaacttggt taagaagtac tcccagttca tcaacttccc aatctatgtt   780
tggtcctcca agactgagac tgttgaggaa ccaatggaag aagaagaggc tgctaaagaa   840
gagaaagagg aatctgacga cgaggctgct gttgaagaag aggaagaaga aaagaagcca   900
aagactaaga aggttgaaaa gactgttttgg gactgggagc ttatgaacga catcaagcca   960
atttggcaga gaccatccaa agaggttgag gaggacgagt acaaggcttt ctacaagtcc  1020
ttctccaaag aatccgatga cccaatggct tacatccact tcactgctga gggtgaagtt  1080
actttcaagt ccatcttgtt cgttccaact tctgctccaa gaggattgtt cgacgagtac  1140
ggttctaaga agtccgacta catcaaactt tatgttagaa gagttttcat cactgacgac  1200
ttccacgata tgatgccaaa gtacttgaac ttcgttaagg gtgttgttga ttccgatgac  1260
ttgccattga acgtttccag agagactttg cagcagcaca agttgttgaa ggttatcaga  1320
aagaaacttg ttagaaagac tttggacatg atcaagaaga tcgctgacga caagtacaac  1380
gacactttct ggaaagagtt cggaactaac atcaagttgg gtgttattga ggaccactcc  1440
aacagaacta gattggctaa gttgttgaga ttccagtcct ctcatcaccc aactgacatc  1500
acttccttgg accagtacgt tgagagaatg aaagagaagc aggacaaaat ctacttcatg  1560
gctggttcct ctagaaaaga ggctgaatcc tccccattcg ttgagagatt gttgaagaag  1620
ggttacgagg ttatctactt gactgagcca gttgacgagt actgtatcca ggctttgcca  1680
gagtttgacg gaaagagatt ccagaacgtt gctaaagagg gtgttaagtt cgacgaatcc  1740
gaaaagacta agaatccag agaggctgtt gagaaagagt tcgagccatt gttgaactgg  1800
atgaaggaca aggctttgaa ggacaagatc gagaaggctg ttgtttccca gagattgact  1860
gaatccccat gtgctttggt tgcttcccaa tacggatgga gtggtaacat ggaaagaatc  1920
atgaaggctc aggcttacca aactggaaag gacatctcca ctaactacta cgcttcccag  1980
aagaaaactt tcgagatcaa cccaagacac ccattgatca gagacatgtt gagaagaatc  2040
aaagaggacg aggacgacaa gactgttttg gatttggctg ttgttttgtt cgagactgct  2100
actttgagat ccggttactt gttgccagac actaaggctt acggtgacag aatcgagaga  2160
atgttgagat tgtccttgaa cattgaccca gacgctaagg ttgaagaaga accagaagaa  2220
gagccagagg aaactgctga agatactact gaggacactg aacaagacga ggacgaagag  2280
atggatgttg gtactgacga gaggaagagg acagcaaagg aatccactgc tgaacacgac  2340
```

```
gagttgtaa                                                                    2349
```

<210> SEQ ID NO 27
<211> LENGTH: 782
<212> TYPE: PRT
<213> ORGANISM: Artificial Sequence
<220> FEATURE:
<223> OTHER INFORMATION: human GRP94 without leader

<400> SEQUENCE: 27

```
Asp Asp Glu Val Asp Val Asp Gly Thr Val Glu Glu Asp Leu Gly Lys
1               5                   10                  15

Ser Arg Glu Gly Ser Arg Thr Asp Asp Glu Val Val Gln Arg Glu Glu
            20                  25                  30

Glu Ala Ile Gln Leu Asp Gly Leu Asn Ala Ser Gln Ile Arg Glu Leu
        35                  40                  45

Arg Glu Lys Ser Glu Lys Phe Ala Phe Gln Ala Glu Val Asn Arg Met
    50                  55                  60

Met Lys Leu Ile Ile Asn Ser Leu Tyr Lys Asn Lys Glu Ile Phe Leu
65                  70                  75                  80

Arg Glu Leu Ile Ser Asn Ala Ser Asp Ala Leu Asp Lys Ile Arg Leu
                85                  90                  95

Ile Ser Leu Thr Asp Glu Asn Ala Leu Ser Gly Asn Glu Glu Leu Thr
            100                 105                 110

Val Lys Ile Lys Cys Asp Lys Glu Lys Asn Leu Leu His Val Thr Asp
        115                 120                 125

Thr Gly Val Gly Met Thr Arg Glu Glu Leu Val Lys Asn Leu Gly Thr
    130                 135                 140

Ile Ala Lys Ser Gly Thr Ser Glu Phe Leu Asn Lys Met Thr Glu Ala
145                 150                 155                 160

Gln Glu Asp Gly Gln Ser Thr Ser Glu Leu Ile Gly Gln Phe Gly Val
                165                 170                 175

Gly Phe Tyr Ser Ala Phe Leu Val Ala Asp Lys Val Ile Val Thr Ser
            180                 185                 190

Lys His Asn Asn Asp Thr Gln His Ile Trp Glu Ser Asp Ser Asn Glu
        195                 200                 205

Phe Ser Val Ile Ala Asp Pro Arg Gly Asn Thr Leu Gly Arg Gly Thr
    210                 215                 220

Thr Ile Thr Leu Val Leu Lys Glu Glu Ala Ser Asp Tyr Leu Glu Leu
225                 230                 235                 240

Asp Thr Ile Lys Asn Leu Val Lys Lys Tyr Ser Gln Phe Ile Asn Phe
                245                 250                 255

Pro Ile Tyr Val Trp Ser Ser Lys Thr Glu Thr Val Glu Glu Pro Met
            260                 265                 270

Glu Glu Glu Glu Ala Ala Lys Glu Glu Lys Glu Glu Ser Asp Asp Glu
        275                 280                 285

Ala Ala Val Glu Glu Glu Glu Glu Lys Lys Pro Lys Thr Lys Lys Lys
    290                 295                 300

Val Glu Lys Thr Val Trp Asp Trp Glu Leu Met Asn Asp Ile Lys Pro
305                 310                 315                 320

Ile Trp Gln Arg Pro Ser Lys Glu Val Glu Asp Glu Tyr Lys Ala
                325                 330                 335

Phe Tyr Lys Ser Phe Ser Lys Glu Ser Asp Asp Pro Met Ala Tyr Ile
            340                 345                 350

His Phe Thr Ala Glu Gly Glu Val Thr Phe Lys Ser Ile Leu Phe Val
```

-continued

```
            355                 360                 365
Pro Thr Ser Ala Pro Arg Gly Leu Phe Asp Glu Tyr Gly Ser Lys Lys
370                 375                 380

Ser Asp Tyr Ile Lys Leu Tyr Val Arg Arg Val Phe Ile Thr Asp Asp
385                 390                 395                 400

Phe His Asp Met Met Pro Lys Tyr Leu Asn Phe Val Lys Gly Val Val
                405                 410                 415

Asp Ser Asp Asp Leu Pro Leu Asn Val Ser Arg Glu Thr Leu Gln Gln
                420                 425                 430

His Lys Leu Leu Lys Val Ile Arg Lys Lys Leu Val Arg Lys Thr Leu
            435                 440                 445

Asp Met Ile Lys Lys Ile Ala Asp Asp Lys Tyr Asn Asp Thr Phe Trp
450                 455                 460

Lys Glu Phe Gly Thr Asn Ile Lys Leu Gly Val Ile Glu Asp His Ser
465                 470                 475                 480

Asn Arg Thr Arg Leu Ala Lys Leu Leu Arg Phe Gln Ser Ser His His
                485                 490                 495

Pro Thr Asp Ile Thr Ser Leu Asp Gln Tyr Val Glu Arg Met Lys Glu
                500                 505                 510

Lys Gln Asp Lys Ile Tyr Phe Met Ala Gly Ser Ser Arg Lys Glu Ala
            515                 520                 525

Glu Ser Ser Pro Phe Val Glu Arg Leu Leu Lys Lys Gly Tyr Glu Val
530                 535                 540

Ile Tyr Leu Thr Glu Pro Val Asp Glu Tyr Cys Ile Gln Ala Leu Pro
545                 550                 555                 560

Glu Phe Asp Gly Lys Arg Phe Gln Asn Val Ala Lys Glu Gly Val Lys
                565                 570                 575

Phe Asp Glu Ser Glu Lys Thr Lys Glu Ser Arg Glu Ala Val Glu Lys
                580                 585                 590

Glu Phe Glu Pro Leu Leu Asn Trp Met Lys Asp Lys Ala Leu Lys Asp
            595                 600                 605

Lys Ile Glu Lys Ala Val Val Ser Gln Arg Leu Thr Glu Ser Pro Cys
610                 615                 620

Ala Leu Val Ala Ser Gln Tyr Gly Trp Ser Gly Asn Met Glu Arg Ile
625                 630                 635                 640

Met Lys Ala Gln Ala Tyr Gln Thr Gly Lys Asp Ile Ser Thr Asn Tyr
                645                 650                 655

Tyr Ala Ser Gln Lys Lys Thr Phe Glu Ile Asn Pro Arg His Pro Leu
                660                 665                 670

Ile Arg Asp Met Leu Arg Arg Ile Lys Glu Asp Glu Asp Asp Lys Thr
            675                 680                 685

Val Leu Asp Leu Ala Val Val Leu Phe Glu Thr Ala Thr Leu Arg Ser
690                 695                 700

Gly Tyr Leu Leu Pro Asp Thr Lys Ala Tyr Gly Asp Arg Ile Glu Arg
705                 710                 715                 720

Met Leu Arg Leu Ser Leu Asn Ile Asp Pro Asp Ala Lys Val Glu Glu
                725                 730                 735

Glu Pro Glu Glu Glu Pro Glu Glu Thr Ala Glu Asp Thr Thr Glu Asp
                740                 745                 750

Thr Glu Gln Asp Glu Asp Glu Glu Met Asp Val Gly Thr Asp Glu Glu
            755                 760                 765

Glu Glu Thr Ala Lys Glu Ser Thr Ala Glu His Asp Glu Leu
770                 775                 780
```

<210> SEQ ID NO 28
<211> LENGTH: 1380
<212> TYPE: DNA
<213> ORGANISM: Artificial Sequence
<220> FEATURE:
<223> OTHER INFORMATION: anti-DKK1 Heavy chain (VH + IgG2m4) with
      alpha-amylase leader

<400> SEQUENCE: 28

```
acgatggtcg cttggtggtc tttgtttctg tacggtcttc aggtcgctgc acctgctttg      60
gctgaggttc agttggttca atctggtgct gaggttaaga aacctggtgc ttccgttaag     120
gtttcctgta aggcttccgg ttacactttc actgactact acatccactg ggttagacaa     180
gctccaggtc aaggattgga atggatggga tggattcact ctaactccgg tgctactact     240
tacgctcaga gttccaggc tagagttact atgtccagag acacttcttc ttccactgct      300
tacatggaat gtccagatt ggaatccgat gacactgcta tgtacttttg ttccagagag      360
gactactggg acagggaac tttggttact gtttcctccg cttctactaa agggccctct      420
gttttttccat ggctccatg ttctagatcc acttccgaat ccactgctgc tttgggatgt     480
ttggttaagg actactccc agagccagtt actgtttctt ggaactccgg tgctttgact     540
tctggtgttc acttttcc agctgttttg caatcttccg gtttgtactc cttgtcctcc       600
gttgttactg ttacttcctc caacttcggt actcagactt acacttgtaa cgttgaccac    660
aagccatcca cactaaggt tgacaagact gttgagagaa agtgttgtgt tgagtgtcca     720
ccatgtccag ctccaccagt tgctggtcca tccgtttttt tgttcccacc aaagccaaag   780
gacactttga tgatctccag aactccagag gttacatgtg ttgttgttga cgtttcccaa   840
gaggacccag aggttcaatt caactggtac gttgacggtg ttgaagttca caacgctaag    900
actaagccaa gagaagagca gttcaactcc actttcagag ttgtttccgt tttgactgtt    960
ttgcaccagg attggttgaa cggtaaagaa tacaagtgta aggtttccaa caagggattg  1020
ccatcctcca tcgaaaagac tatctccaag actaagggac aaccaagaga gccacaggtt 1080
tacactttgc caccatccag agaagagatg actaagaacc aggtttcctt gacttgtttg  1140
gttaaaggat tctacccatc cgacattgct gttgagtggg aatctaacgg tcaaccagag 1200
aacaactaca agactactcc accaatgttg gattctgacg gttccttctt cttgtactcc  1260
aagttgactg ttgacaagtc cagatggcaa cagggtaacg tttttctcctg ttccgttatg 1320
catgaggctt gcacaaacca ctacactcaa aagtccttgt ctttgtcccc tggtaagtaa  1380
```

<210> SEQ ID NO 29
<211> LENGTH: 438
<212> TYPE: PRT
<213> ORGANISM: Artificial Sequence
<220> FEATURE:
<223> OTHER INFORMATION: anti-DKK1 Heavy chain (VH + IgG2m4)

<400> SEQUENCE: 29

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile His Ser Asn Ser Gly Ala Thr Thr Tyr Ala Gln Lys Phe
    50                  55                  60
```

Gln Ala Arg Val Thr Met Ser Arg Asp Thr Ser Ser Thr Ala Tyr
65                  70                  75                  80

Met Glu Leu Ser Arg Leu Glu Ser Asp Asp Thr Ala Met Tyr Phe Cys
            85                  90                  95

Ser Arg Glu Asp Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Ser Ser Asn Phe Gly Thr Gln Thr
            180                 185                 190

Tyr Thr Cys Asn Val Asp His Lys Pro Ser Asn Thr Lys Val Asp Lys
            195                 200                 205

Thr Val Glu Arg Lys Cys Cys Val Glu Cys Pro Pro Cys Pro Ala Pro
210                 215                 220

Pro Val Ala Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
            245                 250                 255

Val Ser Gln Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
            275                 280                 285

Ser Thr Phe Arg Val Val Ser Val Leu Thr Val Leu His Gln Asp Trp
            290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Thr Lys Gly Gln Pro Arg Glu
            325                 330                 335

Pro Gln Val Tyr Thr Leu Pro Pro Ser Arg Glu Glu Met Thr Lys Asn
            340                 345                 350

Gln Val Ser Leu Thr Cys Leu Val Lys Gly Phe Tyr Pro Ser Asp Ile
            355                 360                 365

Ala Val Glu Trp Glu Ser Asn Gly Gln Pro Glu Asn Asn Tyr Lys Thr
            370                 375                 380

Thr Pro Pro Met Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
            405                 410                 415

Ser Val Met His Glu Ala Leu His Asn His Tyr Thr Gln Lys Ser Leu
            420                 425                 430

Ser Leu Ser Pro Gly Lys
            435

<210> SEQ ID NO 30
<211> LENGTH: 717
<212> TYPE: DNA
<213> ORGANISM: Artificial Sequence
<220> FEATURE:

<223> OTHER INFORMATION: aanti-DKK1 Light chain (VL + lambda constant
      regions) with alpha-amylase leader

<400> SEQUENCE: 30

```
acgatggtcg cttggtggtc tttgtttctg tacggtcttc aggtcgctgc acctgctttg      60
gctcagtccg ttttgacaca accaccatct gtttctggtg ctccaggaca gagagttact     120
atctcctgta ctggttcctc ttccaacatt ggtgctggtt acgatgttca ctggtatcaa     180
cagttgccag gtactgctcc aaagttgttg atctacggtt actccaacag accatctggt     240
gttccagaca gattctctgg ttctaagtct ggtgcttctg cttccttggc tatcactgga     300
ttgagaccag atgacgaggc tgactactac tgtcaatcct acgacaactc cttgtcctct     360
tacgttttcg gtggtggtac tcagttgact gttttgtccc agccaaaggc taatccaact     420
gttactttgt tcccaccatc ttccgaagaa ctgcaggcta ataaggctac tttggtttgt     480
ttgatctccg acttctaccc aggtgctgtt actgttgctt ggaaggctga tggttctcca     540
gttaaggctg gtgttgagac tactaagcca tccaagcagt ccaataacaa gtacgctgct     600
agctcttact gtccttgac accagaacaa tggaagtccc acagatccta ctcttgtcag     660
gttacacacg agggttctac tgttgaaaag actgttgctc aactgagtg ttcctaa        717
```

<210> SEQ ID NO 31
<211> LENGTH: 217
<212> TYPE: PRT
<213> ORGANISM: Artificial Sequence
<220> FEATURE:
<223> OTHER INFORMATION: aanti-DKK1 Light chain (VL + lambda constant
      regions)

<400> SEQUENCE: 31

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Tyr Ser Asn Arg Pro Ser Gly Val Pro Asp Arg Phe
    50                  55                  60

Ser Gly Ser Lys Ser Gly Ala Ser Ala Ser Leu Ala Ile Thr Gly Leu
65                  70                  75                  80

Arg Pro Asp Asp Glu Ala Asp Tyr Tyr Cys Gln Ser Tyr Asp Asn Ser
                85                  90                  95

Leu Ser Ser Tyr Val Phe Gly Gly Gly Thr Gln Leu Thr Val Leu Ser
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

```
Lys Thr Val Ala Pro Thr Glu Cys Ser
    210                 215

<210> SEQ ID NO 32
<211> LENGTH: 254
<212> TYPE: DNA
<213> ORGANISM: Artificial Sequence
<220> FEATURE:
<223> OTHER INFORMATION: Pichia pastoris PDI1 promoter

<400> SEQUENCE: 32
aacacgaaca ctgtaaatag aataaaagaa aacttggata gtagaacttc aatgtagtgt      60
ttctattgtc ttacgcggct ctttagattg caatccccag aatggaatcg tccatctttc     120
tcaacccact caaagataat ctaccagaca tacctacgcc ctccatccca gcaccacgtc     180
gcgatcaccc ctaaaacttc aataattgaa cacgtactga tttccaaacc ttcttcttct     240
tcctatctat aaga                                                       254

<210> SEQ ID NO 33
<211> LENGTH: 2775
<212> TYPE: DNA
<213> ORGANISM: Pichia pastoris

<400> SEQUENCE: 33
atgacagcta atgaaaatcc ttttgagaat gagctgacag gatcttctga atctgccccc      60
cctgcattgg aatcgaagac tggagagtct cttaagtatt gcaaatatac cgtggatcag     120
gtcatagaag agtttcaaac ggatggtctc aaaggattgt gcaattccca ggacatcgta     180
tatcggaggt ctgttcatgg gccaaatgaa atggaagtcg aagaggaaga gagtcttttt     240
tcgaaattct tgtcaagttt ctacagcgat ccattgattc tgttactgat gggttccgct     300
gtgattagct ttttgatgtc taacattgat gatgcgatat ctatcactat ggcaattacg     360
atcgttgtca cagttggatt tgttcaagag tatcgatccg agaaatcatt ggaggcattg     420
aacaagttag tccctgccga agctcatcta actaggaatg ggaacactga aactgttctt     480
gctgccaacc tagtcccagg agacttggtg gattttttcgg ttggtgacag aattccggct     540
gatgtgagaa ttattcacgc ttcccacttg agtatcgacg agagcaaccct aactggtgaa     600 aatgaaccag tttctaaaga cagcaaaacct gttgaaagtg atgacccaaa cattcccttg     660
aacagccgtt catgtattgg gtatatgggc actttagttc gtgatggtaa tgcaaaggt      720 attgtcatcg aacagccaa aaacacagct tttggctctg ttttcgaaat gatgagctct     780
attgagaaac aaagactcc tcttcaacag gctatggata acttggtaa ggatttgtct     840 gcttttttcct tcggaatcat cggccttatt tgcttggttg gtgtttttca aggtagaccc     900
tggttggaaa tgttccagat ctctgtatcc ttggctgttg ctgcgattcc agaaggtctt     960
cctattattg tgactgtgac tcttgctctt ggtgtgttgc gtatggctaa acagagggcc    1020
atcgtcaaaa gactgcctag tgttgaaact ttgggatccg tcaatgttat ctgtagtgat    1080
aagacgggaa cattgacccca aaatcatatg accgttaaca gattatggac tgtggatatg    1140
ggcgatgaat tcttgaaaat tgaacaaggg gagtcctatg ccaattatct caaacccgat    1200
acgctaaaag ttctgcaaac tggtaatata gtcaacaatg ccaaatattc aaatgaaaag    1260
gaaaaatacc tcggaaaccc aactgatatt gcaattattg aatctttaga aaaatttgat    1320
ttgcaggaca ttagagcaac aaaggaaaga atgttggaga ttccattttc ttcgtccaag    1380
aaatatcagg ccgtcagtgt tcactctgga gacaaaagca aatctgaaat tttgttaaa    1440
```

| | | |
|---|---|---|
| ggcgctctga caaagttttt ggaaagatgt tcaagatatt acaatgctga aggtatcgcc | 1500 | |
| actccactca cagatgaaat tagaagaaaa tccttgcaaa tggccgatac gttagcatct | 1560 | |
| tcaggattga gaatactgtc gtttgcttac gacaaaggca atttttgaaga aactggcgat | 1620 | |
| ggaccatcgg atatgatctt tgtggtctt ttaggtatga cgatcctcc tagaccatct | 1680 | |
| gtaagtaaat caattttgaa attcatgaga ggtggggttc acattattat gattacagga | 1740 | |
| gattcagaat ccacggccgt agccgttgcc aaacaggtcg gaatggtaat tgacaattca | 1800 | |
| aaatatgctg tcctcagtgg agacgatata gatgctatga gtacagagca actgtctcag | 1860 | |
| gcgatctcac attgttctgt atttgcccgg actactccaa acataaggt gtccattgta | 1920 | |
| agagcactac aggccagagg agatattgtt gcaatgactg gtgacggtgt caatgatgcc | 1980 | |
| ccagctctaa aactggccga catcggaatt gccatgggta atatggggac cgatgttgcc | 2040 | |
| aaagaggcag ccgacatggt tttgactgat gatgactttt ctacaatctt atctgcaatc | 2100 | |
| caggagggta aagtatttt ctacaacatc cagaactttt taacgttcca actttctact | 2160 | |
| tcaattgctg ctctttcgtt aattgctctg agtactgctt tcaacctgcc aaatccattg | 2220 | |
| aatgccatgc agattttgtg gatcaatatt atcatggatg gacctccagc tcagtctttg | 2280 | |
| ggtgttgagc cagttgataa agctgtgatg aacaaaccac caagaaagcg aaatgataaa | 2340 | |
| attctgacag gtaaggtgat tcaaagggta gtacaaagta gttttatcat tgtttgtggt | 2400 | |
| actctgtacg tatacatgca tgagatcaaa gataatgagg tcacagcaag agacactacg | 2460 | |
| atgacctta catgctttgt attctttgac atgttcaacg cattaacgac aagacaccat | 2520 | |
| tctaaaagta ttgcagaact tggatggaat aatactatgt tcaacttttc cgttgcagct | 2580 | |
| tctattttgg gtcaactagg agctatttac attccatttt tgcagtctat tttccagact | 2640 | |
| gaacctctga gcctcaaaga tttggtccat ttattgttgt tatcgagttc agtatggatt | 2700 | |
| gtagacgagc ttcgaaaact ctacgtcagg agacgtgacg catccccata caatggatac | 2760 | |
| agcatggctg tttga | 2775 | |

<210> SEQ ID NO 34
<211> LENGTH: 924
<212> TYPE: PRT
<213> ORGANISM: Pichia pastoris

<400> SEQUENCE: 34

Met Thr Ala Asn Glu Asn Pro Phe Glu Asn Glu Leu Thr Gly Ser Ser
1               5                   10                  15

Glu Ser Ala Pro Pro Ala Leu Glu Ser Lys Thr Gly Glu Ser Leu Lys
            20                  25                  30

Tyr Cys Lys Tyr Thr Val Asp Gln Val Ile Glu Glu Phe Gln Thr Asp
        35                  40                  45

Gly Leu Lys Gly Leu Cys Asn Ser Gln Asp Ile Val Tyr Arg Arg Ser
    50                  55                  60

Val His Gly Pro Asn Glu Met Glu Val Glu Glu Glu Ser Leu Phe
65                  70                  75                  80

Ser Lys Phe Leu Ser Ser Phe Tyr Ser Asp Pro Leu Ile Leu Leu Leu
                85                  90                  95

Met Gly Ser Ala Val Ile Ser Phe Leu Met Ser Asn Ile Asp Asp Ala
            100                 105                 110

Ile Ser Ile Thr Met Ala Ile Thr Ile Val Val Thr Val Gly Phe Val
        115                 120                 125

Gln Glu Tyr Arg Ser Glu Lys Ser Leu Glu Ala Leu Asn Lys Leu Val

-continued

```
            130                 135                 140
Pro Ala Glu Ala His Leu Thr Arg Asn Gly Asn Thr Glu Thr Val Leu
145                 150                 155                 160

Ala Ala Asn Leu Val Pro Gly Asp Leu Val Asp Phe Ser Val Gly Asp
                165                 170                 175

Arg Ile Pro Ala Asp Val Arg Ile Ile His Ala Ser His Leu Ser Ile
            180                 185                 190

Asp Glu Ser Asn Leu Thr Gly Glu Asn Glu Pro Val Ser Lys Asp Ser
        195                 200                 205

Lys Pro Val Glu Ser Asp Asp Pro Asn Ile Pro Leu Asn Ser Arg Ser
210                 215                 220

Cys Ile Gly Tyr Met Gly Thr Leu Val Arg Asp Gly Asn Gly Lys Gly
225                 230                 235                 240

Ile Val Ile Gly Thr Ala Lys Asn Thr Ala Phe Gly Ser Val Phe Glu
                245                 250                 255

Met Met Ser Ser Ile Glu Lys Pro Lys Thr Pro Leu Gln Gln Ala Met
                260                 265                 270

Asp Lys Leu Gly Lys Asp Leu Ser Ala Phe Ser Phe Gly Ile Ile Gly
        275                 280                 285

Leu Ile Cys Leu Val Gly Val Phe Gln Gly Arg Pro Trp Leu Glu Met
290                 295                 300

Phe Gln Ile Ser Val Ser Leu Ala Val Ala Ala Ile Pro Glu Gly Leu
305                 310                 315                 320

Pro Ile Ile Val Thr Val Thr Leu Ala Leu Gly Val Leu Arg Met Ala
                325                 330                 335

Lys Gln Arg Ala Ile Val Lys Arg Leu Pro Ser Val Glu Thr Leu Gly
                340                 345                 350

Ser Val Asn Val Ile Cys Ser Asp Lys Thr Gly Thr Leu Thr Gln Asn
        355                 360                 365

His Met Thr Val Asn Arg Leu Trp Thr Val Asp Met Gly Asp Glu Phe
370                 375                 380

Leu Lys Ile Glu Gln Gly Glu Ser Tyr Ala Asn Tyr Leu Lys Pro Asp
385                 390                 395                 400

Thr Leu Lys Val Leu Gln Thr Gly Asn Ile Val Asn Asn Ala Lys Tyr
                405                 410                 415

Ser Asn Glu Lys Glu Lys Tyr Leu Gly Asn Pro Thr Asp Ile Ala Ile
                420                 425                 430

Ile Glu Ser Leu Glu Lys Phe Asp Leu Gln Asp Ile Arg Ala Thr Lys
        435                 440                 445

Glu Arg Met Leu Glu Ile Pro Phe Ser Ser Lys Lys Tyr Gln Ala
450                 455                 460

Val Ser Val His Ser Gly Asp Lys Ser Lys Ser Glu Ile Phe Val Lys
465                 470                 475                 480

Gly Ala Leu Asn Lys Val Leu Glu Arg Cys Ser Arg Tyr Tyr Asn Ala
                485                 490                 495

Glu Gly Ile Ala Thr Pro Leu Thr Asp Glu Ile Arg Arg Lys Ser Leu
                500                 505                 510

Gln Met Ala Asp Thr Leu Ala Ser Ser Gly Leu Arg Ile Leu Ser Phe
        515                 520                 525

Ala Tyr Asp Lys Gly Asn Phe Glu Glu Thr Gly Asp Gly Pro Ser Asp
530                 535                 540

Met Ile Phe Cys Gly Leu Leu Gly Met Asn Asp Pro Pro Arg Pro Ser
545                 550                 555                 560
```

Val Ser Lys Ser Ile Leu Lys Phe Met Arg Gly Val His Ile Ile
                565                 570                 575

Met Ile Thr Gly Asp Ser Glu Ser Thr Ala Val Ala Val Ala Lys Gln
            580                 585                 590

Val Gly Met Val Ile Asp Asn Ser Lys Tyr Ala Val Leu Ser Gly Asp
        595                 600                 605

Asp Ile Asp Ala Met Ser Thr Glu Gln Leu Ser Gln Ala Ile Ser His
    610                 615                 620

Cys Ser Val Phe Ala Arg Thr Thr Pro Lys His Lys Val Ser Ile Val
625                 630                 635                 640

Arg Ala Leu Gln Ala Arg Gly Asp Ile Val Ala Met Thr Gly Asp Gly
                645                 650                 655

Val Asn Asp Ala Pro Ala Leu Lys Leu Ala Asp Ile Gly Ile Ala Met
            660                 665                 670

Gly Asn Met Gly Thr Asp Val Ala Lys Glu Ala Ala Asp Met Val Leu
        675                 680                 685

Thr Asp Asp Asp Phe Ser Thr Ile Leu Ser Ala Ile Gln Glu Gly Lys
    690                 695                 700

Gly Ile Phe Tyr Asn Ile Gln Asn Phe Leu Thr Phe Gln Leu Ser Thr
705                 710                 715                 720

Ser Ile Ala Ala Leu Ser Leu Ile Ala Leu Ser Thr Ala Phe Asn Leu
                725                 730                 735

Pro Asn Pro Leu Asn Ala Met Gln Ile Leu Trp Ile Asn Ile Ile Met
            740                 745                 750

Asp Gly Pro Pro Ala Gln Ser Leu Gly Val Glu Pro Val Asp Lys Ala
        755                 760                 765

Val Met Asn Lys Pro Pro Arg Lys Arg Asn Asp Lys Ile Leu Thr Gly
    770                 775                 780

Lys Val Ile Gln Arg Val Val Gln Ser Ser Phe Ile Ile Val Cys Gly
785                 790                 795                 800

Thr Leu Tyr Val Tyr Met His Glu Ile Lys Asp Asn Glu Val Thr Ala
                805                 810                 815

Arg Asp Thr Thr Met Thr Phe Thr Cys Phe Val Phe Phe Asp Met Phe
            820                 825                 830

Asn Ala Leu Thr Thr Arg His His Ser Lys Ser Ile Ala Glu Leu Gly
        835                 840                 845

Trp Asn Asn Thr Met Phe Asn Phe Ser Val Ala Ala Ser Ile Leu Gly
    850                 855                 860

Gln Leu Gly Ala Ile Tyr Ile Pro Phe Leu Gln Ser Ile Phe Gln Thr
865                 870                 875                 880

Glu Pro Leu Ser Leu Lys Asp Leu Val His Leu Leu Leu Leu Ser Ser
                885                 890                 895

Ser Val Trp Ile Val Asp Glu Leu Arg Lys Leu Tyr Val Arg Arg Arg
            900                 905                 910

Asp Ala Ser Pro Tyr Asn Gly Tyr Ser Met Ala Val
        915                 920

<210> SEQ ID NO 35
<211> LENGTH: 3186
<212> TYPE: DNA
<213> ORGANISM: Artificial Sequence
<220> FEATURE:
<223> OTHER INFORMATION: Arabidopsis thalian DNA encoding ECA1
      codon-optimized for Pichia expression

<400> SEQUENCE: 35

```
atgggaaagg gttccgagga cctggttaag aaagaatccc tgaactccac tccagttaac    60
tctgacactt tcccagcttg ggctaaggat gttgctgagt gcgaagagca cttcgttgtt   120
tccagagaga agggtttgtc ctccgacgaa gtcttgaaga gaccaaat ctacggactg    180
aacgagttgg aaaagccaga gggaacctcc atcttcaagc tgatcttgga gcagttcaac   240
gacacccttg tcagaatttt gttggctgcc gctgttattt ccttcgtcct ggctttttt    300
gatggtgacg agggtggtga atgggtatc actgccttcg ttgagccttt ggtcatcttc    360
ctgatcttga tcgttaacgc catcgttggt atctggcaag agactaacgc tgaaaaggct   420
ttggaggcct tgaaagagat tcaatcccag caggctaccg ttatgagaga tggtactaag   480
gtttcctcct tgccagctaa agaattggtt ccaggtgaca tcgttgagct gagagttggt   540
gataaggttc cagccgacat gagagttgtt gctttgatct cctccaccttt gagagttgaa  600
caaggttccc tgactggtga atctgaggct gtttccaaga ctactaagca cgttgacgag   660
aacgctgaca tccagggtaa aaagtgcatg gttttcgccg gtactaccgt tgttaacggt   720
aactgcatct gtttggtcac tgacactgga atgaacaccg gatcggtag agttcactcc    780
caaatccaag aagctgctca acacgaagag gacacccat tgaagaagaa gctgaacgag   840
ttcggagagg tcttgaccat gatcatcgga ttgatctgtg ccctggtctg gttgatcaac   900
gtcaagtact tcttgtcctg ggaatacgtt gatggatggc caagaaactt caagttctcc   960
ttcgagaagt gcacctacta cttcgagatc gctgttgctt tggctgttgc tgctattcca  1020
gagggattgc cagctgttat caccacttgc ttggccttgg gtactagaaa gatggctcag  1080
aagaacgccc ttgttagaaa gttgccatcc gttgagactt tgggttgtac taccgtcatc  1140
tgttccgaca agactggtac tttgactacc aaccagatgg ccgttccaa attggttgcc   1200
atgggttcca gaatcggtac tctgagatcc ttcaacgtcg agggaacttc ttttgaccca  1260
agagatggaa agattgagga ctggccaatg ggtagaatgg acgccaactt gcagatgatt  1320
gctaagatcg ccgctatctg taacgacgct aacgttgagc aatccgacca acagttcgtt  1380
tccagaggaa tgccaactga ggctgccttg aaggttttgg tcgagaagat gggtttccca  1440
gaaggattga acgaggcttc ttccgatggt gacgtcttga gatgttgcag actgtggagt  1500
gagttggagc agagaatcgc tactttggag ttcgacagag atagaaagtc catgggtgtc  1560
atggttgatt cttcctccgg taacaagttg ttgttggtca aaggagcagt tgaaaacgtt  1620
ttggagagat ccacccacat tcaattgctg gacggttcca agagagaatt ggaccagtac  1680
tccagagact tgatcttgca gtccttgaga gacatgtcct tgtccgcctt gagatgtttg  1740
ggtttcgctt actctgacgt tccatccgat ttcgctactt acgatggttc tgaggatcat  1800
ccagctcacc aacagttgct gaacccatcc aactactcct ccatcgaatc caacctgatc  1860
ttcgttggtt tcgtcggtct tagagaccca ccaagaaaag aagttagaca ggccatcgct  1920
gattgtagaa ccgccggtat cagagttatg gtcatcaccg gagataacaa gtccactgcc  1980
gaggctattt gtagagagat cggagttttc gaggctgacg aggacatttc ttccagatcc  2040
ctgaccggta ttgagttcat ggacgtccaa gaccagaaga accacttgag acagaccggt  2100
ggtttgttgt tctccagagc cgaaccaaag cacaagcaag agattgtcag actgctgaaa  2160
gaggacggag aagttgttgc tatgaccggt gatggtgtta atgacgcccc agcttttgaag  2220
ttggctgaca tcggtgttgc tatgggaatt tccggtacta agttgctaa ggaagcctcc   2280
gatatggttt tggctgacga caacttttca actatcgttg ctgctgtcgg agaaggtaga  2340
```

-continued

```
agtatctaca acaacatgaa agcctttatc agatacatga tttcctccaa catcggtgaa      2400
gttgcctcca ttttcttgac tgctgccttg ggtattcctg agggaatgat cccagttcag      2460
ttgttgtggg ttaacttggt tactgacggt ccacctgcta ctgctttggg tttcaaccca      2520
ccagacaaag acattatgaa gaagccacca agaagatccg acgattcctt gatcaccgcc      2580
tggatcttgt tcagatacat ggtcatcggt ctttatgttg gtgttgccac cgtcggtgtt      2640
ttcatcatct ggtacaccca ctcttccttc atgggtattg acttgtctca agatggtcat      2700
tctttggttt cctactccca attggctcat ggggacaat gttcttcctg ggagggtttc       2760
aaggtttccc cattcactgc tggttcccag actttctcct tcgattccaa cccatgtgac      2820
tacttccagc agggaaagat caaggcttcc accttgtctt tgtccgtttt ggtcgccatt      2880
gagatgttca actccctgaa cgctttgtct gaggacggtt ccttggttac tatgccacct      2940
tgggtgaacc catggttgtt gttggctatg gctgtttcct tcggattgca cttcgtcatc      3000
ctgtacgttc cattcttggc ccaggttttc ggtattgttc cactgtcctt gaacgagtgg      3060
ttgttggtct tggccgtttc tttgccagtt atcctgatcg acgaggtttt gaagttcgtt      3120
ggtagatgca cctctggtta cagatactcc ccaagaactc tgtccaccaa gcagaaagaa      3180
gagtaa                                                                  3186
```

<210> SEQ ID NO 36
<211> LENGTH: 1061
<212> TYPE: PRT
<213> ORGANISM: Arabidopsis thaliana

<400> SEQUENCE: 36

```
Met Gly Lys Gly Ser Glu Asp Leu Val Lys Lys Glu Ser Leu Asn Ser
1               5                   10                  15

Thr Pro Val Asn Ser Asp Thr Phe Pro Ala Trp Ala Lys Asp Val Ala
            20                  25                  30

Glu Cys Glu Glu His Phe Val Val Ser Arg Glu Lys Gly Leu Ser Ser
        35                  40                  45

Asp Glu Val Leu Lys Arg His Gln Ile Tyr Gly Leu Asn Glu Leu Glu
    50                  55                  60

Lys Pro Glu Gly Thr Ser Ile Phe Lys Leu Ile Leu Glu Gln Phe Asn
65                  70                  75                  80

Asp Thr Leu Val Arg Ile Leu Leu Ala Ala Ala Val Ile Ser Phe Val
                85                  90                  95

Leu Ala Phe Phe Asp Gly Asp Glu Gly Gly Glu Met Gly Ile Thr Ala
            100                 105                 110

Phe Val Glu Pro Leu Val Ile Phe Leu Ile Leu Ile Val Asn Ala Ile
        115                 120                 125

Val Gly Ile Trp Gln Glu Thr Asn Ala Glu Lys Ala Leu Glu Ala Leu
    130                 135                 140

Lys Glu Ile Gln Ser Gln Gln Ala Thr Val Met Arg Asp Gly Thr Lys
145                 150                 155                 160

Val Ser Ser Leu Pro Ala Lys Glu Leu Val Pro Gly Asp Ile Val Glu
                165                 170                 175

Leu Arg Val Gly Asp Lys Val Pro Ala Asp Met Arg Val Val Ala Leu
            180                 185                 190

Ile Ser Ser Thr Leu Arg Val Glu Gln Gly Ser Leu Thr Gly Glu Ser
        195                 200                 205

Glu Ala Val Ser Lys Thr Thr Lys His Val Asp Glu Asn Ala Asp Ile
```

-continued

```
            210                 215                 220
Gln Gly Lys Lys Cys Met Val Phe Ala Gly Thr Thr Val Val Asn Gly
225                 230                 235                 240

Asn Cys Ile Cys Leu Val Thr Asp Thr Gly Met Asn Thr Glu Ile Gly
                    245                 250                 255

Arg Val His Ser Gln Ile Gln Glu Ala Ala Gln His Glu Glu Asp Thr
                260                 265                 270

Pro Leu Lys Lys Lys Leu Asn Glu Phe Gly Glu Val Leu Thr Met Ile
            275                 280                 285

Ile Gly Leu Ile Cys Ala Leu Val Trp Leu Ile Asn Val Lys Tyr Phe
290                 295                 300

Leu Ser Trp Glu Tyr Val Asp Gly Trp Pro Arg Asn Phe Lys Phe Ser
305                 310                 315                 320

Phe Glu Lys Cys Thr Tyr Tyr Phe Glu Ile Ala Val Ala Leu Ala Val
                325                 330                 335

Ala Ala Ile Pro Glu Gly Leu Pro Ala Val Ile Thr Thr Cys Leu Ala
                340                 345                 350

Leu Gly Thr Arg Lys Met Ala Gln Lys Asn Ala Leu Val Arg Lys Leu
            355                 360                 365

Pro Ser Val Glu Thr Leu Gly Cys Thr Thr Val Ile Cys Ser Asp Lys
            370                 375                 380

Thr Gly Thr Leu Thr Thr Asn Gln Met Ala Val Ser Lys Leu Val Ala
385                 390                 395                 400

Met Gly Ser Arg Ile Gly Thr Leu Arg Ser Phe Asn Val Glu Gly Thr
                    405                 410                 415

Ser Phe Asp Pro Arg Asp Gly Lys Ile Glu Asp Trp Pro Met Gly Arg
                420                 425                 430

Met Asp Ala Asn Leu Gln Met Ile Ala Lys Ile Ala Ala Ile Cys Asn
                435                 440                 445

Asp Ala Asn Val Glu Gln Ser Asp Gln Gln Phe Val Ser Arg Gly Met
                450                 455                 460

Pro Thr Glu Ala Ala Leu Lys Val Leu Val Glu Lys Met Gly Phe Pro
465                 470                 475                 480

Glu Gly Leu Asn Glu Ala Ser Ser Asp Gly Asp Val Leu Arg Cys Cys
                    485                 490                 495

Arg Leu Trp Ser Glu Leu Glu Gln Arg Ile Ala Thr Leu Glu Phe Asp
                500                 505                 510

Arg Asp Arg Lys Ser Met Gly Val Met Val Asp Ser Ser Ser Gly Asn
                515                 520                 525

Lys Leu Leu Leu Val Lys Gly Ala Val Glu Asn Val Leu Glu Arg Ser
            530                 535                 540

Thr His Ile Gln Leu Leu Asp Gly Ser Lys Arg Glu Leu Asp Gln Tyr
545                 550                 555                 560

Ser Arg Asp Leu Ile Leu Gln Ser Leu Arg Asp Met Ser Leu Ser Ala
                    565                 570                 575

Leu Arg Cys Leu Gly Phe Ala Tyr Ser Asp Val Pro Ser Asp Phe Ala
                580                 585                 590

Thr Tyr Asp Gly Ser Glu Asp His Pro Ala His Gln Leu Leu Asn
                595                 600                 605

Pro Ser Asn Tyr Ser Ser Ile Glu Ser Asn Leu Ile Phe Val Gly Phe
            610                 615                 620

Val Gly Leu Arg Asp Pro Pro Arg Lys Glu Val Arg Gln Ala Ile Ala
625                 630                 635                 640
```

-continued

```
Asp Cys Arg Thr Ala Gly Ile Arg Val Met Val Ile Thr Gly Asp Asn
            645                 650                 655
Lys Ser Thr Ala Glu Ala Ile Cys Arg Glu Ile Gly Val Phe Glu Ala
            660                 665                 670
Asp Glu Asp Ile Ser Ser Arg Ser Leu Thr Gly Ile Glu Phe Met Asp
            675                 680                 685
Val Gln Asp Gln Lys Asn His Leu Arg Gln Thr Gly Gly Leu Leu Phe
            690                 695                 700
Ser Arg Ala Glu Pro Lys His Lys Gln Glu Ile Val Arg Leu Leu Lys
705                 710                 715                 720
Glu Asp Gly Glu Val Val Ala Met Thr Gly Asp Gly Val Asn Asp Ala
                725                 730                 735
Pro Ala Leu Lys Leu Ala Asp Ile Gly Val Ala Met Gly Ile Ser Gly
                740                 745                 750
Thr Glu Val Ala Lys Glu Ala Ser Asp Met Val Leu Ala Asp Asp Asn
                755                 760                 765
Phe Ser Thr Ile Val Ala Ala Val Gly Glu Gly Arg Ser Ile Tyr Asn
            770                 775                 780
Asn Met Lys Ala Phe Ile Arg Tyr Met Ile Ser Ser Asn Ile Gly Glu
785                 790                 795                 800
Val Ala Ser Ile Phe Leu Thr Ala Ala Leu Gly Ile Pro Glu Gly Met
                805                 810                 815
Ile Pro Val Gln Leu Leu Trp Val Asn Leu Val Thr Asp Gly Pro Pro
                820                 825                 830
Ala Thr Ala Leu Gly Phe Asn Pro Pro Asp Lys Asp Ile Met Lys Lys
                835                 840                 845
Pro Pro Arg Arg Ser Asp Asp Ser Leu Ile Thr Ala Trp Ile Leu Phe
                850                 855                 860
Arg Tyr Met Val Ile Gly Leu Tyr Val Gly Val Ala Thr Val Gly Val
865                 870                 875                 880
Phe Ile Ile Trp Tyr Thr His Ser Ser Phe Met Gly Ile Asp Leu Ser
            885                 890                 895
Gln Asp Gly His Ser Leu Val Ser Tyr Ser Gln Leu Ala His Trp Gly
            900                 905                 910
Gln Cys Ser Ser Trp Glu Gly Phe Lys Val Ser Pro Phe Thr Ala Gly
            915                 920                 925
Ser Gln Thr Phe Ser Phe Asp Ser Asn Pro Cys Asp Tyr Phe Gln Gln
            930                 935                 940
Gly Lys Ile Lys Ala Ser Thr Leu Ser Leu Ser Val Leu Val Ala Ile
945                 950                 955                 960
Glu Met Phe Asn Ser Leu Asn Ala Leu Ser Glu Asp Gly Ser Leu Val
                965                 970                 975
Thr Met Pro Pro Trp Val Asn Pro Trp Leu Leu Leu Ala Met Ala Val
                980                 985                 990
Ser Phe Gly Leu His Phe Val Ile Leu Tyr Val Pro Phe Leu Ala Gln
            995                 1000                1005
Val Phe Gly Ile Val Pro Leu Ser Leu Asn Glu Trp Leu Leu Val
            1010                1015                1020
Leu Ala Val Ser Leu Pro Val Ile Leu Ile Asp Glu Val Leu Lys
            1025                1030                1035
Phe Val Gly Arg Cys Thr Ser Gly Tyr Arg Tyr Ser Pro Arg Thr
            1040                1045                1050
```

Leu Ser Thr Lys Gln Lys Glu Glu
1055            1060

```
<210> SEQ ID NO 37
<211> LENGTH: 39
<212> TYPE: DNA
<213> ORGANISM: Artificial Sequence
<220> FEATURE:
<223> OTHER INFORMATION: PpPMR1/UP PCR primer

<400> SEQUENCE: 37
gaattcatga cagctaatga aaatccttttt gagaatgag                        39

<210> SEQ ID NO 38
<211> LENGTH: 37
<212> TYPE: DNA
<213> ORGANISM: Artificial Sequence
<220> FEATURE:
<223> OTHER INFORMATION: PpPMR1/LP PCR primer

<400> SEQUENCE: 38
ggccggcctc aaacagccat gctgtatcca ttgtatg                           37

<210> SEQ ID NO 39
<211> LENGTH: 25
<212> TYPE: DNA
<213> ORGANISM: Artificial Sequence
<220> FEATURE:
<223> OTHER INFORMATION: 5'AOX1 PCR primer

<400> SEQUENCE: 39
gcgactggtt ccaattgaca agctt                                        25

<210> SEQ ID NO 40
<211> LENGTH: 30
<212> TYPE: DNA
<213> ORGANISM: Artificial Sequence
<220> FEATURE:
<223> OTHER INFORMATION: PpPMR1/cLP PCR primer

<400> SEQUENCE: 40
ggttgctctc gtcgatactc aagtgggaag                                   30

<210> SEQ ID NO 41
<211> LENGTH: 30
<212> TYPE: DNA
<213> ORGANISM: Artificial Sequence
<220> FEATURE:
<223> OTHER INFORMATION: AtECA1/cLP PCR primer

<400> SEQUENCE: 41
gtcggctgga accttatcac caactctcag                                   30

<210> SEQ ID NO 42
<211> LENGTH: 1314
<212> TYPE: DNA
<213> ORGANISM: Homo sapiens

<400> SEQUENCE: 42
atgagatttc cttcaatttt tactgctgtt ttattcgcag catcctccgc attagcttac   60
ccatacgacg tcccagacta cgcttaccca tacgacgtcc cagactacgc tgagcccgcc  120
gtctacttca aggagcagtt tctggacgga gacgggtgga cttccgctg atcgaatcc    180 aaacacaagt cagattttgg caaattcgtt ctcagttccg gcaagttcta cggtgacgag  240
```

-continued

```
gagaaagata aaggtttgca gacaagccag gatgcacgct ttatgctct gtcggccagt    300 ttcgagcctt tcagcaacaa aggccagacg ctggtggtgc agttcacggt gaaacatgag    360
cagaacatcg actgtggggg cggctatgtg aagctgtttc ctaatagttt ggaccagaca    420
gacatgcacg gagactcaga atacaacatc atgtttggtc ccgacatctg tggccctggc    480
accaagaagg ttcatgtcat cttcaactac aagggcaaga acgtgctgat caacaaggac    540
atccgttgca aggatgatga gtttacacac ctgtacacac tgattgtgcg gccagacaac    600
acctatgagg tgaagattga acacagccag gtggagtccg gctccttgga agacgattgg    660
gacttcctgc cacccaagaa gataaaggat cctgatgctt caaaaccgga agactgggat    720
gagcgggcca agatcgatga tcccacagac tccaagcctg aggactggga caagcccgag    780
catatccctg accctgatgc taagaagccc gaggactggg atgaagagat ggacggagag    840
tgggaacccc cagtgattca gaaccctgag tacaagggtg agtggaagcc ccggcagatc    900
gacaacccag attacaaggg cacttggatc cacccagaaa ttgacaaccc cgagtattct    960
cccgatccca gtatctatgc ctatgataac tttggcgtgc tgggcctgga cctctggcag   1020
gtcaagtctg gcaccatctt tgacaacttc ctcatcacca acgatgaggc atacgctgag   1080
gagtttggca cgagacgtg gggcgtaaca aaggcagcag agaaacaaat gaaggacaaa   1140
caggacgagg agcagaggct taaggaggag gaagaagaca agaaacgcaa agaggaggag   1200
gaggcagagg acaaggagga tgatgaggac aaagatgagg atgaggagga tgaggaggac   1260
aaggaggaag atgaggagga agatgtcccc ggccaggccc atgacgagct gtag        1314
```

<210> SEQ ID NO 43
<211> LENGTH: 437
<212> TYPE: PRT
<213> ORGANISM: Artificial Sequence
<220> FEATURE:
<223> OTHER INFORMATION: Human calreticulin (hCRT)-protein with
      Saccharomyces cerevisiae mating factor pre-signal peptide leader

<400> SEQUENCE: 43

```
Met Arg Phe Pro Ser Ile Phe Thr Ala Val Leu Phe Ala Ala Ser Ser
1               5                   10                  15

Ala Leu Ala Tyr Pro Tyr Asp Val Pro Asp Tyr Ala Tyr Pro Tyr Asp
                20                  25                  30

Val Pro Asp Tyr Ala Glu Pro Ala Val Tyr Phe Lys Glu Gln Phe Leu
            35                  40                  45

Asp Gly Asp Gly Trp Thr Ser Arg Trp Ile Glu Ser Lys His Lys Ser
        50                  55                  60

Asp Phe Gly Lys Phe Val Leu Ser Ser Gly Lys Phe Tyr Gly Asp Glu
65                  70                  75                  80

Glu Lys Asp Lys Gly Leu Gln Thr Ser Gln Asp Ala Arg Phe Tyr Ala
                85                  90                  95

Leu Ser Ala Ser Phe Glu Pro Phe Ser Asn Lys Gly Gln Thr Leu Val
            100                 105                 110

Val Gln Phe Thr Val Lys His Glu Gln Asn Ile Asp Cys Gly Gly Gly
        115                 120                 125

Tyr Val Lys Leu Phe Pro Asn Ser Leu Asp Gln Thr Asp Met His Gly
    130                 135                 140

Asp Ser Glu Tyr Asn Ile Met Phe Gly Pro Asp Ile Cys Gly Pro Gly
145                 150                 155                 160

Thr Lys Lys Val His Val Ile Phe Asn Tyr Lys Gly Lys Asn Val Leu
                165                 170                 175
```

Ile Asn Lys Asp Ile Arg Cys Lys Asp Asp Glu Phe Thr His Leu Tyr
            180                 185                 190

Thr Leu Ile Val Arg Pro Asp Asn Thr Tyr Glu Val Lys Ile Asp Asn
            195                 200                 205

Ser Gln Val Glu Ser Gly Ser Leu Glu Asp Asp Trp Asp Phe Leu Pro
210                 215                 220

Pro Lys Lys Ile Lys Asp Pro Asp Ala Ser Lys Pro Glu Asp Trp Asp
225                 230                 235                 240

Glu Arg Ala Lys Ile Asp Asp Pro Thr Asp Ser Lys Pro Glu Asp Trp
                245                 250                 255

Asp Lys Pro Glu His Ile Pro Asp Pro Asp Ala Lys Lys Pro Glu Asp
            260                 265                 270

Trp Asp Glu Glu Met Asp Gly Glu Trp Glu Pro Pro Val Ile Gln Asn
            275                 280                 285

Pro Glu Tyr Lys Gly Glu Trp Lys Pro Arg Gln Ile Asp Asn Pro Asp
            290                 295                 300

Tyr Lys Gly Thr Trp Ile His Pro Glu Ile Asp Asn Pro Glu Tyr Ser
305                 310                 315                 320

Pro Asp Pro Ser Ile Tyr Ala Tyr Asp Asn Phe Gly Val Leu Gly Leu
                325                 330                 335

Asp Leu Trp Gln Val Lys Ser Gly Thr Ile Phe Asp Asn Phe Leu Ile
            340                 345                 350

Thr Asn Asp Glu Ala Tyr Ala Glu Glu Phe Gly Asn Glu Thr Trp Gly
            355                 360                 365

Val Thr Lys Ala Ala Glu Lys Gln Met Lys Asp Lys Gln Asp Glu Glu
            370                 375                 380

Gln Arg Leu Lys Glu Glu Glu Asp Lys Lys Arg Lys Glu Glu Glu Glu
385                 390                 395                 400

Glu Ala Glu Asp Lys Glu Asp Asp Glu Asp Lys Asp Glu Asp Glu Glu
                405                 410                 415

Asp Glu Glu Asp Lys Glu Glu Asp Glu Glu Glu Asp Val Pro Gly Gln
            420                 425                 430

Ala His Asp Glu Leu
            435

<210> SEQ ID NO 44
<211> LENGTH: 1512
<212> TYPE: DNA
<213> ORGANISM: Homo sapiens

<400> SEQUENCE: 44
atgcaattca actggaacat caagactgtt gcttccatct tgtccgcttt gactttggct      60
caagcttctg acgttttgga gttgactgac gacaacttcg agtccagaat ttctgacact     120
ggttccgctg gattgatgtt ggttgagttc ttcgctccat ggtgtggtca ttgtaagaga     180
ttggctccag aatacgaagc tgctgctact agattgaagg gtatcgttcc attggctaag     240
gttgactgta ctgctaacac taacacttgt aacaagtacg gtgtttccgg ttacccaact     300
ttgaagatct tcagagatgg tgaagaagct ggagcttacg acggtccaag aactgctgac     360
ggtatcgttt cccacttgaa gaagcaagct ggtccagctt ctgttccatt gagaactgag     420
gaggagttca agaagttcat ctccgacaag gacgcttcta cgttggtttt cttcgacgat     480
tctttctctg aagctcactc cgaattcttg aaggctgctt ccaacttgag agacaactac     540
agattcgctc acactaacgt tgagtccttg gttaacgagt acgacgataa cggtgaaggt     600

```
atcatcttgt tcagaccatc ccacttgact aacaagttcg aggacaagac agttgcttac    660
actgagcaga gatgacttc cggaaagatc aagaagttta tccaagagaa catcttcggt    720
atctgtccac acatgactga ggacaacaag gacttgattc agggaaagga cttgttgatc    780
gcttactacg acgttgacta cgagaagaac gctaagggtt ccaactactg gagaaacaga    840
gttatgatgg ttgctaagaa gttcttggac gctggtcaca agttgaactt cgctgttgct    900
tctagaaaga ctttctccca cgagttgtct gatttcggat tggaatccac tgctggagag    960
attccagttg ttgctatcag aactgctaag ggagagaagt tcgttatgca agaggagttc   1020
tccagagatg aaaggctttt ggagagattc ttgcaggatt acttcgacgg taacttgaag   1080
agatacttga agtccgagcc aattccagaa tctaacgacg gtccagttaa agttgttgtt   1140
gctgagaact tcgacgagat cgttaacaac gagaacaagg acgttttgat cgagttttac   1200
gctccttggt gtggacactg taaaaacttg gagccaaagt acaaggaatt gggtgaaaag   1260
ttgtccaagg acccaaacat cgttatcgct aagatggacg ctactgctaa cgatgttcca   1320
tccccatacg aagttagagg tttcccaact atctacttct ccccagctaa caagaagttg   1380
aacccaaaga agtacgaggg aggtagagaa ttgtccgact tcatctccta cttgcagaga   1440
gaggctacta atccaccagt tatccaagag gagaagccaa agaagaagaa gaaagctcac   1500
gacgagttgt ag                                                       1512
```

<210> SEQ ID NO 45
<211> LENGTH: 503
<212> TYPE: PRT
<213> ORGANISM: Homo sapiens

<400> SEQUENCE: 45

```
Met Gln Phe Asn Trp Asn Ile Lys Thr Val Ala Ser Ile Leu Ser Ala
1               5                   10                  15

Leu Thr Leu Ala Gln Ala Ser Asp Val Leu Glu Leu Thr Asp Asp Asn
            20                  25                  30

Phe Glu Ser Arg Ile Ser Asp Thr Gly Ser Ala Gly Leu Met Leu Val
        35                  40                  45

Glu Phe Phe Ala Pro Trp Cys Gly His Cys Lys Arg Leu Ala Pro Glu
    50                  55                  60

Tyr Glu Ala Ala Ala Thr Arg Leu Lys Gly Ile Val Pro Leu Ala Lys
65                  70                  75                  80

Val Asp Cys Thr Ala Asn Thr Asn Thr Cys Asn Lys Tyr Gly Val Ser
                85                  90                  95

Gly Tyr Pro Thr Leu Lys Ile Phe Arg Asp Gly Glu Glu Ala Gly Ala
            100                 105                 110

Tyr Asp Gly Pro Arg Thr Ala Asp Gly Ile Val Ser His Leu Lys Lys
        115                 120                 125

Gln Ala Gly Pro Ala Ser Val Pro Leu Arg Thr Glu Glu Phe Lys
    130                 135                 140

Lys Phe Ile Ser Asp Lys Asp Ala Ser Ile Val Gly Phe Phe Asp Asp
145                 150                 155                 160

Ser Phe Ser Glu Ala His Ser Glu Phe Leu Lys Ala Ala Ser Asn Leu
                165                 170                 175

Arg Asp Asn Tyr Arg Phe Ala His Thr Asn Val Glu Ser Leu Val Asn
            180                 185                 190

Glu Tyr Asp Asp Asn Gly Glu Gly Ile Ile Leu Phe Arg Pro Ser His
        195                 200                 205
```

Leu Thr Asn Lys Phe Glu Asp Lys Thr Val Ala Tyr Thr Glu Gln Lys
    210                 215                 220

Met Thr Ser Gly Lys Ile Lys Lys Phe Ile Gln Glu Asn Ile Phe Gly
225                 230                 235                 240

Ile Cys Pro His Met Thr Glu Asp Asn Lys Asp Leu Ile Gln Gly Lys
                245                 250                 255

Asp Leu Leu Ile Ala Tyr Tyr Asp Val Asp Tyr Glu Lys Asn Ala Lys
            260                 265                 270

Gly Ser Asn Tyr Trp Arg Asn Arg Val Met Met Val Ala Lys Lys Phe
        275                 280                 285

Leu Asp Ala Gly His Lys Leu Asn Phe Ala Val Ala Ser Arg Lys Thr
    290                 295                 300

Phe Ser His Glu Leu Ser Asp Phe Gly Leu Glu Ser Thr Ala Gly Glu
305                 310                 315                 320

Ile Pro Val Val Ala Ile Arg Thr Ala Lys Gly Glu Lys Phe Val Met
                325                 330                 335

Gln Glu Glu Phe Ser Arg Asp Gly Lys Ala Leu Glu Arg Phe Leu Gln
            340                 345                 350

Asp Tyr Phe Asp Gly Asn Leu Lys Arg Tyr Leu Lys Ser Glu Pro Ile
        355                 360                 365

Pro Glu Ser Asn Asp Gly Pro Val Lys Val Val Ala Glu Asn Phe
    370                 375                 380

Asp Glu Ile Val Asn Asn Glu Asn Lys Asp Val Leu Ile Glu Phe Tyr
385                 390                 395                 400

Ala Pro Trp Cys Gly His Cys Lys Asn Leu Pro Lys Tyr Lys Glu
                405                 410                 415

Leu Gly Glu Lys Leu Ser Lys Asp Pro Asn Ile Val Ile Ala Lys Met
            420                 425                 430

Asp Ala Thr Ala Asn Asp Val Pro Ser Pro Tyr Glu Val Arg Gly Phe
        435                 440                 445

Pro Thr Ile Tyr Phe Ser Pro Ala Asn Lys Lys Leu Asn Pro Lys Lys
    450                 455                 460

Tyr Glu Gly Gly Arg Glu Leu Ser Asp Phe Ile Ser Tyr Leu Gln Arg
465                 470                 475                 480

Glu Ala Thr Asn Pro Pro Val Ile Gln Glu Glu Lys Pro Lys Lys Lys
                485                 490                 495

Lys Lys Ala His Asp Glu Leu
            500

<210> SEQ ID NO 46
<211> LENGTH: 55
<212> TYPE: DNA
<213> ORGANISM: Artificial Sequence
<220> FEATURE:
<223> OTHER INFORMATION: hCRT-BstZ17I-HA/UP PCR primer

<400> SEQUENCE: 46 gtataccccat acgacgtccc agactacgct gagcccgccg tctacttcaa ggagc    55

<210> SEQ ID NO 47
<211> LENGTH: 45
<212> TYPE: DNA
<213> ORGANISM: Artificial Sequence
<220> FEATURE:
<223> OTHER INFORMATION: hCRT-PacI/LP PCR primer

<400> SEQUENCE: 47

-continued

```
ttaattaact acagctcgtc atgggcctgg ccggggacat cttcc                45
```

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide that binds CRT

<400> SEQUENCE: 48

```
Lys Leu Gly Phe Phe Lys Arg
1               5
```

<210> SEQ ID NO 49
<211> LENGTH: 60
<212> TYPE: DNA
<213> ORGANISM: Artificial Sequence
<220> FEATURE:
<223> OTHER INFORMATION: Alpha amylase signal peptide (from Aspergillus
      niger alpha-amylase)

<400> SEQUENCE: 49

```
atggttgctt ggtggtcctt gttcttgtac ggattgcaag ttgctgctcc agctttggct    60
```

<210> SEQ ID NO 50
<211> LENGTH: 20
<212> TYPE: PRT
<213> ORGANISM: Artificial Sequence
<220> FEATURE:
<223> OTHER INFORMATION: Alpha amylase signal peptide (from Aspergillus
      niger alpha-amylase)

<400> SEQUENCE: 50

```
Met Val Ala Trp Trp Ser Leu Phe Leu Tyr Gly Leu Gln Val Ala Ala
1               5                  10                  15

Pro Ala Leu Ala
            20
```

VECTORS AND YEAST STRAINS FOR PROTEIN PRODUCTION: CA2+ ATPASE OVEREXPRESSION

CROSS REFERENCE TO RELATED APPLICATIONS

This patent application is a divisional application of U.S. Ser. No. 13/057,807 filed 7 Feb. 2011, which is a National Phase entry of PCT International Application No. PCT/US2009/053247 filed 10 Aug. 2009 and which claims benefit of U.S. Provisional Application No. 61/188,761, filed 12 Aug. 2008.

REFERENCE TO SEQUENCE LISTING SUBMITTED ELECTRONICALLY

The sequence listing of the present application is submitted electronically via EFS-Web as an ASCII formatted sequence listing with a file name "GFIBI000032USDIV-SEQTXT-02JUL2013.txt", creation date of Jul. 2, 2013, and a size of 99 KB. This sequence listing submitted via EFS-Web is part of the specification and is herein incorporated by reference in its entirety.

BACKGROUND OF THE INVENTION (1) Field of the Invention

The present invention relates to host cells that include one or more nucleic acid molecules encoding a $Ca^{2+}$ ATPase, endoplasmic reticulum lectin chaperones, e.g., calreticulin (CRT) or calnexin (CRX), and/or ERp57 protein and their use for producing recombinant glycoproteins that have reduced O-glycosylation.

(2) Description of Related Art

Glycoproteins mediate many essential functions in humans and other mammals, including catalysis, signaling, cell-cell communication, and molecular recognition and association. Glycoproteins make up the majority of non-cytosolic proteins in eukaryotic organisms (Lis and Sharon, Eur. J. Biochem. 218: 1-27 (1993)). Many glycoproteins have been exploited for therapeutic purposes, and during the last two decades, recombinant versions of naturally-occurring glycoproteins have been a major part of the biotechnology industry. Examples of recombinant glycosylated proteins used as therapeutics include erythropoietin (EPO), therapeutic monoclonal antibodies (mAbs), tissue plasminogen activator (tPA), interferon-β (IFN-β), granulocyte-macrophage colony stimulating factor (GM-CSF)5 and human chorionic gonadotrophin (hCH) (Gumming et al., Glycobiology 1:115-130 (1991)). Variations in glycosylation patterns of recombinantly produced glycoproteins have recently been the topic of much attention in the scientific community as recombinant proteins produced as potential prophylactics and therapeutics approach the clinic.

In general, the glycosylation structures of glycoprotein oligosaccharides will vary depending upon the host species of the cells used to produce them. Therapeutic proteins produced in non-human host cells are likely to contain non-human glycosylation which may elicit an immunogenic response in humans—e.g. hypermannosylation in yeast (Ballou, Methods Enzymol. 185:440-470 (1990); α(1,3)-fucose and β(1,2)-xylose in plants, (Cabanes-Macheteau et al, Glycobiology 9: 365-372 (1999)); N-glycolylneuraminic acid in Chinese hamster ovary cells (Noguchi et al., J. Biochem. 117: 5-62 (1995); and, Galα-1,3Gal glycosylation in mice (Borrebaeck et al., Immunol. Today, 14: 477-479 (1993).

Because the oligosaccharide structures of glycoproteins produced by non-human mammalian cells tend to be more closely related to those of human glycoproteins, most commercial glycoproteins are produced in mammalian cells. However, mammalian cells have several important disadvantages as host cells for protein production. Besides being costly, processes for producing proteins in mammalian cells produce heterogeneous populations of glycoforms, have low volumetric titers, and require both ongoing viral containment and significant time to generate stable cell lines. Until about 2000, lower eukaryote host cells suitable for producing recombinant glycoproteins with human-like N-glycosylation patterns had not been possible. Since then, Gerngross in U.S. Pat. No. 7,029,872 disclosed methods for making recombinant lower eukaryote host cells that are capable of making glycoproteins that have human-like N-glycosylation patterns. Thus, there is now considerable interest in using lower eukaryote host cells to produce recombinant glycoproteins.

While the pathway for N-linked glycosylation has been the subject of much analysis, the process and function of O-linked glycosylation is not as well understood. It is known that in contrast to N-linked glycosylation, O-glycosylation is a posttranslational event, which occurs in the cis-Golgi (Varki, Glycobiol., 3: 97-130 (1993)). While a consensus acceptor sequence for O-linked glycosylation like that for N-linked glycosylation does not appear to exist, a comparison of amino acid sequences around a large number of O-linked glycosylation sites of several glycoproteins show an increased frequency of proline residues at positions −1 and +3 relative to the glycosylated residues and a marked increase of serine, threonine, and alanine residues (Wilson et al., Biochem. J., 275: 529-534 (1991)). Stretches of serine and threonine residues in glycoproteins, may also be potential sites for O-glycosylation. It has been shown that yeast-derived recombinant proteins often bear additional unnatural O-glycans compared to their natural counterpart (Van den Steen, et al., Crit. Reviews in Biochem. and Mole. Biol. 33: 151-208, (1998)). These unnatural O-glycans can result in proteins that have unwanted immunogenicity or aberrant activity. Thus, there is a need to develop methods for producing proteins in yeast and other lower eukaryotes that have reduced or no O-glycosylation.

Tanner et al. in U.S. Pat. No. 5,714,377 describes the PMT1 and PMT2 genes of *Saccharomyces cerevisiae* and a method for making recombinant proteins having reduced O-linked glycosylation that uses fungal cells in which one or more of PMT genes have been genetically modified so that recombinant proteins are produced, which have reduced O-linked glycosylation.

Ng et al. in U.S. Published Patent Application No. 20020068325 discloses inhibition of O-glycosylation through the use of antisense or cosuppression or through the engineering of yeast host strains that have loss of function mutations in genes associated with O-linked glycosylation, in particular, one or more of the PMT genes.

Clausen in U.S. Published Patent Application No. 20030186850 discloses the use of GalNAc-beta-benzyl to selectively inhibit lectins of polypeptide GalNAc-transferases and not serve as substrates for other glycosyltransferases involved in O-glycan biosyntheses, thus inhibiting O-glycosylation.

Orchard et al. in U.S. Pat. No. 7,105,554 describes benzylidene thiazolidinediones and their use as antimycotic agents, e.g., antifungal agents which Bobrowicz et al. in WO2007061631 show can be used in a way which is not lethal to the host cells for production of recombinant proteins with reduced O-linked glycosylation.

Konrad et al. in U.S. Published Patent Application No. 20020128235 disclose a method for treating or preventing diabetes mellitus by pharmacologically inhibiting O-linked protein glycosylation in a tissue or cell.

Kojima et al. in U.S. Pat. No. 5,268,364 disclose therapeutic compositions for inhibition of O-glycosylation using compounds such as benzyle-α-N-acetylgalactosamine, which inhibits extension of O-glycosylation leading to accumulation of O-α-GalNAc, to block expression of SLex or SLea by leukocytes or tumor cells and thereby inhibit adhesion of these cells to endothelial cells and platelets.

Boime et al. in U.S. Pat. No. 6,103,501 disclose variants of hormones in which O-linked glycosylation was altered by modifying the amino acid sequence at the site of glycosylation.

However, even in light of the above attempts to produce recombinant host cells that produce proteins that have reduced or no O-glycosylation, there still remains a need for host cells that are capable of producing recombinant proteins that have reduced O-glycosylation.

BRIEF SUMMARY OF THE INVENTION

The present inventors have found that expression of recombinant proteins in a recombinant host cell with reduced O-glycosylation can be effected by overexpressing an endogenous or exogenous $Ca^{2+}$ ATPase in the recombinant host cell. Host cells that overexpress an endogenous or exogenous $Ca^{2+}$ ATPase produce recombinant proteins with reduced O-glycosylation compared to the same cells that do not overexpress the $Ca^{2+}$ ATPase. As shown in the examples, recombinant host lower eukaryote host cells that included an expression cassette encoding a heterologous or endogenous $Ca^{2+}$ ATPase were capable of producing recombinant proteins wherein the O-glycan occupancy was reduced by up to 4 fold compared to cells that did not overexpress an endogenous or exogenous $Ca^{2+}$ ATPase.

Thus, the present invention provides lower eukaryotic host cells, in which a nucleic acid molecule encoding at least one endogenous or exogenous $Ca^{2+}$ ATPase is introduced into and expressed in the host cell, wherein expression of the $Ca^{2+}$ ATPase is ectopic. In particular aspects, the $Ca^{2+}$ ATPase is encoded by an open reading frame operably linked to a heterologous regulatory sequences, which may provide constitutive or regulatable expression of the $Ca^{2+}$ ATPase, and which is operable in the host cell. In further aspects, the lower eukaryotic host cell is a yeast or filamentous fungi host cell. In further still aspects, the host cell is a methylotrophic yeast, for example *Pichia pastoris*. In particular aspects, the $Ca^{2+}$ ATP is selected from the group consisting of the *Pichia pastoris* PMR1 and the *Arabidopsis thaliana* ECA1.

In further aspects, the lower eukaryotic host cells of the invention are further transformed with a recombinant vector comprising regulatory nucleotide sequences derived from lower eukaryotic host cells and a coding sequence encoding a selected mammalian protein to be produced by the above host cells. In certain aspects, the selected mammalian protein is a therapeutic protein, and may be a glycoprotein, including but not limited to, an antibody.

In further embodiments, the host cell may be a yeast or filamentous fungal host cell, such as a *Pichia pastoris* cell, in which a vector encoding at least one endogenous or exogenous $Ca^{2+}$ ATPase is introduced into and expressed in the host cell and the host cell further expresses a nucleic acid molecule comprising regulatory nucleotide sequences derived from or functional in *Pichia pastoris* cells operably linked with an open reading frame encoding a human therapeutic glycoprotein, such as an antibody, which is introduced into the host cell.

It has also been found that overexpressing a calreticulin and an ERp57 protein in the lower eukaryote host cells also effected a reduction in O-glycan occupancy. Thus, also provided are lower eukaryote host cells comprising one or more nucleic acid molecules encoding a calreticulin and/or an ERp57 protein wherein the proteins are ectopically expressed. In further embodiments, the host cells include a nucleic acid molecule encoding at least one endogenous or exogenous $Ca^{2+}$ ATPase, wherein expression of the $Ca^{2+}$ ATPase is ectopic. In general, the lower eukaryote host cell further includes a nucleic acid molecule encoding a recombinant protein, which in particular aspects, is a glycoprotein, which in further aspects is an antibody or fragment thereof such as Fc or Fab.

In further embodiments, any one of the above host cell is engineered to reduce or eliminate the function of at least one endogenous *Pichia pastoris* gene encoding a protein O-mannosyltransferase (PMT) protein to provide a host cell that is capable of making recombinant proteins having reduced O-glycosylation compared to host cells that have functional PMT genes. In further aspects, the PMT protein is selected from the group consisting of PMT1 and PMT4. In further aspects, the host cells are further contacted with one or more inhibitors of PMT gene expression or PMT protein function.

In further embodiments, the gene encoding an endogenous chaperone protein is reduced, deleted, or disrupted and a nucleic acid molecule encoding a heterologous chaperone protein is introduced into the cell. In particular aspects, the chaperone protein is the PDI1 protein.

In further aspects of the above host cells, the host cell is selected from the group consisting of *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stipitis*, *Pichia methanolica*, *Pichia* sp., *Saccharomyces cerevisiae*, *Saccharomyces* sp., *Schizosaccharomyces* sp., *Schizosaccharomyce pombe*, *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Physcomitrella patens* and *Neurospora crassa*. *Pichia* sp., any *Saccharomyces* sp., *Hansenula polymorpha*, any *Kluyveromyces* sp., any *Aspergillus* sp., *Trichoderma reesei*, *Chrysosporium lucknowense*, any *Fusarium* sp. and *Neurospora crassa*.

Further embodiments include methods for producing recombinant proteins that have reduced O-glycosylation or O-glycan occupancy compared to recombinant glycoproteins that do not include the genetic modifications disclosed herein. Recombinant proteins include proteins and glycoproteins of therapeutic relevance, including antibodies and fragments thereof.

Thus, provided is a method for producing a recombinant protein comprising: (a) providing a lower eukaryote host cell comprising a nucleic acid molecule encoding an endogenous or exogenous $Ca^{2+}$ ATPase wherein expression of the $Ca^{2+}$ ATPase in the host cell is ectopic; (b) introducing a nucleic acid molecule into the host cell encoding the recombinant protein: and (c) growing the host cell under conditions suitable for producing the recombinant protein.

Further provided is a method for producing a recombinant protein comprising: (a) providing a lower eukaryote host cell comprising a nucleic acid molecule encoding at least one of CRT or ERp57, wherein expression of the CRT and/or ERp57 in the host cell is ectopic; (b) introducing a nucleic acid molecule into the host cell encoding the recombinant protein: and (c) growing the host cell under conditions suitable for producing the recombinant protein.

Further provided is a method for producing a recombinant protein comprising: (a) providing a lower eukaryote host cell comprising nucleic acid molecules encoding an endogenous or exogenous $Ca^{2+}$ ATPase wherein expression of the $Ca^{2+}$ ATPase in the host cell is ectopic and at least one of CRT or ERp57, wherein expression of the $Ca^{2+}$ ATPase, CRT and/or ERp57 in the host cell is ectopic; (b) introducing a nucleic acid molecule into the host cell encoding the recombinant protein: and (c) growing the host cell under conditions suitable for producing the recombinant protein.

In further embodiments, the function of at least one endogenous Pichia pastoris gene encoding a protein O-mannosyltransferase (PMT) protein to provide a host cell that is capable of making recombinant proteins having reduced O-glycosylation compared to host cells that have functional PMT genes. In further aspects, the PMT protein is selected from the group consisting of PMT1 and PMT4. In further aspects, the host cells are further contacted with one or more inhibitors of PMT gene expression or PMT protein function.

In further embodiments, the gene encoding an endogenous chaperone protein is reduced, deleted, or disrupted and a nucleic acid molecule encoding a heterologous chaperone protein is introduced into the cell. In particular aspects, the chaperone protein is the PDI1 protein.

In further still aspects, any one of the host cells disclosed herein can be grown in the presence of an inhibitor of a PMT gene.

The methods herein are particularly useful for producing proteins of therapeutic value, including but not limited to, antibodies. Thus provided is the use of any one of the host cells herein for producing a protein of therapeutic value. In particular aspects, use of any one of the host cells herein for producing an antibody.

In further aspects of the above methods, the host cell is selected from the group consisting of Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stipitis, Pichia methanolica, Pichia sp., Saccharomyces cerevisiae, Saccharomyces sp., Schizosaccharomyces sp., Schizosaccharomyce pombe, Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens and Neurospora crassa. Pichia sp., any Saccharomyces sp., Hansenula polymorpha, any Kluyveromyces sp., any Aspergillus sp., Trichoderma reesei, Chrysosporium lucknowense, any Fusarium sp. and Neurospora crassa.

Further provided are recombinant proteins produced by the host cells disclosed herein.

In particular embodiments, any one of the aforementioned host cells can further include genetic modifications that enable the host cells to produce glycoproteins have predominantly particular N-glycan structures thereon or particular mixtures of N-glycan structures thereon. For example, the host cells have been genetically engineered to produce N-glycans having a $Man_3GlcNAc_2$ or $Man_5GlcNAc_2$ core structure, which in particular aspects include one or more additional sugars such as GlcNAc, Galactose, or sialic acid on the non-reducing end, and optionally fucose on the GlcNAc at the reducing end. Thus, the N-glycans include both bi-antennary and multi-antennary glycoforms and glycoforms that are bisected. Examples of N-glycans include but are not limited to $Man_8GlcNAc_2$, $Man_7GlcNAc_2$, $Man_6GlcNAc_2$, $Man_5GlcNAc_2$, $GlcNAcMan_5GlcNAc_2$, $GalGlcNAcMan_5GlcNAc_2$, $NANAGalGlcNAcMan_5GlcNAc_2$, $Man_3GlcNAc_2$, $GlcNAc_{(1-4)}Man_3GlcNAc_2$, $Gal_{(1-4)}GlcNAc_{(1-4)}Man_3GlcNAc_2$, $NANA_{(1-4)}Gal_{(1-4)}GlcNAc_{(1-4)}Man_3GlcNAc_2$.

DEFINITIONS

Unless otherwise defined herein, scientific and technical terms and phrases used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual,* 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); *Handbook of Biochemistry: Section A Proteins*, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs cotranslationally in the lumen of the ER and continues in the Golgi apparatus for N-linked glycoproteins.

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine) N-glycans differ with respect to the number of branches (antennae) comprising peripheral sugars (e.g., GlcNAc, galactose, fucose and sialic acid) that are added to the $Man_3GlcNAc_2$ ("Man3") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

Abbreviations used herein are of common usage in the art, see, e.g., abbreviations of sugars, above. Other common abbreviations include "PNGase", or "glycanase" or "glucosidase" which all refer to peptide N-glycosidase F (EC 3.2.2.18).

The term "vector" as used herein is intended to refer to a nucleic acid molecule capable of transporting another nucleic acid molecule to which it has been linked. One type of vector is a "plasmid vector", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

As used herein, the term "sequence of interest" or "gene of interest" refers to a nucleic acid sequence, typically encoding a protein, that is not normally produced in the host cell. The methods disclosed herein allow efficient expression of one or more sequences of interest or genes of interest stably integrated into a host cell genome. Non-limiting examples of sequences of interest include sequences encoding one or more polypeptides having an enzymatic activity, e.g., an enzyme which affects N-glycan synthesis in a host such as mannosyltransferases, N-acetylglucosaminyltransferases, UDP-N-acetylglucosamine transporters, galactosyltransferases, UDP-N-acetylgalactosyltransferase, sialyltransferases and fucosyltransferases.

The term "marker sequence" or "marker gene" refers to a nucleic acid sequence capable of expressing an activity that allows either positive or negative selection for the presence or absence of the sequence within a host cell. For example, the *Pichia pastoris* URA5 gene is a marker gene because its presence can be selected for by the ability of cells containing the gene to grow in the absence of uracil. Its presence can also be selected against by the inability of cells containing the gene to grow in the presence of 5-FOA. Marker sequences or genes do not necessarily need to display both positive and negative selectability. Non-limiting examples of marker sequences or genes from *Pichia pastoris* include ADE1, ARG4, HIS4 and URA3. For antibiotic resistance marker genes, kanamycin, neomycin, geneticin (or G418), paromomycin and hygromycin resistance genes are commonly used to allow for growth in the presence of these antibiotics.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "eukaryotic" refers to a nucleated cell or organism, and includes insect cells, plant cells, mammalian cells, animal cells and lower eukaryotic cells.

The term "lower eukaryotic cells" includes yeast and filamentous fungi. Yeast and filamentous fungi include, but are not limited to: *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stipitis, Pichia methanolica, Pichia* sp., *Saccharomyces cerevisiae, Saccharomyces* sp., *Schizosaccharomyces* sp., *Schizosaccharomyce pombe, Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha*, any *Kluyveromyces* sp., any *Aspergillus* sp., *Trichoderma reesei, Chrysosporium lucknowense*, any *Fusarium* sp. and *Neurospora crassa*.

The function of a gene encoding a protein is said to be 'reduced' when that gene has been modified, for example, by deletion, insertion, mutation or substitution of one or more nucleotides, such that the modified gene encodes a protein which has at least 20% to 50% lower activity, in particular aspects, at least 40% lower activity or at least 50% lower activity, when measured in a standard assay, as compared to the protein encoded by the corresponding gene without such modification. The function of a gene encoding a protein is said to be 'eliminated' when the gene has been modified, for example, by deletion, insertion, mutation or substitution of one or more nucleotides, such that the modified gene encodes a protein which has at least 90% to 99% lower activity, in particular aspects, at least 95% lower activity or at least 99% lower activity, when measured in a standard assay, as compared to the protein encoded by the corresponding gene without such modification.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting in any manner.

DETAILED DESCRIPTION OF THE INVENTION

Figure 1A:
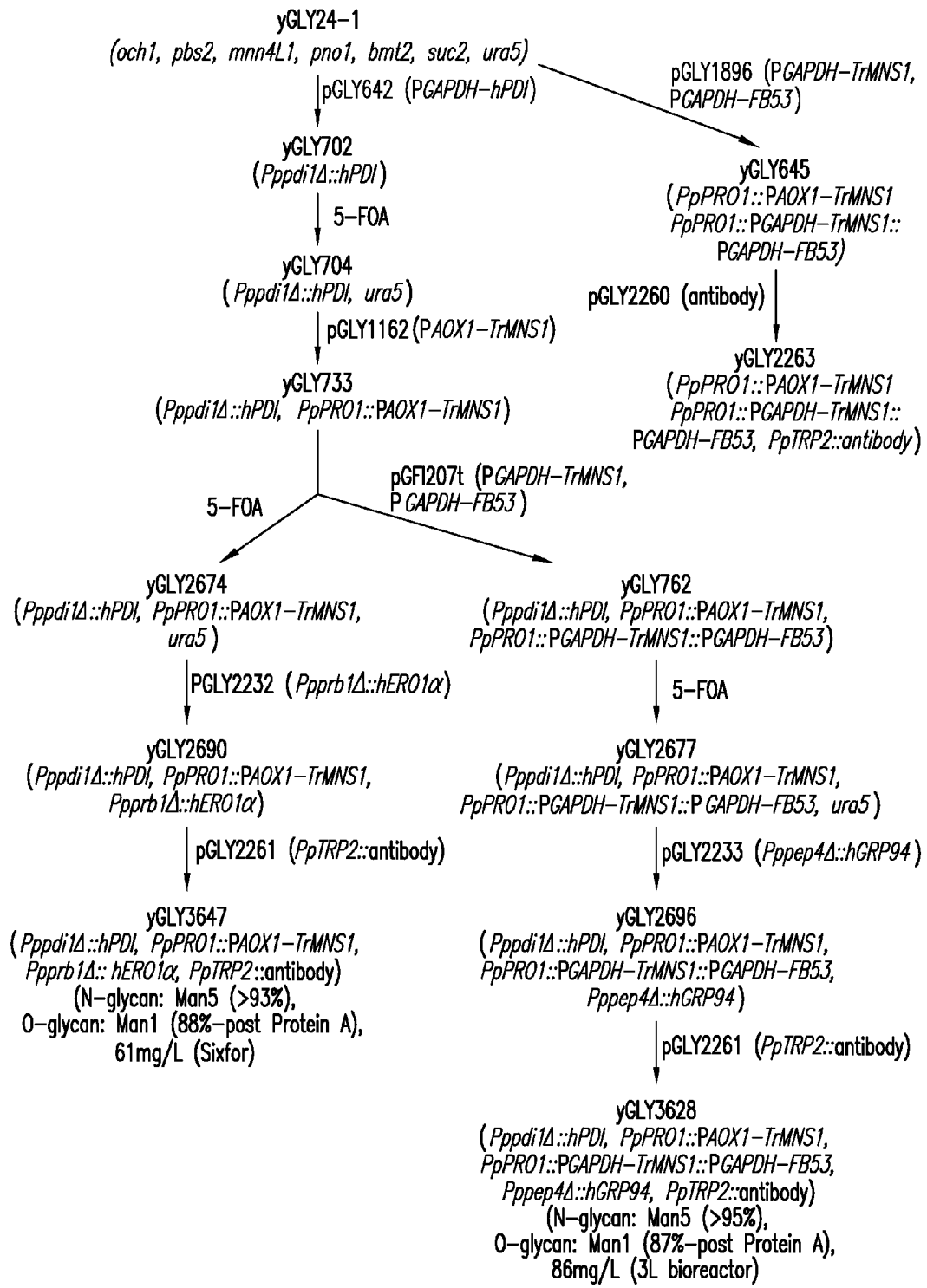
FIGS. 1A and 1B show the genealogy of yeast strains described in the examples for illustrating the invention.

The present invention provides recombinant host cells that are capable of producing recombinant proteins that have reduced O-glycosylation compared to host cells that have not been genetically engineered as disclosed herein. In general, provided are recombinant host cells comprising one or more nucleic acid molecules for ectopic expression of one or more endogenous or exogenous $Ca^{2+}$ ATPases and the use of the recombinant host cells to produce glycoproteins that have reduced O-glycosylation.

We have found that overexpression of an endogenous or exogenous $Ca^{2+}$ ATPase in recombinant host cells enabled us to produce recombinant proteins that had reduced O-glycosylation compared to host cells that did not overexpress an endogenous or exogenous $Ca^{2+}$ ATPase. As shown in Examples 3 and 4, overexpression of *Pichia pastoris* Golgi $Ca^{2+}$ ATPase (PpPMR1) or *Arabidopsis thaliana* ER $Ca^{2+}$ ATPase (AtECA1) effected greater than a 4-fold reduction in O-glycan occupancy compared to the host cell strains that did not express either $Ca^{2+}$ ATPase. Thus, recombinant host cells that include one or more nucleic acid molecules encoding an endogenous or exogenous Golgi or ER $Ca^{2+}$ ATPase, wherein the $Ca^{2+}$ ATPase is operably linked to a heterologous promoter, will provide host cells that are capable of producing recombinant glycoproteins that have reduced O-glycosylation. These host cells can be used for producing recombinant proteins in which it is desired that the amount of O-glycosylation on the protein is reduced. Other $Ca^{2+}$ ATPases that are suitable include but are not limited to human SERCA2b protein (ATP2A2 ATPase, $Ca^{++}$ transporting, cardiac muscle, slow twitch 2) and the *Pichia pastoris* COD1 protein (homologue of *Saccharomyces cerevisiae* SPF1).

Calreticulin (CRT) is a multifunctional protein that acts as a major Ca(2+)-binding (storage) protein in the lumen of the endoplasmic reticulum. It is also found in the nucleus, suggesting that it may have a role in transcription regulation. Calreticulin binds to the synthetic peptide KLGFFKR (SEQ ID NO:47), which is almost identical to an amino acid sequence in the DNA-binding domain of the superfamily of nuclear receptors. Calreticulin binds to antibodies in certain sera of systemic lupus and Sjogren patients which contain anti-Ro/SSA antibodies, it is highly conserved among species, and it is located in the endoplasmic and sarcoplasmic reticulum where it may bind calcium. Calreticulin binds to misfolded proteins and prevents them from being exported from the Endoplasmic reticulum to the Golgi apparatus. Other proteins that are suitable include but are not limited to human UGGT (UDP-glucose:glycoprotein glucosyltransferase) protein and human ERp27 protein.

ERp57 is a chaperone protein of the endoplasmic reticulum that interacts with lectin chaperones calreticulin and calnexin to modulate folding of newly synthesized glycoproteins. The protein was once thought to be a phospholipase; however, it has been demonstrated that the protein actually has protein disulfide isomerase activity. Thus, the ERp57 is a lumenal protein of the endoplasmic reticulum (ER) and a member of the protein disulfide isomerase (PDI) family. It is thought that complexes of lectins and this protein mediate protein folding by promoting formation of disulfide bonds in their glycoprotein substrates. In contrast to archetypal PDI, ERp57 interacts specifically with newly synthesized glycoproteins.

We have further found that overexpression of the human CRT and human ERp57 in *Pichia pastoris* effected about a one-third reduction in O-glycan occupancy compared to strains which did not express the hCRT and hERp57.

Thus, further provided are recombinant host cells comprising one or more nucleic acid molecules encoding a calreticulin protein and/or ERp57 protein for ectopic expression in the host cell. These host cells can be used for producing recombinant proteins where it is desired that the amount of O-glycosylation on the protein is reduced. When the host cells further include one or more nucleic acid molecules encoding an endogenous or heterologous $Ca^{2+}$ ATPase, these host cells have a further reduction in O-glycosylation. As shown in Example 4, providing a recombinant host cell that overexpressed either an endogenous $Ca^{2+}$ ATPase or an exogenous $Ca^{2+}$ ATPase and overexpressed the human calreticulin protein and human ERp57 protein had a further reduction in the O-glycosylation of recombinant proteins produced by the host cells. Thus, further provided are recombinant host cells comprising one or more nucleic acid molecules encoding an endogenous or heterologous $Ca^{2+}$ ATPase and one or more nucleic acid molecules encoding a calreticulin protein and/or an ERp57 protein. These host cells can be used to produce glycoproteins with reduced O-glycosylation.

Molecular chaperones play a critical role in the folding and secretion of antibodies. One chaperone protein in particular, Protein Disulfide Isomerase (PDI), functions to catalyze inter and intra disulphide bond formation that link the antibody heavy and light chains. Protein disulfide isomerase (PDI) can produce a substantial increase or a substantial decrease in the recovery of disulfide-containing proteins, when compared with the uncatalyzed reaction; a high concentration of PDI in the endoplasmic reticulum (ER) is essential for the expression of disulfide-containing proteins (Puig and Gilbert, J. Biol. Chem. 269: 7764-7771 (1994)). As shown in the Examples, cells in which the endogenous PDI1 chaperone gene has been replaced with a human PDI chaperone gene had reduced O-glycosylation. When these cells further include ectopic overexpression of an endogenous or exogenous $Ca^{2+}$ ATPase and/or CRT and/or ERp57 protein, there was a further reduction in O-glycosylation (See Examples 3 and 4).

Thus, further included are host cells that ectopically express a $CA^{2+}$ ATPase and/or CRT and/or ERp57 protein and wherein one or more genes encoding an endogenous chaperone protein has been deleted or disrupted and a nucleic acid molecule encoding a heterologous chaperone protein has been introduced for ectopic expression of the chaperone protein. Further embodiments, include the above cells wherein additional heterologous co-chaperone proteins, such as ERO-1αand/or the GRP94 proteins are also expressed in the cells.

Lower eukaryotic cells such as *Saccharomyces cerevisiae*, *Candida albicans*, and *Pichia pastoris*, contain a family of genes known as protein O-mannosyltransferases (PMTs) involved in the transfer of mannose to seryl and threonyl residues of secretory proteins. We found that *Pichia pastoris* cell lines, which have been genetically altered to express one or more humanized or chimeric chaperone genes, are better able to tolerate deletion of one or more PMT genes, with little or no effect on cell growth or protein expression. PMT genes which may be deleted include PMT1, PMT2, PMT4, PMT5, and PMT6. In general, *Pichia pastoris* host cells in which both the OCH1 gene and the PMT gene is deleted either grow poorly or not at all. Deletion or functional knockout of the OCH1 gene is necessary for constructing recombinant *Pichia pastoris* host cells that can make human glycoproteins that have human-like N-glycans. Because it is desirable to produce human glycoproteins that have no or reduced O-glycosylation, there has been a need to find means for reducing O-glycosylation in recombinant *Pichia pastoris* host cells that are also capable of producing human glycoproteins with human-like N-glycans. Thus, in further embodiments, provided are host cells that further include deletion or disruption of one or more PMT genes.

In further aspects, the overexpressed gene product is a secreted gene product. Procedures for observing whether an overexpressed gene product is secreted are readily available to the skilled artisan. For example, Goeddel, (Ed.) 1990, Gene Expression Technology, Methods in Enzymology, Vol 185, Academic Press, and Sambrook et al. 1989, Molecular Cloning: A Laboratory Manual, Vols. 1-3, Cold Spring Harbor Press, N.Y., provide procedures for detecting secreted gene products.

To secrete an overexpressed gene product the host cell is cultivated under conditions sufficient for secretion of the overexpressed gene product. Such conditions include temperature, nutrient and cell density conditions that permit secretion by the cell. Moreover, such conditions are conditions under which the cell can perform basic cellular functions of transcription, translation and passage of proteins from one cellular compartment to another and are known to the skilled artisan.

Moreover, as is known to the skilled artisan a secreted gene product can be detected in the culture medium used to maintain or grow the present host cells. The culture medium can be separated from the host cells by known procedures, for example, centrifugation or filtration. The overexpressed gene product can then be detected in the cell-free culture medium by taking advantage of known properties characteristic of the overexpressed gene product. Such properties can include the distinct immunological, enzymatic or physical properties of the overexpressed gene product. For example, if an overexpressed gene product has a unique enzyme activity an assay for that activity can be performed on the culture medium used by the host cells. Moreover, when antibodies reactive against a given overexpressed gene product are available, such antibodies can be used to detect the gene product in any known immunological assay (See Harlowe, et al., 1988, Antibodies: A Laboratory Manual, Cold Spring Harbor Laboratory Press).

In addition, a secreted gene product can be a fusion protein wherein the gene product includes a heterologous signal or leader peptide that facilitates the secretion of the gene product. Secretion signal peptides are discrete amino acid sequences, which cause the host cell to direct a gene product through internal and external cellular membranes and into the extracellular environment. Secretion signal peptides are present at the N-terminus of a nascent polypeptide gene product targeted for secretion. Additional eukaryotic secretion signals can also be present along the polypeptide chain of the gene product in the form of carbohydrates attached to specific amino acids, i.e. glycosylation secretion signals.

N-terminal signal peptides include a hydrophobic domain of about 10 to about 30 amino acids which can be preceded by a short charged domain of about two to about 10 amino acids. Moreover, the signal peptide is present at the N-terminus of gene products destined for secretion. In general, the particular sequence of a signal sequence is not critical but signal sequences are rich in hydrophobic amino acids such as alanine (Ala), valine (Val), leucine (Leu), isoleucine (Ile), proline (Pro), phenylalanine (Phe), tryptophan (Trp), methionine (Met) and the like.

Many signal peptides are known (Michaelis et al., Ann. Rev. Microbiol. 36: 425 (1982). For example, the yeast acid phosphatase, yeast invertase, and the yeast α-factor signal peptides have been attached to heterologous polypeptide coding regions and used successfully for secretion of the heterologous polypeptide (See for example, Sato et al. Gene 83: 355-365 (1989); Chang et al. Mol. Cell. Biol. 6: 1812-1819 (1986); and Brake et al. Proc. Natl. Acad. Sci. USA 81: 4642-4646 (1984). Therefore, the skilled artisan can readily design or obtain a nucleic acid molecule which encodes a coding region for an overexpressed gene product which also has a signal peptide at the 5'-end.

Examples of overexpressed gene products which are preferably secreted by the present methods include mammalian gene products such as enzymes, cytokines, growth factors, hormones, vaccines, antibodies and the like. More particularly, overexpressed gene products include but are not limited to gene products such as erythropoietin, insulin, somatotropin, growth hormone releasing factor, platelet derived growth factor, epidermal growth factor, transforming growth factor $\alpha$, transforming growth factor $\beta$, epidermal growth factor, fibroblast growth factor, nerve growth factor, insulin-like growth factor I, insulin-like growth factor II, clotting Factor VIII, superoxide dismutase, $\alpha$-interferon, $\gamma$-interferon, interleukin-1, interleukin-2, interleukin-3, interleukin-4, interleukin-5, interleukin-6, granulocyte colony stimulating factor, multi-lineage colony stimulating activity, granulocyte-macrophage stimulating factor, macrophage colony stimulating factor, T cell growth factor, lymphotoxin, immunoglobulins, antibodies, and the like. Further included are fusion proteins, including but not limited to, peptides and polypeptides fused to the constant region of an immunoglobulin or antibody. Particularly useful overexpressed gene products are human gene products.

The terms "antibody", "antibodies", and "immunoglobulin(s)" encompass any recombinant monoclonal antibody produced by recombinant DNA technology and further is meant to include humanized and chimeric antibodies.

The present methods can readily be adapted to enhance secretion of any overexpressed gene product which can be used as a vaccine. Overexpressed gene products which can be used as vaccines include any structural, membrane-associated, membrane-bound or secreted gene product of a mammalian pathogen. Mammalian pathogens include viruses, bacteria, single-celled or multi-celled parasites which can infect or attack a mammal For example, viral vaccines can include vaccines against viruses such as human immunodeficiency virus (HIV), *R. rickettsii*, vaccinia, *Shigella*, poliovirus, adenovirus, influenza, hepatitis A, hepatitis B, dengue virus, Japanese B encephalitis, Varicella zoster, cytomegalovirus, hepatitis A, rotavirus, as well as vaccines against viral diseases like Lyme disease, measles, yellow fever, mumps, rabies, herpes, influenza, parainfluenza and the like. Bacterial vaccines can include vaccines against bacteria such as *Vibrio cholerae, Salmonella typhi, Bordetella pertussis, Streptococcus pneumoniae, Hemophilus* influenza, *Clostridium tetani, Corynebacterium diphtheriae, Mycobacterium leprae, Neisseria gonorrhoeae, Neisseria meningitidis, Coccidioides immitis*, and the like.

In general, the overexpressed proteins of the present invention (for example, $Ca^{2+}$ ATPase, ERp57, calreticulin) and recombinant protein are expressed recombinantly, that is, by placing a nucleic acid molecule encoding an overexpressed protein or recombinant protein into an expression cassette. Such an expression cassette minimally contains a regulatory sequence which effects expression of the protein when the sequence is operably linked to a nucleic acid molecule encoding the protein. The expression cassette is then inserted into a vector such as a plasmid that can also contain additional elements like origins of replication, selectable markers, transcription or termination signals, centromeres, autonomous replication sequences, and the like to provide an expression vector.

An expression vector can be a replicable or a non-replicable expression vector. A replicable expression vector can replicate either independently of host cell chromosomal DNA or because such a vector has integrated into host cell chromosomal DNA. An integrating expression vector comprises a targeting sequence that targets the expression vector to a particular location in the host cell genome where the vector then integrates. Upon integration into host cell chromosomal DNA such an expression vector can lose some structural elements but retains the nucleic acid molecule encoding the overexpressed or recombinant protein and a segment which can effect expression of the overexpressed or recombinant protein. Therefore, the expression vectors herein can be chromosomally integrating or chromosomally nonintegrating expression vectors.

In a further embodiment, one or more overexpressed or recombinant proteins are overexpressed in a host cell by introduction of integrating or nonintegrating expression vectors into the host cell. Following introduction of at least one expression vector encoding at least one overexpressed or recombinant protein, the gene product is then overexpressed by inducing expression of an endogenous gene encoding the gene product, or by introducing into the host cell an expression vector encoding the gene product. In another embodiment, cell lines are established which constitutively or inducibly express at least one heterologous chaperone protein. An expression vector encoding the gene product to be overexpressed is introduced into such cell lines to achieve increased secretion of the overexpressed gene product.

The present expression vectors can be replicable in one host cell type, e.g., *Escherichia coli*, and undergo little or no replication in another host cell type, e.g., a eukaryotic host cell, so long as an expression vector permits expression of the overexpressed or recombinant proteins and thereby facilitates secretion of such gene products in a selected host cell type.

Expression vectors as described herein include DNA or RNA molecules that have been engineered for controlled expression of a desired gene, that is, a gene encoding the overexpressed or recombinant proteins. Such vectors also encode nucleic acid molecule segments which are operably linked to nucleic acid molecules encoding the overexpressed or recombinant proteins. Operably linked in this context means that such segments can effect expression of nucleic acid molecules encoding the overexpressed or recombinant proteins. These nucleic acid sequences include promoters, enhancers, upstream control elements, transcription factors or repressor binding sites, termination signals and other elements which can control gene expression in the contemplated host cell. Preferably the vectors are vectors, bacteriophages, cosmids, or viruses.

Expression vectors of the present invention function in yeast or mammalian cells. Yeast vectors can include the yeast 2µ circle and derivatives thereof, yeast vectors encoding yeast autonomous replication sequences, yeast minichromosomes, any yeast integrating vector and the like. A comprehensive listing of many types of yeast vectors is provided in Parent et al. (Yeast 1: 83-138 (1985)).

Elements or nucleic acid regulatory sequences capable of effecting expression of a gene product include promoters, enhancer elements, upstream activating sequences, transcription termination signals and polyadenylation sites. All such promoter and transcriptional regulatory elements, singly or in combination, are contemplated for use in the present expression vectors. Moreover, genetically-engineered and mutated regulatory sequences are also contemplated herein.

Promoters are DNA sequence elements for controlling gene expression. In particular, promoters specify transcription initiation sites and can include a TATA box and upstream promoter elements. The promoters selected are those which would be expected to be operable in the particular host system selected. For example, yeast promoters are used in the present expression vectors when a yeast host cell such as *Saccharomyces cerevisiae, Kluyveromyces lactis*, or *Pichia pastoris* is used whereas fungal promoters would be used in host cells such as *Aspergillus niger, Neurospora crassa*, or *Tricoderma reesei*. Examples of yeast promoters include but are not limited to the GAPDH, AOX1, GAL1, PGK, GAP, TPI, CYC1, ADH2, PHO5, CUP1, MFα1, PMA1, PDI, TEF, and GUT1 promoters. Romanos et al. (Yeast 8: 423-488 (1992)) provide a review of yeast promoters and expression vectors.

The promoters that are operably linked to the nucleic acid molecules disclosed herein can be constitutive promoters or inducible promoters. Inducible promoters, that is. promoters which direct transcription at an increased or decreased rate upon binding of a transcription factor. Transcription factors as used herein include any factor that can bind to a regulatory or control region of a promoter an thereby affect transcription. The synthesis or the promoter binding ability of a transcription factor within the host cell can be controlled by exposing the host to an inducer or removing an inducer from the host cell medium. Accordingly to regulate expression of an inducible promoter, an inducer is added or removed from the growth medium of the host cell. Such inducers can include sugars, phosphate, alcohol, metal ions, hormones, heat, cold and the like. For example, commonly used inducers in yeast are glucose, galactose, and the like.

Transcription termination sequences that are selected are those that are operable in the particular host cell selected. For example, yeast transcription termination sequences are used in the present expression vectors when a yeast host cell such as *Saccharomyces cerevisiae, Kluyveromyces lactis*, or *Pichia pastoris* is used whereas fungal transcription termination sequences would be used in host cells such as *Aspergillus niger, Neurospora crassa*, or *Tricoderma reesei*. Transcription termination sequences include but are not limited to the *Saccharomyces cerevisiae* CYC transcription termination sequence (ScCYC TT), the *Pichia pastoris* ALG3 transcription termination sequence (ALG3 TT), and *Pichia pastoris* PMA1 transcription termination sequence (PpPMA1 TT).

The expression vectors of the present invention can also encode selectable markers. Selectable markers are genetic functions that confer an identifiable trait upon a host cell so that cells transformed with a vector carrying the selectable marker can be distinguished from non-transformed cells. Inclusion of a selectable marker into a vector can also be used to ensure that genetic functions linked to the marker are retained in the host cell population. Such selectable markers can confer any easily identified dominant trait, e.g. drug resistance, the ability to synthesize or metabolize cellular nutrients and the like.

Yeast selectable markers include drug resistance markers and genetic functions which allow the yeast host cell to synthesize essential cellular nutrients, e.g. amino acids. Drug resistance markers which are commonly used in yeast include chloramphenicol, kanamycin, methotrexate, G418 (geneticin), Zeocin, and the like. Genetic functions which allow the yeast host cell to synthesize essential cellular nutrients are used with available yeast strains having auxotrophic mutations in the corresponding genomic function. Common yeast selectable markers provide genetic functions for synthesizing leucine (LEU2), tryptophan (TRP1 and TRP2), proline (PRO1), uracil (URA3, URA5, URA6), histidine (HIS3), lysine (LYS2), adenine (ADE1 or ADE2), and the like. Other yeast selectable markers include the ARR3 gene from *S. cerevisiae*, which confers arsenite resistance to yeast cells that are grown in the presence of arsenite (Bobrowicz et al., Yeast, 13:819-828 (1997); Wysocki et al., J. Biol. Chem. 272:30061-30066 (1997)). A number of suitable integration sites include those enumerated in U.S. Published application No. 2007/0072262 and include homologs to loci known for *Saccharomyces cerevisiae* and other yeast or fungi. Methods for integrating vectors into yeast are well known, for example, see U.S. Pat. No. 7,479,389, WO2007136865, and PCT/US2008/13719. Examples of insertion sites include, but are not limited to, *Pichia* ADE genes; *Pichia* TRP (including TRP1 through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al., Gene 263:159-169 (2001) and U.S. Pat. No. 4,818,700, the HIS3 and TRP1 genes have been described in Cosano et al., Yeast 14:861-867 (1998), HIS4 has been described in GenBank Accession No. X56180.

Therefore the present expression vectors can encode selectable markers which are useful for identifying and maintaining vector-containing host cells within a cell population present in culture. In some circumstances selectable markers can also be used to amplify the copy number of the expression vector. After inducing transcription from the present expression vectors to produce an RNA encoding an overexpressed or recombinant protein, the RNA is translated by cellular factors to produce the overexpressed or recombinant protein.

In yeast and other eukaryotes, translation of a messenger RNA (mRNA) is initiated by ribosomal binding to the 5' cap of the mRNA and migration of the ribosome along the mRNA to the first AUG start codon where polypeptide synthesis can begin. Expression in yeast and mammalian cells generally does not require specific number of nucleotides between a ribosomal-binding site and an initiation codon, as is sometimes required in prokaryotic expression systems. However, for expression in a yeast or a mammalian host cell, the first AUG codon in an mRNA is preferably the desired translational start codon.

Moreover, when expression is performed in a yeast host cell the presence of long untranslated leader sequences, e.g. longer than 50-100 nucleotides, can diminish translation of an mRNA. Yeast mRNA leader sequences have an average length of about 50 nucleotides, are rich in adenine, have little secondary structure and almost always use the first AUG for initiation. Since leader sequences which do not have these characteristics can decrease the efficiency of protein translation, yeast leader sequences are preferably used for expression of an overexpressed gene product or a chaperone protein in a yeast host cell. The sequences of many yeast leader sequences are known and are available to the skilled artisan, for example, by reference to Cigan et al. (Gene 59: 1-18 (1987)).

In addition to the promoter, the ribosomal-binding site and the position of the start codon, factors which can effect the level of expression obtained include the copy number of a replicable expression vector. The copy number of a vector is generally determined by the vector's origin of replication and any cis-acting control elements associated therewith. For example, an increase in copy number of a yeast episomal vector encoding a regulated centromere can be achieved by inducing transcription from a promoter which is closely juxtaposed to the centromere. Moreover, encoding the yeast FLP function in a yeast vector can also increase the copy number of the vector.

One skilled in the art can also readily design and make expression vectors which include the above-described sequences by combining DNA fragments from available vectors, by synthesizing nucleic acid molecules encoding such regulatory elements or by cloning and placing new regulatory elements into the present vectors. Methods for making expression vectors are well-known. Overexpressed DNA methods are found in any of the myriad of standard laboratory manuals on genetic engineering.

The expression vectors of the present invention can be made by ligating the overexpressed or recombinant protein coding regions in the proper orientation to the promoter and other sequence elements being used to control gene expression. After construction of the present expression vectors, such vectors are transformed into host cells where the overexpressed gene product and the overexpressed or recombinant protein can be expressed. Methods for transforming yeast and other lower eukaryotic cells with expression vectors are well known and readily available to the skilled artisan. For example, expression vectors can be transformed into yeast cells by any of several procedures including lithium acetate, spheroplast, electroporation, and similar procedures.

Yeast host cells which can be used with yeast replicable expression vectors include any wild type or mutant strain of yeast which is capable of secretion. Such strains can be derived from *Saccharomyces cerevisiae, Hansenula polymorpha, Kluyveromyces lactis, Pichia pastoris, Schizosaccharomyces pombe, Yarrowia lipolytica*, and related species of yeast. In general, useful mutant strains of yeast include strains which have a genetic deficiency that can be used in combination with a yeast vector encoding a selectable marker. Many types of yeast strains are available from the Yeast Genetics Stock Center (Donner Laboratory, University of California, Berkeley, Calif. 94720), the American Type Culture Collection (12301 Parklawn Drive, Rockville, Md. 20852, hereinafter ATCC), the National Collection of Yeast Cultures (Food Research Institute, Colney Lane, Norwich NR47UA, UK) and the Centraalbureau voor Schimmelcultures (Yeast Division, Julianalaan 67a, 2628 BC Delft, Netherlands).

In general, lower eukaryotes such as yeast are useful for expression of glycoproteins because they can be economically cultured, give high yields, and when appropriately modified are capable of suitable glycosylation. Yeast particularly offers established genetics allowing for rapid transformations, tested protein localization strategies and facile gene knock-out techniques. Suitable vectors have expression control sequences, such as promoters, including 3-phosphoglycerate kinase or other glycolytic enzymes, and an origin of replication, termination sequences and the like as desired.

Various yeasts, such as *Kluyveromyces lactis, Pichia pastoris, Pichia methanolica*, and *Hansenula polymorpha* are useful for cell culture because they are able to grow to high cell densities and secrete large quantities of recombinant protein. Likewise, filamentous fungi, such as *Aspergillus niger, Fusarium* sp, *Neurospora crassa* and others can be used to produce glycoproteins of the invention at an industrial scale.

Lower eukaryotes, particularly yeast, can be genetically modified so that they express glycoproteins in which the glycosylation pattern is human-like or humanized. Such can be achieved by eliminating selected endogenous glycosylation enzymes and/or supplying exogenous enzymes as described by Gerngross et al., US 20040018590. For example, a host cell can be selected or engineered to be depleted in 1,6-mannosyl transferase activities, which would otherwise add mannose residues onto the N-glycan on a glycoprotein.

In one embodiment, the host cell further includes an α1,2-mannosidase catalytic domain fused to a cellular targeting signal peptide not normally associated with the catalytic domain and selected to target the α1,2-mannosidase activity to the ER or Golgi apparatus of the host cell. Passage of a recombinant glycoprotein through the ER or Golgi apparatus of the host cell produces a recombinant glycoprotein comprising a $Man_5GlcNAc_2$ glycoform, for example, a recombinant glycoprotein composition comprising predominantly a $Man_5GlcNAc_2$ glycoform. For example, U.S. Pat. No. 7,029,872 and U.S. Published Patent Application Nos. 2004/0018590 and 2005/0170452 disclose lower eukaryote host cells capable of producing a glycoprotein comprising a $Man_5GlcNAc_2$ glycoform.

In a further embodiment, the immediately preceding host cell further includes a GlcNAc transferase I (GnT I) catalytic domain fused to a cellular targeting signal peptide not normally associated with the catalytic domain and selected to target GlcNAc transferase I activity to the ER or Golgi apparatus of the host cell. Passage of the recombinant glycoprotein through the ER or Golgi apparatus of the host cell produces a recombinant glycoprotein comprising a $GlcNAcMan_5GlcNAc_2$ glycoform, for example a recombinant glycoprotein composition comprising predominantly a $GlcNAcMan_5GlcNAc_2$ glycoform. U.S. Pat. No. 7,029,872 and U.S. Published Patent Application Nos. 2004/0018590 and 2005/0170452 disclose lower eukaryote host cells capable of producing a glycoprotein comprising a $GlcNAcMan_5GlcNAc_2$ glycoform. The glycoprotein produced in the above cells can be treated in vitro with a hexaminidase to produce a recombinant glycoprotein comprising a $Man_5GlcNAc_2$ glycoform.

In a further embodiment, the immediately preceding host cell further includes a mannosidase II catalytic domain fused to a cellular targeting signal peptide not normally associated with the catalytic domain and selected to target mannosidase II activity to the ER or Golgi apparatus of the host cell. Passage of the recombinant glycoprotein through the ER or Golgi apparatus of the host cell produces a recombinant glycoprotein comprising a $GlcNAcMan_3GlcNAc_2$ glycoform, for example a recombinant glycoprotein composition comprising predominantly a $GlcNAcMan_3GlcNAc_2$ glycoform. U.S. Pat. No. 7,029,872 and U.S. Published Patent Application No. 2004/0230042 discloses lower eukaryote host cells that express mannosidase II enzymes and are capable of producing glycoproteins having predominantly a $GlcNAc_2Man_3GlcNAc_2$ glycoform. The glycoprotein produced in the above cells can be treated in vitro with a hexaminidase to produce a recombinant glycoprotein comprising a $Man_3GlcNAc_2$ glycoform.

In a further embodiment, the immediately preceding host cell further includes GlcNAc transferase II (GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a $GlcNAc_2Man_3GlcNAc_2$ glycoform, for example a recombinant glycoprotein composition comprising predominantly a $GlcNAc_2Man_3GlcNAc_2$ glycoform. U.S. Pat. No. 7,029,872 and U.S. Published Patent Application Nos. 2004/0018590 and 2005/0170452 disclose lower eukaryote host cells capable of producing a glycoprotein comprising a $GlcNAc_2Man_3GlcNAc_2$ glycoform. The glycoprotein produced in the above cells can be treated in vitro with a hexaminidase to produce a recombinant glycoprotein comprising a $Man_3GlcNAc_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a GalGlcNAc$_2$Man$_3$GlcNAc$_2$ or Gal$_2$GlcNAc$_2$Man$_3$GlcNAc$_2$ glycoform, or mixture thereof for example a recombinant glycoprotein composition comprising predominantly a GalGlcNAc$_2$Man$_3$GlcNAc$_2$ glycoform or Gal$_2$GlcNAc$_2$Man$_3$GlcNAc$_2$ glycoform or mixture thereof U.S. Pat. No. 7,029,872 and U.S. Published Patent Application No. 2006/0040353 discloses lower eukaryote host cells capable of producing a glycoprotein comprising a Gal$_2$GlcNAc$_2$Man$_3$GlcNAc$_2$ glycoform. The glycoprotein produced in the above cells can be treated in vitro with a galactosidase to produce a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform.

In a further embodiment, the immediately preceding host cell further includes a sialyltransferase catalytic domain fused to a cellular targeting signal peptide not normally associated with the catalytic domain and selected to target sialytransferase activity to the ER or Golgi apparatus of the host cell. Passage of the recombinant glycoprotein through the ER or Golgi apparatus of the host cell produces a recombinant glycoprotein comprising predominantly a NANA$_2$Gal$_2$GlcNAc$_2$Man$_3$GlcNAc$_2$ glycoform or NANAGal$_2$GlcNAc$_2$Man$_3$GlcNAc$_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729 discloses a method for genetically engineering lower eukaryotes to have a CMP-sialic acid synthesis pathway and U.S. Published Patent Application No. 2006/0286637 discloses a method for genetically engineering lower eukaryotes to produce sialylated glycoproteins. The glycoprotein produced in the above cells can be treated in vitro with a neuraminidase to produce a recombinant glycoprotein comprising predominantly a Gal$_2$GlcNAc$_2$Man$_3$GlcNAc$_2$ glycoform or GalGlcNAc$_2$Man$_3$GlcNAc$_2$ glycoform or mixture thereof.

Any one of the preceding host cells can further include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX) N-glycan structures such as disclosed in U.S. Published Patent Application Nos. 2004/074458 and 2007/0037248.

In further embodiments, the host cell that produces glycoproteins that have predominantly GlcNAcMan$_5$GlcNAc$_2$ N-glycans further includes a galactosyltransferase catalytic domain fused to a cellular targeting signal peptide not normally associated with the catalytic domain and selected to target Galactosyltransferase activity to the ER or Golgi apparatus of the host cell. Passage of the recombinant glycoprotein through the ER or Golgi apparatus of the host cell produces a recombinant glycoprotein comprising predominantly the GalGlcNAcMan$_5$GlcNAc$_2$ glycoform.

In a further embodiment, the immediately preceding host cell that produced glycoproteins that have predominantly the predominantly the GalGlcNAcMan$_5$GlcNAc$_2$ N-glycans further includes a sialyltransferase catalytic domain fused to a cellular targeting signal peptide not normally associated with the catalytic domain and selected to target sialytransferase activity to the ER or Golgi apparatus of the host cell. Passage of the recombinant glycoprotein through the ER or Golgi apparatus of the host cell produces a recombinant glycoprotein comprising a NANAGalGlcNAcMan$_5$GlcNAc$_2$ glycoform.

Various of the preceding host cells further include one or more sugar transporters such as UDP-GlcNAc transporters (for example, *Kluyveromyces lactis* and *Mus musculus* UDP-GlcNAc transporters), UDP-galactose transporters (for example, *Drosophila melanogaster* UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

In further embodiments of the above host cells, the host cells are further genetically engineered to eliminate glycoproteins having α-mannosidase-resistant N-glycans by deleting or disrupting the β-mannosyltransferase gene (BMT2) (See, U.S. Published Patent Application No. 2006/0211085) and glycoproteins having phosphomannose residues by deleting or disrupting one or both of the phosphomannosyl transferase genes PNO1 and MNN4B (See for example, U.S. Pat. Nos. 7,198,921 and 7,259,007). In further still embodiments of the above host cells, the host cells are further genetically modified to eliminate O-glycosylation of the glycoprotein by deleting or disrupting one or more of the protein O-mannosyltransferase (Dol-P-Man:Protein (Ser/Thr) Mannosyl Transferase genes) (PMTs) (See U.S. Pat. No. 5,714,377) or grown in the presence of i inhibitors such as Pmt-1, Pmti-2, and Pmti-3 as disclosed in Published International Application No. WO 2007061631, or both.

Thus, provided are host cells that have been genetically modified to produce glycoproteins wherein the predominant N-glycans thereon include but are not limited to Man$_8$GlcNAc$_2$, Man$_7$GlcNAc$_2$, Man$_6$GlcNAc$_2$, Man$_5$GlcNAc$_2$, GlcNAcMan$_5$GlcNAc$_2$, GalGlcNAcMan$_5$GlcNAc$_2$, NANAGalGlcNAcMan$_5$GlcNAc$_2$, Man$_3$GlcNAc$_2$, GlcNAc$_{(1-4)}$Man$_3$GlcNAc$_2$, Gal$_{(1-4)}$GlcNAc$_{(1-4)}$Man$_3$GlcNAc$_2$, NANA$_{(1-4)}$Gal$_{(1-4)}$GlcNAc$_{(1-4)}$Man$_3$GlcNAc$_2$. Further included are host cells that produce glycoproteins that have particular mixtures of the aforementioned N-glycans thereon.

In the following examples, heterologous human proteins are expressed in host cells of the species *Pichia pastoris*. These examples demonstrate the invention with respect to specific embodiments of the invention, and are not to be construed as limiting in any manner. The skilled artisan, having read the disclosure and examples herein, will recognize that numerous variants, modifications and improvements to the methods and materials described that are possible without deviating from the practice of the present invention.

EXAMPLE 1

This example shows the construction of a recombinant *Pichia pastoris* that produces recombinant proteins with Man$_5$GlcNAc$_2$ N-glycans.

Figure 2A:
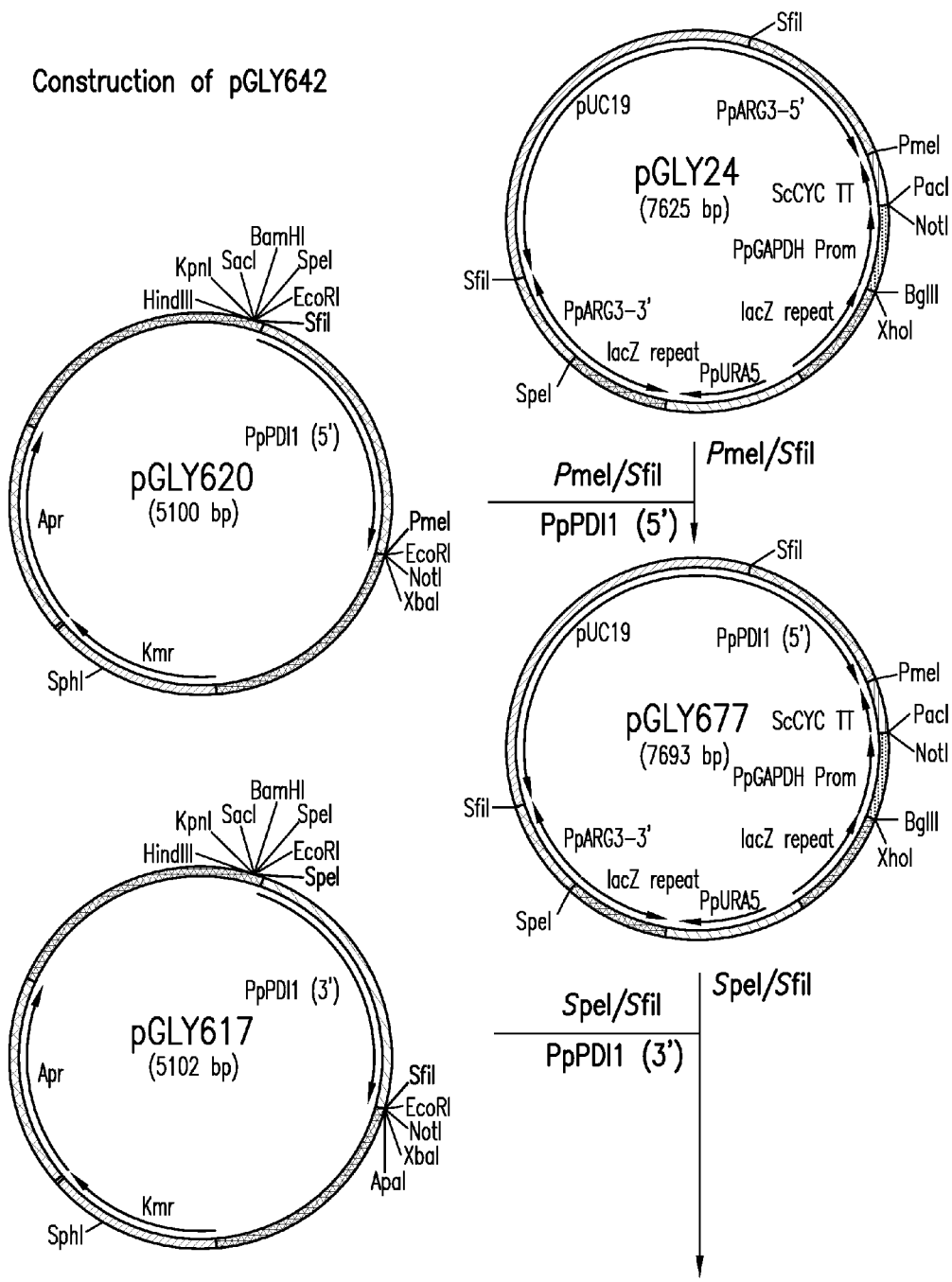
FIGS. 2A and 2B illustrate the construction of plasmid vector pGLY642 encoding the human PDI1 (hPDI) and targeting the *Pichia pastoris* PDI1 locus.
Figure 2B:
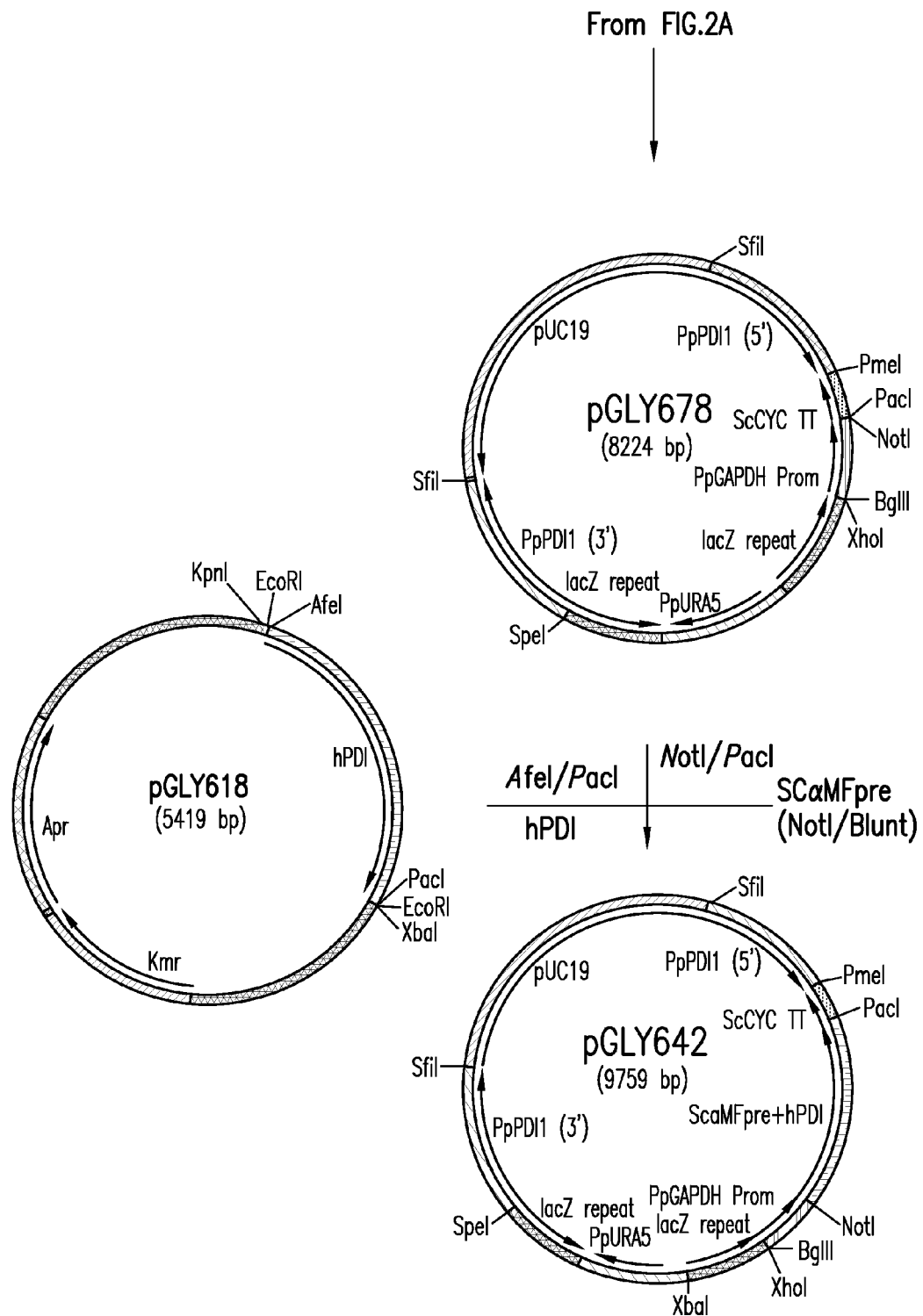

Construction of expression/integration plasmid vector pGLY642 comprising an expression cassette encoding the human PDI protein and nucleic acid molecules to target the plasmid vector to the *Pichia pastoris* PDI1 locus for replacement of the gene encoding the *Pichia pastoris* PDI1 with a nucleic acid molecule encoding the human PDI was as follows and is shown in FIGS. 2A and 2B. cDNA encoding the human PDI1 was amplified by PCR using the primers hPDI/UP1: 5' AGCGCTGACGCCCCGAGGAGGAGGACCAC 3' (SEQ ID NO: 1) and hPDI/LP-PacI: 5' CCTTAATTAAT- TACAGTTCATCATGCACAGCTTTC TGATCAT 3' (SEQ ID NO: 2), Pfu turbo DNA polymerase (Stratagene, La Jolla, Calif.), and a human liver cDNA (BD Bioscience, San Jose, Calif.). The PCR conditions were 1 cycle of 95° C. for two minutes, 25 cycles of 95° C. for 20 seconds, 58° C. for 30 seconds, and 72° C. for 1.5 minutes, and followed by one cycle of 72° C. for 10 minutes. The resulting PCR product was cloned into plasmid vector pCR2.1 to make plasmid vector pGLY618. The nucleotide and amino acid sequences of the human PDI1 (SEQ ID NOs:19 and 20, respectively) are shown in Table 9.

The nucleotide and amino acid sequences of the *Pichia pastoris* PDI1 (SEQ ID NOs:21 and 22, respectively) are shown in Table 9. Isolation of nucleic acid molecules comprising the *Pichia pastoris* PDI1 5' and 3' regions was performed by PCR amplification of the regions from *Pichia pastoris* genomic DNA. The 5' region was amplified using primers PB248: 5' ATGAA TTCAG GCCAT ATCGG CCATT GTTTA CTGTG CGCCC ACAGT AG 3' (SEQ ID NO: 3); PB249: 5' ATGTT TAAAC GTGAG GATTA CTGGT GATGA AAGAC 3' (SEQ ID NO: 4). The 3' region was amplified using primers PB250: 5' AGACT AGTCT ATTTG GAGAC ATTGA CGGAT CCAC 3' (SEQ ID NO: 5); PB251: 5' ATCTC GAGAG GCCAT GCAGG CCAAC CACAA GATGA ATCAA ATTTT G-3' (SEQ ID NO: 6). *Pichia pastoris* strain NRRL-Y11430 genomic DNA was used for PCR amplification. The PCR conditions were one cycle of 95° C. for two minutes, 25 cycles of 95° C. for 30 seconds, 55° C. for 30 seconds, and 72° C. for 2.5 minutes, and followed by one cycle of 72° C. for 10 minutes. The resulting PCR fragments, PpPDI1 (5') and PpPDI1 (3'), were separately cloned into plasmid vector pCR2.1 to make plasmid vectors pGLY620 and pGLY617, respectively. To construct pGLY678, DNA fragments PpARG3-5' and PpARG-3' of integration plasmid vector pGLY24, which targets the plasmid vector to *Pichia pastoris* ARG3 locus, were replaced with DNA fragments PpPDI (5') and PpPDI (3'), respectively, which targets the plasmid vector pGLY678 to the PDI1 locus and disrupts expression of the PDI1 locus.

The nucleic acid molecule encoding the human PDI was then cloned into plasmid vector pGLY678 to produce plasmid vector pGLY642 in which the nucleic acid molecule encoding the human PDI was placed under the control of the *Pichia pastoris* GAPDH promoter (PpGAPDH). Expression/integration plasmid vector pGLY642 was constructed by ligating a nucleic acid molecule (SEQ ID NO:17) encoding the *Saccharomyces cerevisiae* alpha mating factor pre-signal peptide (ScαMFpre-signal peptide (SEQ ID NO:18) having a NotI restriction enzyme site at the 5' end and a blunt 3' end and the expression cassette comprising the nucleic acid molecule encoding the human PDI released from plasmid vector pGLY618 with AfeI and PacI to produce a nucleic acid molecule having a blunt 5' end and a PacI site at the 3' end into plasmid vector pGLY678 digested with NotI and PacI. The resulting integration/expression plasmid vector pGLY642 comprises an expression cassette encoding a human PDI1/ScαMFpre-signal peptide fusion protein operably linked to the *Pichia pastoris* promoter and nucleic acid molecule sequences to target the plasmid vector to the *Pichia pastoris* PDI1 locus for disruption of the PDI1 locus and integration of the expression cassette into the PDI1 locus. FIGS. 2A and 2B illustrate the construction of plasmid vector pGLY642. The nucleotide and amino acid sequences of the ScαMFpre-signal peptide are shown in SEQ ID NOs:17 and 18, respectively.

Figure 3:
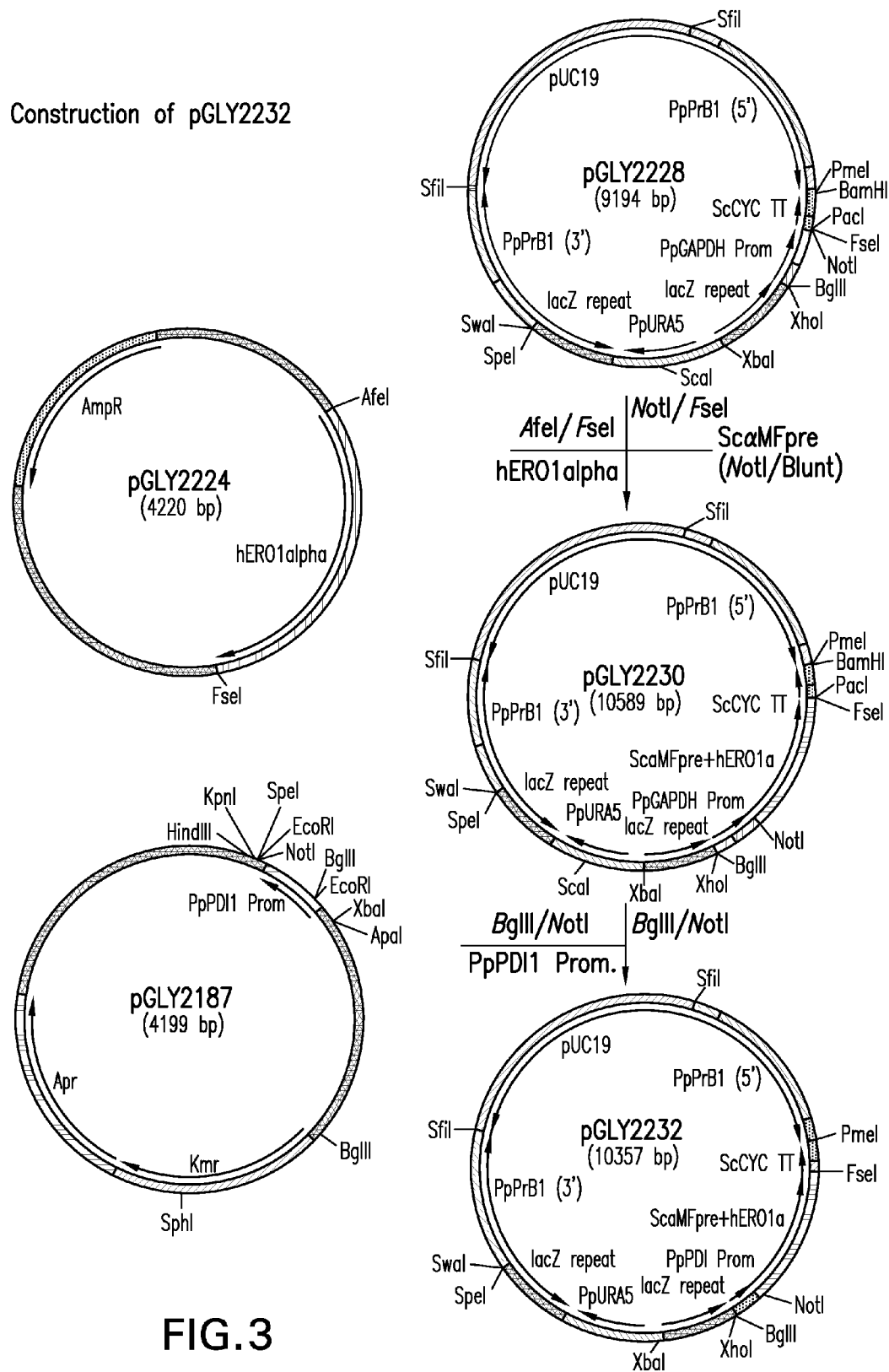
FIG. 3 illustrates the construction of plasmid vector pGLY2232 encoding the human ERO1α (hERO1α) and targeting the *Pichia pastoris* PrB1 locus.

Construction of expression/integration vector pGLY2232 encoding the human ERO1α protein was as follows and is shown in FIG. 3. A nucleic acid molecule encoding the human ERO1α protein was synthesized by GeneArt AG (Regensburg, Germany) and used to construct plasmid vector pGLY2224. The nucleotide and amino acid sequences of the human ERO1α protein (SEQ ID NOs:23 and 24, respectively) are shown in Table 9. The nucleic acid molecule encoding the human ERO1α protein was released from the plasmid vector using restriction enzymes AfeI and FseI and then ligated with a nucleic acid molecule encoding the ScαMPpre-signal peptide with 5' NotI and 3' blunt ends as above into plasmid vector pGLY2228 digested with NotI and FseI. Plasmid vector pGLY2228 also included nucleic acid molecules that included the 5' and 3' regions of the *Pichia pastoris* PRB1 gene (PpPRB1-5' and PpPRB1-3' regions, respectively). The resulting plasmid vector, pGLY2230 was digested with BglII and NotI and then ligated with a nucleic acid molecule containing the *Pichia pastoris* PDI1 promoter (PpPDI promoter) which had been obtained from plasmid vector pGLY2187 digested with BglII and NotI. The nucleotide sequence of the PpPDI promoter is 5'-AACACGAA-CACTGTAAA TAGAATAAAAGAAAACTTGGATAGTA-GAACTTCAATGTAGTGTTTCTATTGTCTTAC GCGGCTCTTTAGATTGCAATCCCCA-GAATGGAATCGTCCATCTTTCTCAACCCACTCA AAGATAATCTACCAGACATACCTACGC-CCTCCATCCCAGCACCACGTCGCGATCACC CCTAAAACTTCAATAATTGAACACG-TACTGATTTCCAAACCTTCTTCTTCTTCCTATC TATAAGA-3' (SEQ ID NO:31). The resulting plasmid vector, pGLY2232, is an expression/integration vector that contains an expression cassette that encodes the human ERO1α fusion protein under control of the *Pichia pastoris* PDI1 promoter and includes the 5' and 3' regions of the *Pichia pastoris* PRB1 gene to target the plasmid vector to the PRB1 locus of genome for disruption of the PRB1 locus and integration of the expression cassette into the PRB1 locus. FIG. 3 illustrates the construction of plasmid vector pGLY2232.

Figure 4:
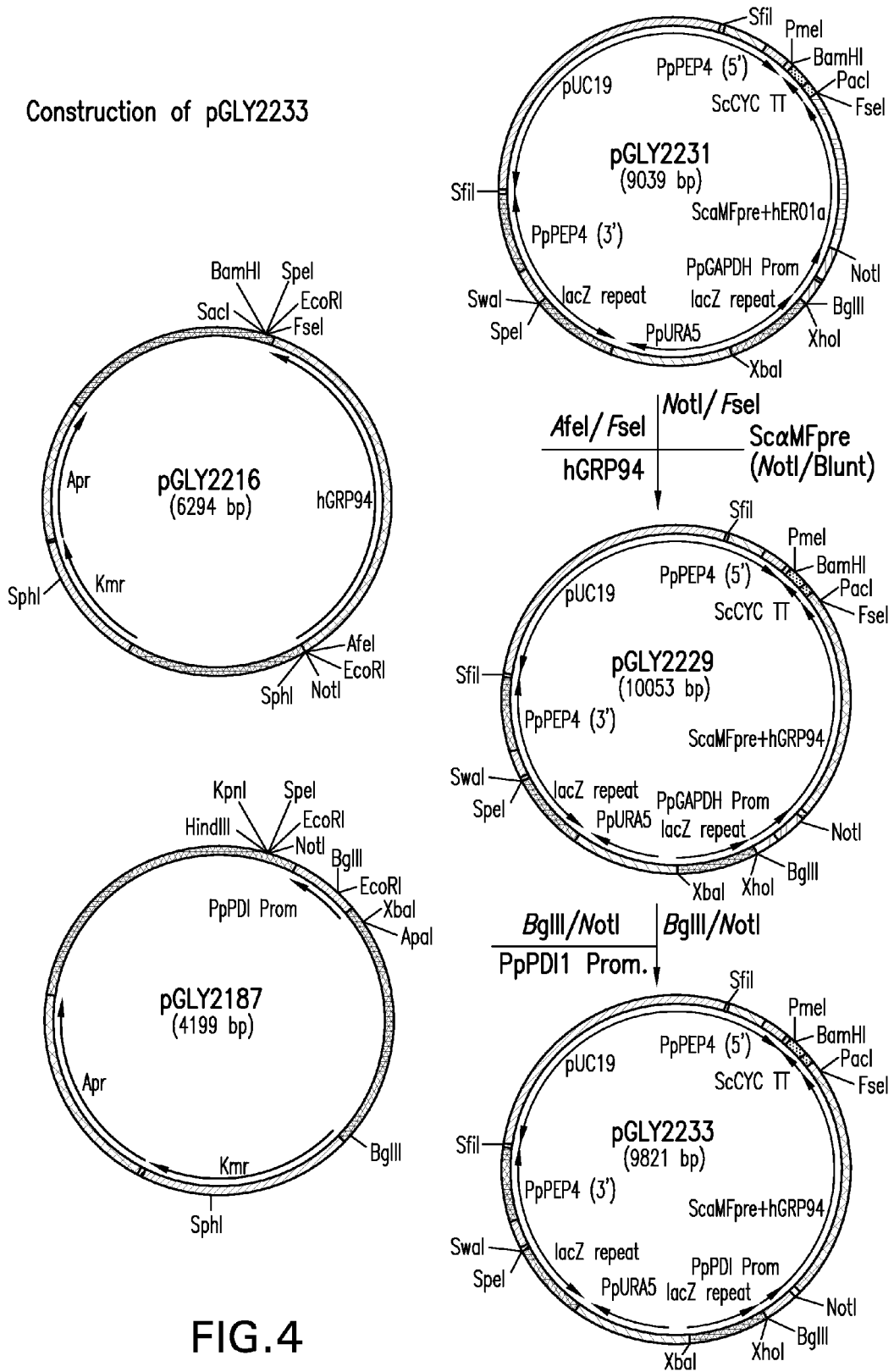
FIG. 4 illustrates the construction of plasmid vector pGLY2233 encoding the human GRP94 and targeting the *Pichia pastoris* PEP4 locus.

Construction of expression/integration vector pGLY2233 encoding the human GRP94 protein was as follows and is shown in FIG. 4. The human GRP94 was PCR amplified from human liver cDNA (BD Bioscience) with the primers hGRP94/UP1: 5'-AGCGC TGACG ATGAA GTTGA TGTGG ATGGT ACAGT AG-3'; (SEQ ID NO: 15); and hGRP94/LP1: 5'-GGCCG GCCTT ACAAT TCATC ATGTT CAGCT GTAGA TTC 3'; (SEQ ID NO: 16). The PCR conditions were one cycle of 95° C. for two minutes, 25 cycles of 95° C. for 20 seconds, 55° C. for 20 seconds, and 72° C. for 2.5 minutes, and followed by one cycle of 72° C. for 10 minutes. The PCR product was cloned into plasmid vector pCR2.1 to make plasmid vector pGLY2216. The nucleotide and amino acid sequences of the human GRP94 (SEQ ID NOs:25 and 26, respectively) are shown in Table 9.

The nucleic acid molecule encoding the human GRP94 was released from plasmid vector pGLY2216 with AfeI and FseI. The nucleic acid molecule was then ligated to a nucleic acid molecule encoding the ScαMPpre-signal peptide having NotI and blunt ends as above and plasmid vector pGLY2231 digested with NotI and FseI carrying nucleic acid molecules comprising the *Pichia pastoris* PEP4 5' and 3' regions (PpPEP4-5' and PpPEP4-3' regions, respectively) to make plasmid vector pGLY2229. Plasmid vector pGLY2229 was digested with BglII and NotI and a DNA fragment containing the PpPDI1 promoter was removed from plasmid vector pGLY2187 with BglII and NotI and the DNA fragment ligated into pGLY2229 to make plasmid vector pGLY2233. Plasmid vector pGLY2233 encodes the human GRP94 fusion protein under control of the *Pichia pastoris* PDI promoter and includes the 5' and 3' regions of the *Pichia pastoris* PEP4 gene to target the plasmid vector to the PEP4 locus of genome for disruption of the PEP4 locus and integration of the expression cassette into the PEP4 locus. FIG. 4 illustrates the construction of plasmid vector pGLY2233.

Figure 5:
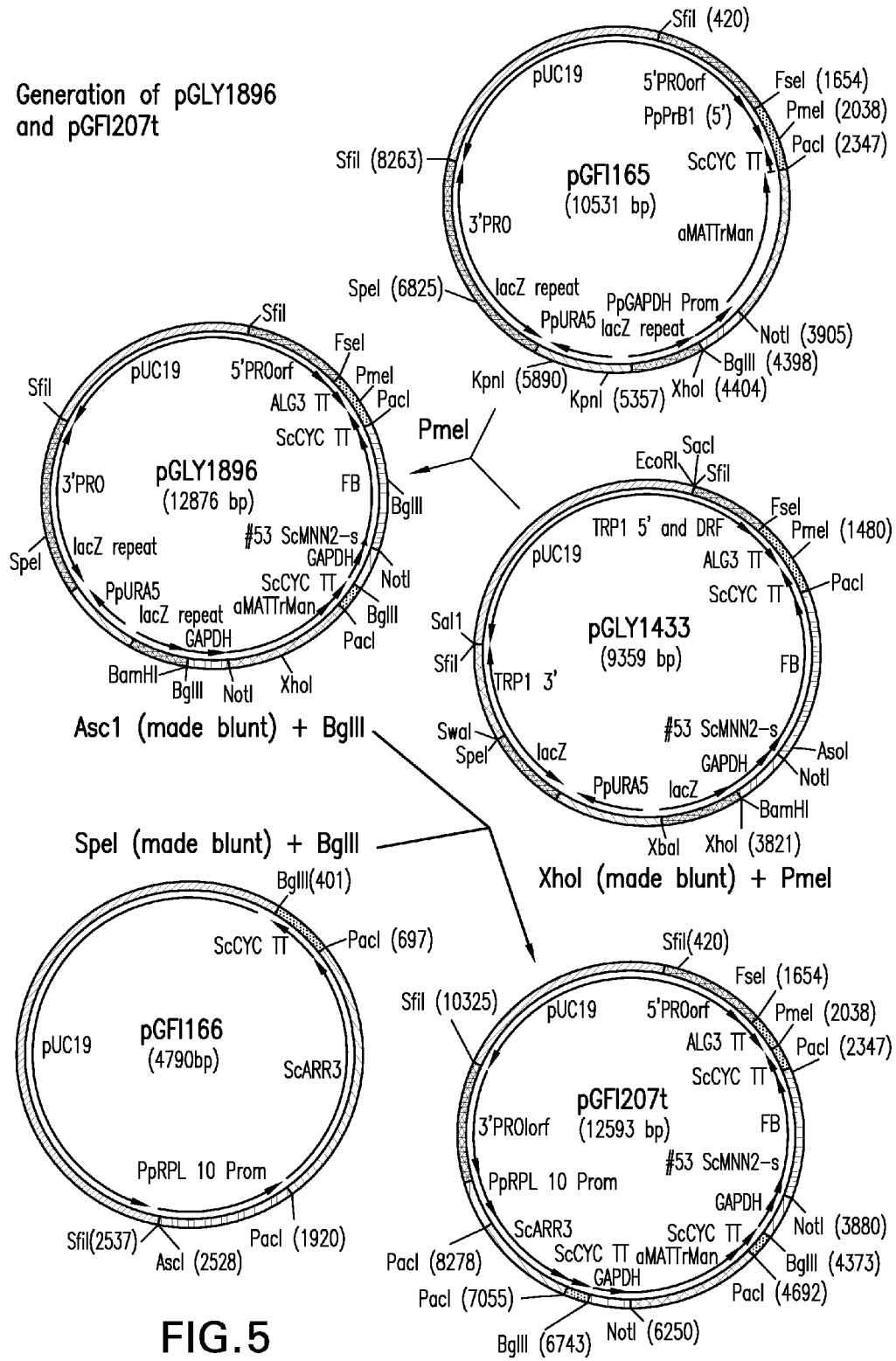
FIG. 5 illustrates the construction of plasmid vectors pGLY1896 and pGFI207t encoding the *T. reesei* α-1,2 mannosidase (TrMNS1) and mouse α-1,2 mannosidase IA (FB53) and targeting the *Pichia pastoris* PRO locus.

Construction of plasmid vectors pGLY1162, pGLY1896, and pGFI207t was as follows. All *Trichoderma reesei* α-1,2-mannosidase expression plasmid vectors were derived from pGFI165, which encodes the *T. reesei* α-1,2-mannosidase catalytic domain (See published International Application No. WO2007061631) fused to *S. cerevisiae* αMATpre signal peptide herein expression is under the control of the *Pichia pastoris* GAP promoter and wherein integration of the plasmid vectors is targeted to the *Pichia pastoris* PRO1 locus and selection is using the *Pichia pastoris* URA5 gene. A map of plasmid vector pGFI165 is shown in FIG. 5.

Figure 6:
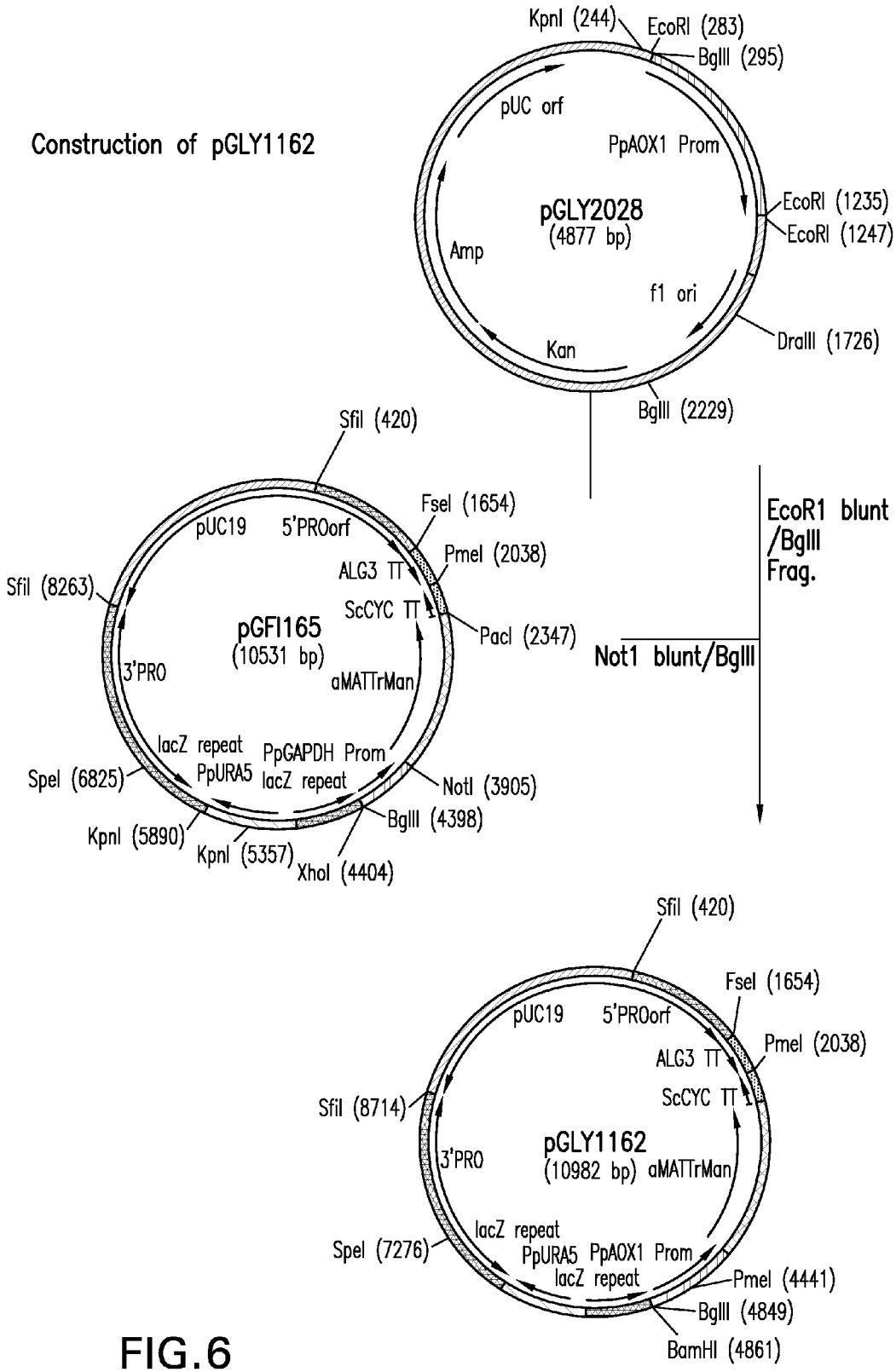
FIG. 6 illustrates the construction of plasmid vector pGLY1162 encoding the *T. reesei* α-1,2 mannosidase (TrMNS1) and targeting the *Pichia pastoris* PRO locus.

Plasmid vector pGLY1162 was made by replacing the GAP promoter in pGFI165 with the *Pichia pastoris* AOX1 (PpAOX1) promoter. This was accomplished by isolating the PpAOX1 promoter as an EcoRI (made blunt)-BglII fragment from pGLY2028, and inserting into pGFI165 that was digested with NotI (made blunt) and BglII. Integration of the plasmid vector is to the *Pichia pastoris* PRO1 locus and selection is using the *Pichia pastoris* URA5 gene. A map of plasmid vector pGLY1162 is shown in FIG. 6.

Plasmid vector pGLY1896 contains an expression cassette encoding the mouse α-1,2-mannosidase catalytic domain fused to the *S. cerevisiae* MNN2 membrane insertion leader peptide fusion protein (See Choi et al., Proc. Natl. Acad. Sci. USA 100: 5022 (2003)) inserted into plasmid vector pGFI165 (FIG. 5). This was accomplished by isolating the GAPp-ScMNN2-mouse MNSI expression cassette from pGLY1433 digested with XhoI (and the ends made blunt) and PmeI, and inserting the fragment into pGFI165 that digested with PmeI. Integration of the plasmid vector is to the *Pichia pastoris* PRO1 locus and selection is using the *Pichia pastoris* URA5 gene. A map of plasmid vector pGLY1896 is shown in FIG. 5.

Plasmid vector pGFI207t is similar to pGLY1896 except that the URA5 selection marker was replaced with the *S. cerevisiae* ARR3 (ScARR3) gene, which confers resistance to arsenite. This was accomplished by isolating the ScARR3 gene from pGFI166 digested with AscI and the AscI ends made blunt) and BglII, and inserting the fragment into pGLY1896 that digested with SpeI and the SpeI ends made blunt and BglII. Integration of the plasmid vector is to the *Pichia pastoris* PRO1 locus and selection is using the *Saccharomyces cerevisiae* ARR3 gene. A map of plasmid vector pGFI207t is shown in FIG. 5.

Figure 7:
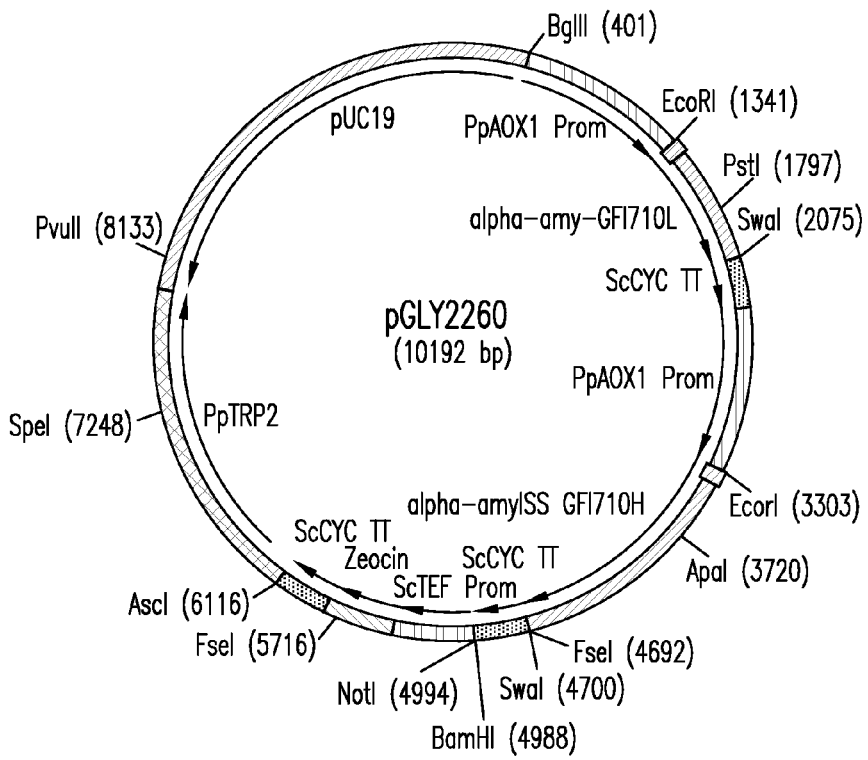
FIG. 7 is a map of plasmid vectors pGLY2260 and pGLY2261 encoding the anti-DKK1 antibody heavy chain (GFI710H) and light chain (GFI710L) and targeting the *Pichia pastoris* TRP2 locus and targeting the *Pichia pastoris* TRP2 locus.
Figure 7:
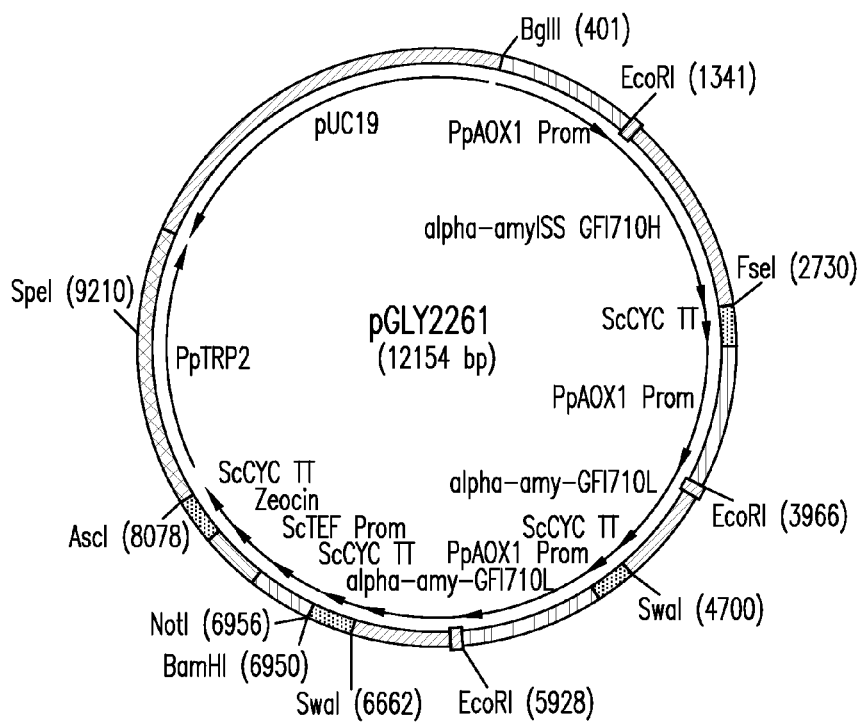

Construction of anti-DKK1 antibody expression/integration plasmid vector pGLY2260 and pGLY2261 (FIG. 7) was as follows. Anti-DKK1 antibodies are antibodies that recognize Dickkopf protein 1, a ligand involved in the Wnt signaling pathway. To generate expression/integration plasmid vectors pGLY2260 and pGLY2261 encoding an anti-DKK1 antibody, codon-optimized nucleic acid molecules encoding heavy chain (HC; fusion protein containing VH+IgG$_2$ m4) and light chain (LC; fusion protein containing VL+Lλ constant region) fusion proteins, each in frame with a nucleic acid molecule encoding an α-amylase (from *Aspergillus niger*) signal peptide were synthesized by GeneArt AG. The nucleotide and amino acid sequences for the a-amylase signal peptide are shown in SEQ ID NOs:48 and 49. The nucleotide sequence of the HC is shown in SEQ ID NO:27 and the amino acid sequence is shown in SEQ ID NO:28. The nucleotide sequence of the LC is shown in SEQ ID NO:29 and the amino acid sequence is shown in SEQ ID NO:30. The IgG$_2$ m4 isotype has been disclosed in U.S. Published Application No. 2007/0148167 and U.S. Published Application No. 2006/0228349. The nucleic acid molecules encoding the HC and LC fusion proteins were separately cloned using unique 5'-EcoRI and 3'-FseI sites into expression plasmid vector pGLY1508 to form plasmid vectors pGLY1278 and pGLY1274, respectively. These plasmid vectors contained the Zeocin-resistance marker and TRP2 integration sites and the *Pichia pastoris* AOX1 promoter operably linked to the nucleic acid molecules encoding the HC and LC fusion proteins. The LC fusion protein expression cassette was removed from pGLY1274 with BglII and BamHI and cloned into pGLY1278 digested with BglII to generate plasmid vector pGLY2260, which encodes the HC and LC fusion proteins and targets the expression cassettes to the TRP2 locus for integration of the expression cassettes into the TRP2 locus. The plasmid vector pGLY2261 contains an additional LC in plasmid vector pGLY2260. (FIG. 7).

Yeast transformations with the above expression/integration vectors were as follows. *Pichia pastoris* strains were grown in 50 mL YPD media (yeast extract (1%), peptone (2%), dextrose (2%)) overnight to an OD of between about 0.2 to 6. After incubation on ice for 30 minutes, cells were pelleted by centrifugation at 2500-3000 rpm for 5 minutes. Media was removed and the cells washed three times with ice cold sterile 1 M sorbitol before resuspension in 0.5 ml ice cold sterile 1M sorbitol. Ten μL linearized DNA (5-20 mg) and 100 μL cell suspension was combined in an electroporation cuvette and incubated for 5 minutes on ice. Electroporation was in a Bio-Rad GenePulser Xcell following the preset *Pichia pastoris* protocol (2 kV, 25 μF, 200Ω), immediately followed by the addition of 1 mL YPDS recovery media (YPD media plus 1 M sorbitol). The transformed cells were allowed to recover for four hours to overnight at room temperature (24° C.) before plating the cells on selective media.

Figure 1B:
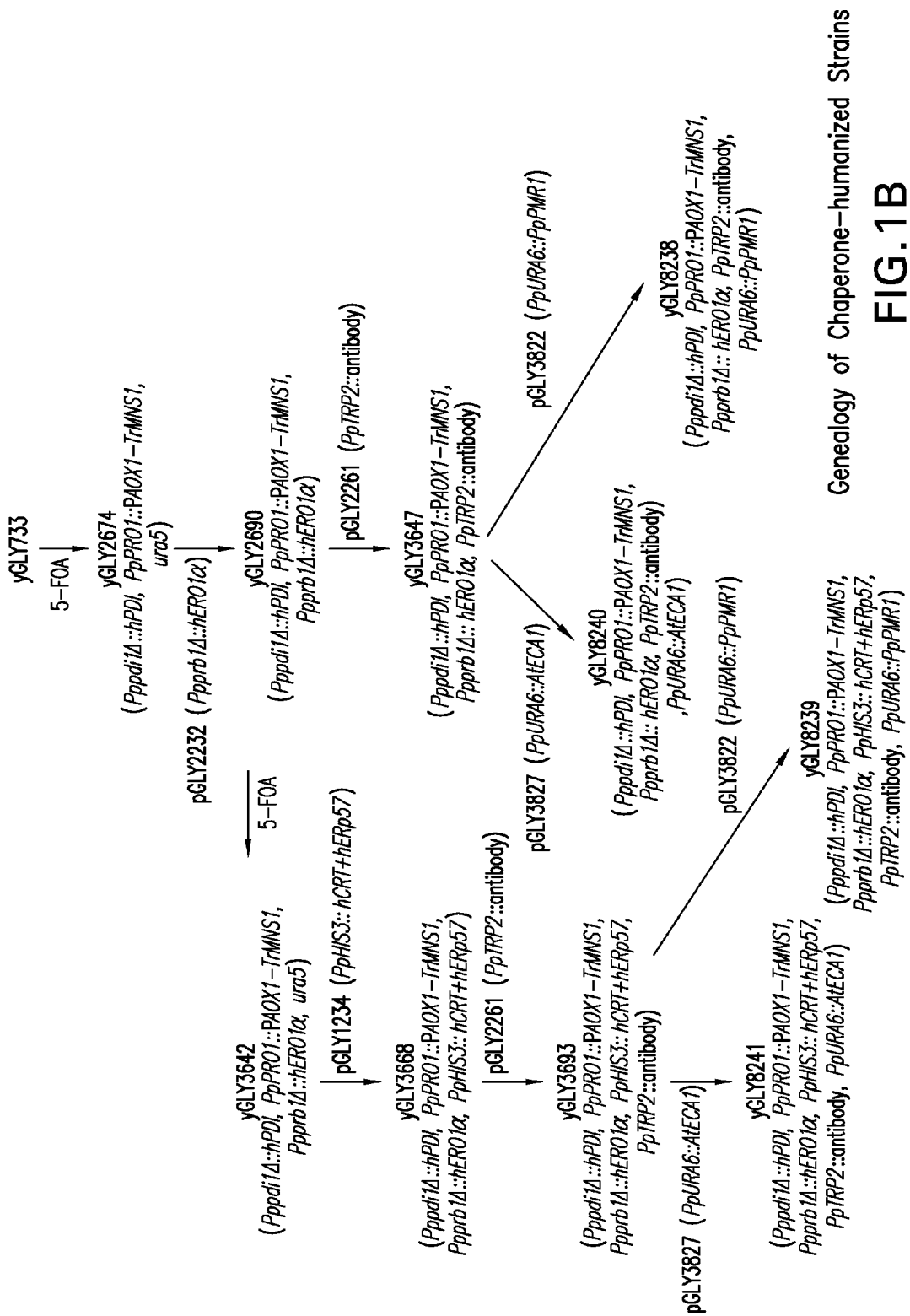

Generation of Cell Lines was as follows and is shown in FIGS. 1A and 1B. The strain yGLY24-1 (ura5Δ::MET1 och1Δ::lacZ bmt4Δ::lacZ/KlMNN2-2/mnn4L1Δ::lacZ/ MmSLC35A3 pnolΔmnn4Δ::lacZ met16Δ::lacZ), was constructed using methods described earlier (See for example, Nett and Gerngross, Yeast 20:1279 (2003); Choi et al., Proc. Natl. Acad. Sci. USA 100:5022 (2003); Hamilton et al., Science 301:1244 (2003)). The BMT2 gene has been disclosed in Mille et al., J. Biol. Chem. 283: 9724-9736 (2008) and U.S. Published Application No. 20060211085. The PNO1 gene has been disclosed in U.S. Pat. No. 7,198,921 and the mnn4L1 gene (also referred to as mnn4b) has been disclosed in U.S. Pat. No. 7,259,007. The mnn4 refers to mnn4L2 or mnn4a. In the genotype, KlMNN2-2 is the *Kluveromyces lactis* GlcNAc transporter and MmSLC35A3 is the *Mus musculus* GlcNAc transporter. The URA5 deletion renders the yGLY24-1 strain auxotrophic for uracil (See U.S. Published application No. 2004/0229306) and was used to construct the humanized chaperone strains that follow. While the various expression cassettes were integrated into particular loci of the *Pichia pastoris* genome in the examples herein, it is understood that the operation of the invention is independent of the loci used for integration. Loci other than those disclosed herein can be used for integration of the expression cassettes. Suitable integration sites include those enumerated in U.S. Published application No. 20070072262 and include homologs to loci known for *Saccharomyces cerevisiae* and other yeast or fungi.

Control strain yGLY645 (PpPDI1) was constructed. Strain yGLY645 expresses both a *Trichoderma Reesei* mannosidasel (TrMNS1) and a mouse mannosidase IA (MuMNS1A), each constitutively expressed under the control of a PpGAPDH promoter, with the native *Pichia pastoris* PDI1 locus intact. Strain yGLY645 was generated from strain yGLY24-1 by transforming yGLY24-1 with plasmid vector pGLY1896, which targeted the plasmid vector to the Proline 1 (PRO1) locus in the *Pichia* genome. Plasmid vector pGLY1896 contains expression cassettes encoding the *Trichoderma Reesei* mannosidase 1 (TrMNS 1) and the mouse mannosidase IA (FB53, MuMNS1A), each constitutively expressed under the control of a PpGAPDH promoter.

Strains yGLY702 and yGLY704 were generated in order to test the effectiveness of the human PDI expressed in *Pichia pastoris* cells in the absence of the endogenous *Pichia pastoris PDI*1 gene. Strains yGLY702 and yGLY704 (hPDI) were constructed as follows. Strain yGLY702 was generated by transforming yGLY24-1 with plasmid vector pGLY642 containing the expression cassette encoding the human PDI under control of the constitutive PpGAPDH promoter. Plasmid vector pGLY642 also contained an expression cassette encoding the *Pichia pastoris* URA5, which rendered strain yGLY702 prototrophic for uracil. The URA5 expression cassette was removed by counterselecting yGLY702 on 5-FOA plates to produce strain yGLY704 in which, so that the *Pichia pastoris* PDI1 gene has been stably replaced by the human PDI gene and the strain is auxotrophic for uracil.

The replacement of the *Pichia pastoris* PDI1 with the human PDI using plasmid vector pGLY642 was confirmed by colony PCR using the following primers specific to only the PpPDI1 ORF; PpPDI/UPi-1,5'-GGTGA GGTTG AGGTC CCAAG TGACT ATCAA GGTC-3'; (SEQ ID NO: 7); PpPDI/LPi-1,5'-GACCT TGATA GTCAC TTGGG ACCTC AACCT CACC-3'; (SEQ ID NO: 8); PpPDI/UPi-2,5' CGCCA ATGAT GAGGA TGCCT CTTCA AAGGT TGTG-3'; (SEQ ID NO: 9); and PpPDI/LPi-2,5'-CACAA CCTTT GAAGA GGCAT CCTCA TCATT GGCG-3'; (SEQ ID NO: 10). Thus, the absence of PCR product indicates the knockout of PpPDI1. The PCR conditions were one cycle of 95° C. for two minutes, 25 cycles of 95° C. for 20 seconds, 58° C. for 20 seconds, and 72° C. for one minute, and followed by one cycle of 72° C. for 10 minutes.

Additional PCR was used to confirm the double crossover of pGLY642 at the PpPDI1 locus using PCR primers; PpPDI-5'/UP, 5'-GGCGA TTGCA TTCGC GACTG TATC-3; (SEQ ID NO: 11); and, hPDI-3'/LP 5'-CCTAG AGAGC GGTGG CCAAG ATG-3; (SEQ ID NO: 12). PpPDI-5'/UP primes the upstream region of PpPDI1 that is absent in PpPDI1 (5') of pGY642 and hPDI-3'/LP primes human PDI ORF in pGLY642. The PCR conditions were one cycle of 95° C. for two minutes, 25 cycles of 95° C. for 20 seconds, 50° C. for 30 seconds, and 72° C. for 2.5 minutes, and followed by one cycle of 72° C. for 10 minutes.

The integration efficiency of a plasmid vector as a knockout (i.e., a double cross-over event) or as a 'roll-in' (i.e., a single integration of the plasmid vector into the genome, can be dependent upon a number of factors, including the number and length of homologous regions between vectors and the corresponding genes on host chromosomal DNA, selection markers, the role of the gene of interest, and the ability of the knocked-in gene to complement the endogenous function. The inventors found that in some instances pGLY642 was integrated as a double cross-over, resulting in replacement of the endogenous PpPDI gene with human PpPDI, while in other cases, the pGLY642 plasmid vector was integrated as a single integration, resulting in presence of both the endogenous PpPDI1 gene and a human PpPDI gene. In order to distinguish between these events, the inventors utilized PCR primers of Sequence ID Nos. 11 through 14, described herein. If the PpPDI gene has been retained after integration of the pGLY642 plasmid vector, PpPDI-5'/UP and hPDI-3'/LP, directed to the internal PpPDI coding sequence, will result in an amplification product and a corresponding band. In the event of a knockout or double cross-over, these primers will not result in any amplification product and no corresponding band will be visible.

The roll-in of pGLY642 was confirmed with the primers; PpPDI/UP1-1 (SEQ ID NO: 7) and PpPDI/LPi-1 (SEQ ID NO: 8) encoding PpPDI1, and hPDPUP, 5'-GTGGC CACAC CAGGG GGCAT GGAAC-3'; (SEQ ID NO: 13); and hPDI-3'/LP, 5'-CCTAG AGAGC GGTGG CCAAG ATG-3'; (SEQ ID NO: 14); encoding human PDI. The PCR conditions were one cycle of 95° C. for two minutes, 25 cycles of 95° C. for 20 seconds, 58° C. for 20 seconds, and 72° C. for one minute, and followed by 1 cycle of 72° C. for 10 minutes for PpPDI1, and 1 cycle of 95° C. for two minutes, 25 cycles of 95° C. for 20 seconds, 50° C. for 30 seconds, and 72° C. for 2.5 minutes, and followed by one cycle of 72° C. for 10 minutes for human PDI.

Strain yGLY733 was generated by transforming with plasmid vector pGLY1162, which comprises an expression cassette that encodes the *Trichoderma Reesei* mannosidase (TrMNS1) operably linked to the *Pichia pastoris* AOX1 promoter (PpAOX1-TrMNS1), into the PRO1 locus of yGLY704. This strain has the gene encoding the *Pichia pastoris* PDI1 replaced with the expression cassette encoding the human PDI, has the PpAOX1-TrMNS1 expression cassette integrated into the PRO1 locus, and is a URA5 prototroph. The PpAOX1 promoter allows overexpression when the cells are grown in the presence of methanol.

Strain yGLY762 was constructed by integrating expression cassettes encoding TrMNS1 and mouse mannosidase IA (MuMNS1A), each operably linked to the *Pichia pastoris* GAPDH promoter in plasmid vector pGFI207t into strain yGLY733 at the 5' PRO1 locus UTR in *Pichia pastoris* genome. This strain has the gene encoding the *Pichia pastoris* PDI1 replaced with the expression cassette encoding the human PDI, has the PpGAPDH-TrMNS1 and PpGAPDH-MuMNS1A expression cassettes integrated into the PRO1 locus, and is a URA5 prototroph.

Strain yGLY2263 was generated by transforming strain yGLY645 with integration/expression plasmid pGLY2260, which targets an expression cassette encoding the anti-DKK1 antibody to the TRP2 locus.

Strain yGLY2674 was generated by counterselecting yGLY733 on 5-FOA plates. This strain has the gene encoding the *Pichia pastoris* PD1 replaced with the expression cassette encoding the human PDI, has the PpAOX1-TrMNS1 expression cassette integrated into the PRO1 locus, and is a URA5 auxotroph.

Strain yGLY2677 was generated by counterselecting yGLY762 on 5-FOA plates. This strain has the gene encoding the *Pichia pastoris* PDI1 replaced with the expression cassette encoding the human PDI, has the PpAOX1-TrMNS1 expression cassette integrated into the PRO1 locus, has the PpGAPH-TrMNS1 and PpGAPDH-MuMNS1A expression cassettes integrated into the PRO1 locus, and is a URA5 auxotroph.

Strains yGLY2690 was generated by integrating plasmid vector pGLY2232, which encodes the human ERO 1a protein, into the PRB1 locus. This strain has the gene encoding the *Pichia pastoris* PDI1 replaced with the expression cassette encoding the human PDI, has the PpAOX1-TrMNS1 expression cassette integrated into the PRO1 locus, the human ERO1α expression cassette integrated into the PRB1 locus, and is a URA5 prototroph.

Strains yGLY2696 was generated by integrating plasmid vector pGLY2233, which encodes the human GRP94 protein, into the PEP4 locus. This strain has the gene encoding the

*Pichia pastoris* PDI1 replaced with the expression cassette encoding the human PDI, has the PpAOX1-TrMNS1 expression cassette integrated into the PRO1 locus, has the PpGAPDH-TrMNS1 and PpGAPDH-MuMNS1A expression cassettes integrated into the PRO1 locus, has the human GRP94 integrated into the PEP4 locus, and is a URA5 prototroph.

Strain yGLY3628 was generated by transforming strain yGLY2696 with integration/expression plasmid pGLY2261, which targets an expression cassette encoding the anti-DKK1 antibody to the TRP2 locus.

Strain yGLY3647 was generated by transforming strain yGLY2690 with integration/expression plasmid pGLY2261, which targets an expression cassette encoding the anti-DKK1 antibody to the TRP2 locus.

Table 1 shows that replacing the gene encoding the *Pichia pastoris* PDI1 with an expression cassette encoding the human PDI in yeast genetically engineered to produce glycoproteins that have predominantly $Man_5GlcNAc_2$ N-glycans effects a reduction in O-glycosylation occupancy and an increase in N-glycosylation.

TABLE 1

| GS2.0 Strain | yGLY2263 (control) | yGLY3647 | yGLY3628 |
|---|---|---|---|
| *Pichia pastoris* PDI1 | Wild-type | Knockout | Knockout |
| Human PDI | None | Overexpressed | Overexpressed |
| Human ERO1α | None | Expressed | None |
| Human GRP94 | None | None | Expressed |
| *Pichia pastoris* PRB1 | Intact | Knockout | Intact |
| *Pichia pastoris* PEP4 | Intact | Intact | Knockout |
| O-glycan (Occupancy: H2L2) | 23.7 | 9.2 | 10.0 |

EXAMPLE 2

Cell Growth conditions of the transformed strains for antibody production was generally as follows.

Protein expression for the transformed yeast strains was carried out at in shake flasks at 24° C. with buffered glycerol-complex medium (BMGY) consisting of 1% yeast extract, 2% peptone, 100 mM potassium phosphate buffer pH 6.0, 1.34% yeast nitrogen base, $4 \times 10^{-5}$% biotin, and 1% glycerol. The induction medium for protein expression was buffered methanol-complex medium (BMMY) consisting of 1% methanol instead of glycerol in BMGY. Pmt inhibitor Pmti-3 in methanol was added to the growth medium to a final concentration of 18.3 µM at the time the induction medium was added. Cells were harvested and centrifuged at 2,000 rpm for five minutes.

SixFors Fermentor Screening Protocol followed the parameters shown in Table 2.

TABLE 2

SixFors Fermentor Parameters

| Parameter | Set-point | Actuated Element |
|---|---|---|
| pH | 6.5 ± 0.1 | 30% NH₄OH |
| Temperature | 24 ± 0.1 | Cooling Water & Heating Blanket |
| Dissolved O2 | n/a | Initial impeller speed of 550 rpm is ramped to 1200 rpm over first 10 hr, then fixed at 1200 rpm for remainder of run |

At time of about 18 hours post-inoculation, SixFors vessels containing 350 mL media A (See Table 6 below) plus 4% glycerol were inoculated with strain of interest. A small dose (0.3 mL of 0.2 mg/mL in 100% methanol) of Pmti-3 (5-[[3-(1-Phenyl-2-hydroxy)ethoxy)-4-(2-phenylethoxy)]phenyl] methylene]-4-oxo-2-thioxo-3-thiazolidineacetic Acid) (See Published International Application No. WO 2007061631) was added with inoculum. At time about 20 hour, a bolus of 17 mL 50% glycerol solution (Glycerol Fed-Batch Feed, See Table 7 below) plus a larger dose (0.3 mL of 4 mg/mL) of Pmti-3 was added per vessel. At about 26 hours, when the glycerol was consumed, as indicated by a positive spike in the dissolved oxygen (DO) concentration, a methanol feed (See Table 6 below) was initiated at 0.7 mL/hr continuously. At the same time, another dose of Pmti-3 (0.3 mL of 4 mg/mL stock) was added per vessel. At time about 48 hours, another dose (0.3 mL of 4 mg/mL) of Pmti-3 was added per vessel. Cultures were harvested and processed at time about 60 hours post-inoculation.

TABLE 3

Composition of Media A

| | |
|---|---|
| Martone L-1 | 20 g/L |
| Yeast Extract | 10 g/L |
| KH₂PO₄ | 11.9 g/L |
| K₂HPO₄ | 2.3 g/L |
| Sorbitol | 18.2 g/L |
| Glycerol | 40 g/L |
| Antifoam Sigma 204 | 8 drops/L |
| 10X YNB w/Ammonium Sulfate w/o Amino Acids (134 g/L) | 100 mL/L |
| 250X Biotin (0.4 g/L) | 10 mL/L |
| 500X Chloramphenicol (50 g/L) | 2 mL/L |
| 500X Kanamycin (50 g/L) | 2 mL/L |

TABLE 4

Glycerol Fed-Batch Feed

| | |
|---|---|
| Glycerol | 50% m/m |
| PTM1 Salts (see Table IV-E below) | 12.5 mL/L |
| 250X Biotin (0.4 g/L) | 12.5 mL/L |

TABLE 5

Methanol Feed

| | |
|---|---|
| Methanol | 100% m/m |
| PTM1 Salts | 12.5 mL/L |
| 250X Biotin (0.4 g/L) | 12.5 mL/L |

TABLE 6

PTM1 Salts

| | |
|---|---|
| CuSO4—5H2O | 6 g/L |
| NaI | 80 mg/L |
| MnSO4—7H2O | 3 g/L |
| NaMoO4—2H2O | 200 mg/L |
| H3BO3 | 20 mg/L |
| CoCl2—6H2O | 500 mg/L |
| ZnCl2 | 20 g/L |
| FeSO4—7H2O | 65 g/L |
| Biotin | 200 mg/L |
| H2SO4 (98%) | 5 mL/L |

O-glycan determination was performed using a Dionex-HPLC (HPAEC-PAD) as follows. To measure O-glycosylation reduction, protein was purified from the growth medium using protein A chromatography (Li et al. Nat. Biotechnol.

24(2):210-5 (2006)) and the O-glycans released from and separated from protein by alkaline elimination (beta-elimination) (Harvey, Mass Spectrometry Reviews 18: 349-451 (1999)). This process also reduces the newly formed reducing terminus of the released O-glycan (either oligomannose or mannose) to mannitol. The mannitol group thus serves as a unique indicator of each O-glycan. 0.5 nmole or more of protein, contained within a volume of 100 μL PBS buffer, was required for beta elimination. The sample was treated with 25 μL alkaline borohydride reagent and incubated at 50° C. for 16 hours. About 20 μL arabitol internal standard was added, followed by 10 μL glacial acetic acid. The sample was then centrifuged through a Millipore filter containing both SEPA-BEADS and AG 50W-X8 resin and washed with water. The samples, including wash, were transferred to plastic autosampler vials and evaporated to dryness in a centrifugal evaporator. 150 μL 1% AcOH/MeOH was added to the samples and the samples evaporated to dryness in a centrifugal evaporator. This last step was repeated five more times. 200 μL of water was added and 100 μL of the sample was analyzed by high pH anion-exchange chromatography coupled with pulsed electrochemical detection-Dionex HPLC (HPAEC-PAD). Average O-glycan occupancy was determined based upon the amount of mannitol recovered.

EXAMPLE 3

This example demonstrates that occupancy of O-glycans in proteins produced in the above strains expressing the human PDI in place of the *Pichia pastoris* PDI1 can be significantly reduced when either the *Pichia pastoris* Golgi $Ca^{2+}$ ATPase (PpPMR1) or the *Arabidopsis thaliana* ER $Ca^{2+}$ ATPase (AtECA1) is overexpressed in the strains. In this example, the effect is illustrated using glycoengineered *Pichia pastoris* strains that produce antibodies having predominantly $Man_5GlcNAc_2$ N-glycans.

Figure 8:
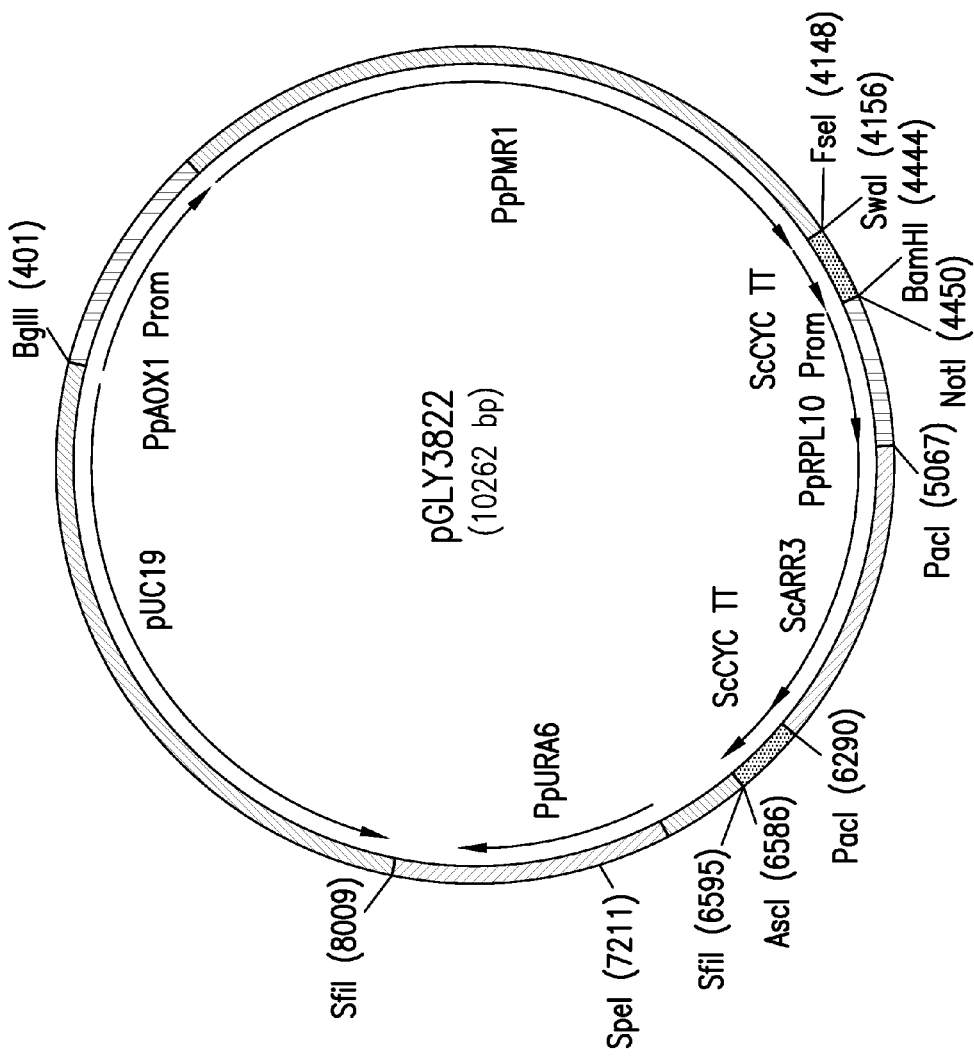
FIG. 8 is a map of plasmid vector pGLY3822 encoding the *Pichia pastoris* PMR1 and targeting the *Pichia pastoris* URA6 locus.

An expression cassette encoding the PpPMR1 gene was constructed as follows. The open reading frame of *P. pastoris* Golgi $Ca^{2+}$ ATPase (PpPMR1) was PCR amplified from *P. pastoris* NRRL11430 genomic DNA using the primers (PpPMR1/UP: 5'-GAATTCATGACAGCTAATGAAAATC-CTTTTGAGAATGAG-3' (SEQ ID NO:36) and PpPMR1/LP: 5'-GGCCGGCCTCAAACAGCCATGCTGTATC-CATTGTATG-3' (SEQ ID NO:37). The PCR conditions were one cycle of 95° C. for two minutes; five cycles of 95° C. for 10 seconds, 52° C. for 20 seconds, and 72° C. for 3 minutes; 20 cycles of 95° C. for 10 seconds, 55° C. for 20 seconds, and 72° C. for 3 minutes; followed by 1 cycle of 72° C. for 10 minutes. The resulting PCR product was cloned into pCR2.1 and designated pGLY3811. PpPMR1 was removed from pGLY3811 by digesting with plasmid with PstI and FseI and the PstI end had been made blunt with T4 DNA polymerase prior to digestion with FseI. The DNA fragment encoding the PpPMR1 was cloned into pGFI30t digested with EcoRI with the ends made blunt with T4 DNA polymerase and FseI to generate pGLY3822 in which the PpPMR1 is operably linked to the AOX1 promoter. Plasmid pGLY3822 targets the *Pichia pastoris* URA6 locus. Plasmid pGLY3822 is shown in FIG. 8. The DNA sequence of PpPMR1 is set forth in SEQ ID NO:32 and the amino acid sequence of the PpPMR1 is shown in SEQ ID NO:33.

Figure 9:
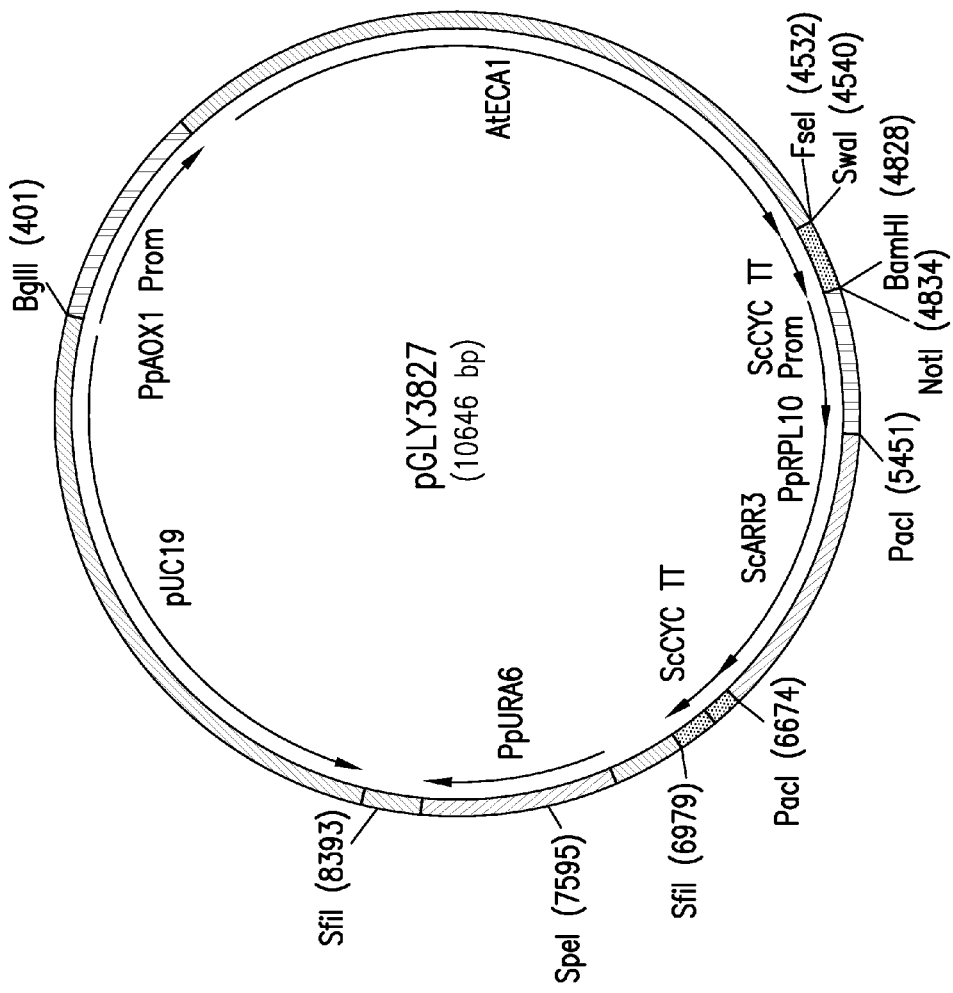
FIG. 9 is a map of plasmid vector pGLY3827 encoding the *Arabidopsis thaliana* ECA1 (AtECA1) and targeting the *Pichia pastoris* URA6 locus.

An expression cassette encoding the *Arabidopsis thaliana* ER $Ca^{2+}$ ATPase (AtECA1) was constructed as follows. A DNA encoding AtECA1 was synthesized from GeneArt AG (Regensburg, Germany) and cloned to make pGLY3306. The synthesized AtECA1 was removed from pGLY3306 by digesting with MlyI and FseI and cloning the DNA fragment encoding the AtECA1 into pGFI30t digested with EcoRI with the ends made blunt with T4 DNA polymerase and FseI to generate integration/expression plasmid pGLY3827. Plasmid pGLY3827 targets the *Pichia pastoris* URA6 locus. Plasmid pGLY3827 is shown in FIG. 9. The DNA sequence of the AtECA1 was codon-optimized for expression in *Pichia pastoris* and is shown in SEQ ID NO:34. The encoded AtECA1 has the amino acid sequence set forth in SEQ ID NO:35.

Integration/expression plasmid pGLY3822 (contains expression cassette encoding PpPMR1) or pGLY3827 (contains expression cassette encoding AtECA1) was linearized with SpeI and transformed into *Pichia pastoris* strain yGLY3647 or yGLY3693 at the URA6 locus. The genomic integration of pGLY3822 or pGLY3827 at URA6 locus was confirmed by colony PCR (cPCR) using primers, 5'AOX1 (5'-GCGACTGGTTCCAATTGACAAGCTT-3' (SEQ ID NO:38) and PpPMR1/cLP (5'-GGTTGCTCTCGTC-GATACTCAAGTGGGAAG-3' (SEQ ID NO:39) for confirming PpPMR1 integration into the URA6 locus, and 5'AOX1 and AtECA1/cLP (5'-GTCGGCTGGAACCTTAT-CACCAACTCTCAG-3' (SEQ ID NO:40) for confirming integration of AtECA1 into the URA6 locus. The PCR conditions were one cycle of 95° C. for 2 minutes, 25 cycles of 95° C. for 10 seconds, 55° C. for 20 seconds, and 72° C. for one minute; followed by one cycle of 72° C. for 10 minutes.

Strain yGLY8238 was generated by transforming strain yGLY3647 with integration/expression plasmid pGLY3822 encoding the PpPMR1 and targeting the URA6 locus. In strain yGLY3647, the *Pichia pastoris* PDI1 chaperone gene has been replaced with the human PD1 gene as described in Example 1 and shown in FIGS. 1A and 1B.

Strain yGLY8240 was generated by transforming strain yGLY3647 with plasmid pGLY3827 encoding the AtECA1 and targeting the URA6 locus. The genealogy of the strains is shown in FIGS. 1A and 1B.

The strains were evaluated for the effect the addition of PpPMR1 or AtECA1 to the humanized chaperone strains might have on reducing O-glycosylation of the antibodies produced by the strains. As shown in Table 7 the addition of either PpPMR1 or AtECA1 into strain yGLY3647 effected a significant reduction in O-glycosylation occupancy compared to strain yGLY3647 expressing the human PDI in place of the *Pichia pastoris* PDI1 or strain yGLY2263 expressing only the endogenous PDI1 but capable of making antibodies with a $Man_5GlcNAc_2$ glycoform as strain yGLY3647. The results also suggest that yeast strains that express its endogenous PDI1 and not the human PDI1 and overexpress a $Ca^{2+}$ ATPase will produce glycoproteins with reduced O-glycan occupancy.

TABLE 7

| Strain | yGLY2263 (control) | yGLY3647 | yGLY3647 + $Ca^{2+}$ ATPase | |
| --- | --- | --- | --- | --- |
| | | | yGLY8240 AtECA1 | yGLY8238 PpPMR1 |
| O-glycan occupancy (H2 + L2: anti-DKK1) | 23.7 | 9.2 | 5.5 | 6.2 |

O-glycan occupancy was determined by Mannitol assay.

EXAMPLE 4

A DNA fragment encoding the human calreticulin (hCRT) without its native signal sequence was PCR amplified from a human liver cDNA library (BD Biosciences, San Jose, Calif.) using primers hCRT-BstZ17I-HA/UP: 5'-GTATACCCAT-ACGACGTCCCAGACTACGCTGAGCCCGC-CGTCTACTTCAAGGAGC-3' (SEQ ID NO:45) and hCRT-PacI/LP: 5'-TTAATTAACTACAGCTCGTCATGGGCCTGGCCG GGGACATCTTCC-3' (SEQ ID NO:46). The PCR conditions were one cycle of 98° C. for two min; 30 cycles of 98° C. for 10 seconds, 55° C. for 30 seconds, and 72° C. for two minutes, and followed by one cycle of 72° C. for 10 minutes. The resulting PCR product was cloned into pCR2.1 Topo vector to make pGLY1224. The DNA encoding the hCRT further included modifications such that the encoded truncated hCRT has an HA tag at its N-terminus and HDEL at its C-terminus The DNA encoding the hCRT was released from pGLY1224 by digestion with BstZ17I and PacI and the DNA fragment cloned into an expression vector pGLY579, which had been digested with NotI and PacI, along with a DNA fragment encoding the *S. cerevisiae* alpha-mating factor pre signal sequence having NotI and PacI compatible ends to create pGLY1230. This plasmid is an integration/expression plasmid that encodes the hCRT with the *S. cerevisiae* alpha-mating factor pre signal sequence and HA tag at the N-terminus and an HDEL sequence at its C-terminus operably linked to the *Pichia pastoris* GAPDH promoter and targeting the HIS3 locus of *Pichia pastoris*.

A DNA fragment encoding the human ERp57 (hERp57) was synthesized by GeneArt AG having NotI and PacI compatible ends. The DNA fragment was then cloned into pGLY129 digested with NotI and PacI to produce pGLY1231. This plasmid encodes the hERp57 operably linked to the *Pichia pastoris* PMA1 promoter.

Figure 10:
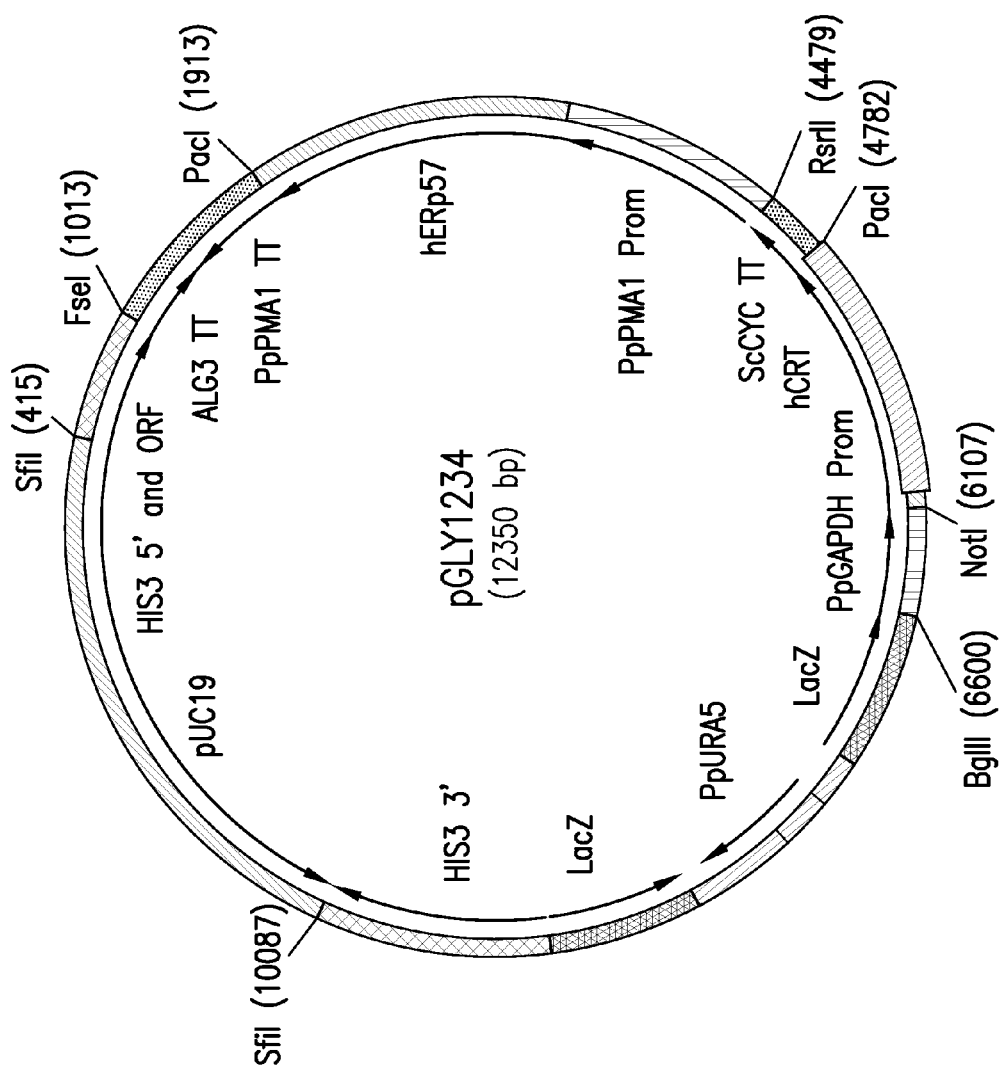
FIG. 10 is a map of plasmid vector pGLY1234 encoding the human CRT (hCRT) and human ERp57(hERp57) and targeting the *Pichia pastoris* HIS3 locus.

Plasmid pGLY1231 was digested with SwaI and the DNA fragment encoding the hERp57 was cloned into plasmid pGLY1230 digested with PmeI. Thus, integration/expression plasmid pGLY1234 encodes both the hCRT and hERp57. Plasmid pGLY1234 is shown in FIG. 10.

Strain yGLY3642 was generated by counterselecting strain yGLY2690 in the presence of 5'FOA, a URA5 auxotroph.

Strain yGLY3668 was generated by transforming yGLY3642 with integration/expression plasmid pGLY1234 encoding the hCRT and hERp57 and which targets the HIS3 locus.

Strain yGLY3693 was generated by transforming strain yGLY3668 with integration/expression plasmid pGLY2261, which targets an expression cassette encoding the anti-DKK1 antibody to the TRP2 locus.

Strain yGLY8239 was generated by transforming strain yGLY3693 with integration/expression plasmid pGLY3822 encoding the PpPMR1 and targeting the URA6 locus.

Strain yGLY8241 was generated by transforming strain yGLY3693 with integration/expression plasmid pGLY3827 encoding the AtECA1 and targeting the URA6 locus.

The genealogy of the strains described in this example are shown in FIGS. 1A and 1B.

The above strains were evaluated to see whether the addition of hCRT and hERp57 to the humanized chaperone strains expressing PpPMR1 or AtECA1 of the previous example might effect a further reduction in O-glycan occupancy of the antibodies produced. As shown in Table 8, in strain yGLY3693 expressing hCRT and hERp57 alone, there was about a 2-fold decrease in O-glycan occupancy, which was further decreased up to a 4-fold in strains that further expressed PpPMR1 or AtECA1. The results also suggest that yeast strains that express its endogenous PDI1 and overexpress a $Ca^{2+}$ ATPase will produce glycoproteins with reduced O-glycan occupancy.

TABLE 8

| Strain | yGLY2263 (control) | yGLY3693 | yGLY3693 + $Ca^{2+}$ ATPase | |
|---|---|---|---|---|
| | | | yGLY8241 AtECA1 | yGLY8239 PpPMR1 |
| O-glycan occupancy (H2 + L2: anti-DKK1) | 23.7 | 10.4 | 5.5 | 7.8 |

O-glycan occupancy was determined by Mannitol assay.

TABLE 9

| BRIEF DESCRIPTION OF THE SEQUENCES | | |
|---|---|---|
| SEQ ID NO: | Description | Sequence |
| 1 | PCR primer hPDI/UP1 | AGCGCTGACGCCCCCGAGGAGGAGGACCAC |
| 2 | PCR primer hPDI/LP-PacI | CCTTAATTAATTACAGTTCATCATGCACAGCTTTCTGATCAT |
| 3 | PCR primer PB248 | ATGAATTCAGGC CATATCGGCCATTGTTTACTGTGCG CCCACAGTAG |
| 4 | PCR primer PB249 | ATGTTTA AACGTGAGGATTACTGGTGATGAAAGAC |
| 5 | PCR primer PB250 | AGACTAGTCTATTTGGAG ACATTGACGGATCCAC |
| 6 | PCR primer PB251 | ATCTCGAGAGGCCATGCAGGCCAACCACAAGATGAATCAAAT TTTG |
| 7 | PCR primer PpPDI/UPi-1 | GGTGAGGTTGAGGTCCCAAGTGACTATCAAGGTC |
| 8 | PCR primer PpPDI/LPi-1 | GACCTTGATAGTCACTTGGGACCTCAACCTCACC |

TABLE 9 -continued

BRIEF DESCRIPTION OF THE SEQUENCES

| SEQ ID NO: | Description | Sequence |
|---|---|---|
| 9 | PCR primer PpPDI/UPi-2 | CGCCAATGATGAGGATGCCTCTTCAAAGGTTGTG |
| 10 | PCR primer PpPDI/LPi-2 | CACAACCTTTGAAGAGGCATCCTCATCATTGGCG |
| 11 | PCR primer PpPDI-5'/UP | GGCGATTGCATTCGCGAC TGTATC |
| 12 | PCR primer hPDI-3'/LP | CCTAGAGAGCGGTGG CCAAGATG |
| 13 | PCR primer hPDI/UP | GTGGCCACACCAGGGGGC ATGGAAC |
| 14 | PCR primer hPDI-3'/LP | CCTAGAGAGCGGTGG CCAAGATG |
| 15 | PCR primer hGRP94/UP1 | AGCGCTGACGATGAAGTTGATGTGGATGGTACA GTAG |
| 16 | PCR primer hGRP94/LP1 | GGCCGGCCTTACAATTCATCATG TTCAGCTGTAGATTC |
| 17 | Saccharomyces cerevisiae mating factor pre-signal peptide (DNA) | ATG AGA TTC CCA TCC ATC TTC ACT GCT GTT TTG TTC GCT GCT TCT TCT GCT TTG GCT |
| 18 | Saccharomyces cerevisiae mating factor pre-signal peptide (protein) | MRFPSIFTAVLFAASSALA |
| 19 | human PDI Gene (DNA) | GACGCCCCCGAGGAGGAGGACCACGTCTTGGTGCTGCGGAAA AGCAACTTCGCGGAGGCGCTGGCGGCCCACAAGTACCCGCCG GTGGAGTTCCATGCCCCCTGGTGTGGCCACTGCAAGGCTCTG CCCCTGAGTATGCCAAAGCCGCTGGGAAGCTGAAGGCAGAAG GTTCCGAGATCAGGTTGGCCAAGGTGGACGCCACGGAGGAGT CTGACCTAGCCCAGCAGTACGGCGTGCGCGGCTATCCCACCAT CAAGTTCTTCAGGAATGGAGACACGGCTTCCCCCAAGGAATA TACAGCTGGCAGAGAGGCTGATGACATCGTGAACTGGCTGAA GAAGCGCACGGGCCCGGCTGCCACCACCCTGCCTGACGGCGC AGCTGCAGAGTCCTTGGTGGAGTCCAGCGAGGTGGCCGTCAT CGGCTTCTTCAAGGACGTGGAGTCGGACTCTGCCAAGCAGTTT TTGCAGGCAGCAGAGGCCATCGATGACATACCATTTGGGATC ACTTCCAACAGTGACGTGTTCTCCAAATACCAGCTCGACAAAG ATGGGGTTGTCCTCTTTAAGAAGTTTGATGAAGGCCGGAACA ACTTTGAAGGGGAGGTCACCAAGGAGAACCTGCTGGACTTTA TCAAACACAACCAGCTGCCCCTTGTCATCGAGTTCACCGAGCA GACAGCCCCGAAGATTTTTGGAGGTGAAATCAAGACTCACAT CCTGCTGTTCTTGCCCAAGAGTGTGTCTGACTATGACGGCAAA CTGAGCAACTTCAAAACAGCAGCCGAGAGCTTCAAGGGCAAG ATCCTGTTCATCTTCATCGACAGCGACCACACCGACAACCAGC GCATCCTCGAGTTCTTTGGCCTGAAGAAGGAAGAGTGCCCGG CCGTGCGCCTCATCACCTTGGAGGAGGAGATGACCAAGTACA AGCCCGAATCGGAGGAGCTGACGGCAGAGAGGATCACAGAG TTCTGCCACCGCTTCCTGGAGGGCAAAATCAAGCCCCACCTGA TGAGCCAGGAGCTGCCGGAGGACTGGGACAAGCAGCCTGTCA AGGTGCTTGTTGGGAAGAACTTTGAAGACGTGGCTTTTGATGA GAAAAAAAACGTCTTTGTGGAGTTCTATGCCCCATGGTGTGGT CACTGCAAACAGTTGGCTCCCATTTGGGATAAACTGGGAGAG ACGTACAAGGACCATGAGAACATCGTCATCGCCAAGATGGAC TCGACTGCCAACGAGGTGGAGGCCGTCAAAGTGCACGCCTTC CCCACACTCGGGTTCTTTCCTGCCAGTGCCGACAGGACGGTCA TTGATTACAACGGGAACGCACGCTGGATGGTTTTAAGAAAT TCCTAGAGAGCGGTGGCCAAGATGGGCAGGGGATGTTGACG ACCTCGAGGACCTCGAAGAAGCAGAGGAGCCAGACATGGAG GAAGACGATGACCAGAAAGCTGTGAAAGATGAACTGTAA |
| 20 | human PDI | DAPEEEDHVLVLRKSNFAEALAAHKYPPVEFHAPWCGHCKALA |

TABLE 9 -continued

BRIEF DESCRIPTION OF THE SEQUENCES

| SEQ ID NO: | Description | Sequence |
|---|---|---|
| | Gene (protein) | PEYAKAAGKLKAEGSEIRLAKVDATEESDLAQQYGVRGYPTIKF FRNGDTASPKEYTAGREADDIVNWLKKRTGPAATTLPDGAAAES LVESSEVAVIGFFKDVESDSAKQFLQAAEAIDDIPFGITSNSDVFS KYQLDKDGVVLFKKFDEGRNNFEGEVTKENLLDFIKHNQLPLVI EFTEQTAPKIFGGEIKTHILLFLPKSVSDYDGKLSNFKTAAESFKG KILFIFIDSDHTDNQRILEFFGLKKEECPAVRLITLEEEMTKYKPES EELTAERITEFCHRFLEGKIKPHLMSQELPEDWDKQPVKVLVGK NFEDVAFDEKKNVFVEFYAPWCGHCKQLAPIWDKLGETYKDHE NIVIAKMDSTANEVEAVKVHGFPTLGFFPASADRTVIDYNGERTL DGFKKFLESGGQDGAGDVDDLEDLEEAEEPDMEEDDDQKAVHD EL |
| 21 | Pichia pastoris PDI1 Gene (DNA) | ATGCAATTCAACTGGAATATTAAAACTGTGGCAAGTATTTTGT CCGCTCTCACACTAGCACAAGCAAGTGATCAGGAGGCTATTG CTCCAGAGGACTCTCATGTCGTCAAATTGACTGAAGCCACTTT TGAGTCTTTCATCACCAGTAATCCTCACGTTTTGGCAGAGTTTT TTGCCCCTTGGTGTGGTCACTGTAAGAAGTTGGGCCCTGAACT TGTTTCTGCTGCCGAGATCTTAAAGGACAATGAGCAGGTTAAG ATTGCTCAAATTGATTGTACGGAGGAGAAGGAATTATGTCAA GGCTACGAAATTAAAGGGTATCCTACTTTGAAGGTGTTCCATG GTGAGGTTGAGGTCCCAAGTGACTATCAAGGTCAAAGACAGA GCCAAAGCATTGTCAGCTATATGCTAAAGCAGAGTTTACCCCC TGTCAGTGAAATCAATGCAACCAAAGATTTAGACGACACAAT CGCCGAGGCAAAAGAGCCCGTGATTGTGCAAGTACTACCGGA AGATGCATCCAACTTGGAATCTAACACCACATTTTACGGAGTT GCCGGTACTCTCAGAGAGAAATTCACTTTTGTCTCCACTAAGT CTACTGATTATGCCAAAAAATACACTAGCGACTCGACTCCTGC CTATTTGCTTGTCAGACCTGGCGAGGAACCTAGTGTTTACTCT GGTGAGGAGTTAGATGAGACTCATTTGGTGCACTGGATTGAT ATTGAGTCCAAACCTCTATTTGGAGACATTGACGGATCCACCT TCAAATCATATGCTGAAGCTAACATCCCTTTAGCCTACTATTT CTATGAGAACGAAGAACAACGTGCTGCTGCTGCCGATATTATT AAACCTTTTGCTAAAGAGCAACGTGGCAAAATTAACTTTGTTG GCTTAGATGCCGTTAAATTCGGTAAGCATGCCAAGAACTTAA ACATGGATGAAGAGAAACTCCCTCTATTTGTCATTCATGATTT GGTGAGCAACAAGAAGTTTGGAGTTCCTCAAGACCAAGAATT GACGAACAAAGATGTGACCGAGCTGATTGAGAAATTCATCGC AGGAGAGGCAGAACCAATTGTGAAATCAGAGCCAATTCCAGA AATTCAAGAAGAGAAAGTCTTCAAGCTAGTCGGAAAGGCCCA CGATGAAGTTGTCTTCGATGAATCTAAAGATGTTCTAGTCAAG TACTACGCCCCTTGGTGTGGTCACTGTAAGAGAATGGCTCCTG CTTATGAGGAATTGGCTACTCTTTACGCCAATGATGAGGATGC CTCCTTCAAAGGTTGTGATTGCAAAACTTGATCACACTTTGAAC GATGTCGACAACGTTGATATTCAAGGTTATCCTACTTTGATCC TTTATCCAGCTGGTGATAAATCCAATCCTCAACTGTATGATGG ATCCGTGACCTAGAATCATTGGCTGAGTTTGTAAAGGAGAG AGGAACCCACAAAGTGGATGCCCTAGCACTCAGACCAGTCGA GGAAGAAAAGGAAGCTGAAGAAGAAGCTGAAAGTGAGGCAG ACGCTCACGACGAGCTTTAA |
| 22 | Pichia pastoris PDI1 Gene (protein) | MQFNWNIKTVASILSALTLAQASDQEAIAPEDSHVVKLTEATFES FITSNPHVLAEFFAPWCGHCKKLGPELVSAAEILKDNEQVKIAQI DCTEEKELCQGYEIKGYPTLKVFHGEVEVPSDYQGQRQSQSIVSY MLKQSLPPVSEINATKDLDDTIAEAKEPVIVQVLPEDASNLESNT TFYGVAGTLREKFTFVSTKSTDYAKKYTSDSTPAYLLVRPGEEPS VYSGEELDETHLVHWIDIESKPLFGDIDGSTFKSYAEANIPLAYYF YENEEQRAAAADIIKPFAKEQRGKINFVGLDAVKFGKHAKNLM DEEKLPLFVIHDLVSNKKFGVPQDQELTNKDVTELIEKFIAGEAEP IVKSEPIPEIQEEKVFKLVGKAHDEVVFDESKDVLVKYYAPWCG HCKRMAPAYEELATLYANDEDASSKVVIAKLDHTLNDVDNVDI QGYPTLILYPAGDKSNPQLYDGSRDLESLAEFVKERGTHKVDAL ALRPVEEEKEAEEEAESEADAHDEL |
| 23 | human ERO1α Gene (DNA) | GAAGAACAACCACCAGAGACTGCTGCTCAGAGATGCTTCTGT CAGGTTTCCGGTTACTTGGACGACTGTACTTGTGACGTTGAGA CTATCGACAGATTCAACAACTACAGATTGTTCCCAAGATTGCA GAAGTTGTTGGAGTCCGACTACTTCAGATACTACAAGGTTAAC TTGAAGAGACCATGTCCATTCTGGAACGACATTTCCCAGTGTG GTAGAAGAGACTGTGCTGTTAAGCCATGTCAATCCGACGAAG TTCCAGACGGTATTAAGTCCGCTTCCTACAAGTACTCTGAAGA GGCTAACAACTTGATCGAAGAGTGTGAGCAAGCTGAAAGATT GGGTGCTGTTGACGAATCTTTGTCCGAGAGACTCAGAAGGCT GTTTTGCAGTGGACTAAGCACGATGATTCCTCCGACAACTTCT GTGAAGCTGACGACATTCAATCTCCAGAGGCTGAGTACGTTG |

TABLE 9 -continued

BRIEF DESCRIPTION OF THE SEQUENCES

| SEQ ID NO: | Description | Sequence |
|---|---|---|
| | | ACTTGTTGTTGAACCCAGAGAGATACACTGGTTACAAGGGTCC<br>AGACGCTTGGAAGATTTGGAACGTTATCTACGAAGAGAACTG<br>TTTCAAGCCACAGACTATCAAGAGACCATTGAACCCATTGGCT<br>TCCGGACAGGGAACTTCTGAAGAGAACACTTTCTACTCTTGGT<br>TGGAGGGTTTGTGTGTTGAGAAGAGAGCTTTCTACAGATTGAT<br>CTCCGGATTGCACGCTTCTATCAACGTTCACTTGTCCGCTAGA<br>TACTTGTTGCAAGAGACTTGGTTGGAAAAGAAGTGGGGTCAC<br>AACATTACTGAGTTCCAGCAGAGATTCGACGGTATTTTGACTG<br>AAGGTGAAGGTCCAAGAAGATTGAAGAACTTGTACTTTTTGT<br>ACTTGATCGAGTTGAGAGCTTTGTCCAAGGTTTTGCCATTCTT<br>CGAGAGACCAGACTTCCAATTGTTCACTGGTAACAAGATCCA<br>GGACGAAGAGAACAAGATGTTGTTGTTGGAGATTTTGCACGA<br>GATCAAGTCCTTTCCATTGCACTTCGACGAGAACTCATTTTTC<br>GCTGGTGACAAGAAAGAAGCTCACAAGTTGAAAGAGGACTTC<br>AGATTGCACTTCAGAAATATCTCCAGAATCATGGACTGTGTTG<br>GTTGTTTCAAGTGTAGATTGTGGGGTAAGTTGCAGACTCAAGG<br>ATTGGGTACTGCTTTGAAGATTTTGTTCTCCGAGAAGTTGATC<br>GCTAACATGCCTGAATCTGGTCCATCTTACGAGTTCCACTTGA<br>CTAGACAAGAGATCGTTTCCTTGTTCAACGCTTTCGGTAGAAT<br>CTCCACTTCCGTTAAAGAGTTGGAGAACTTCAGAAACTTGTTG<br>CAGAACATCCACTAA |
| 24 | human ERO1α Gene (protein) | EEQPPETAAQRCFCQVSGYLDDCTCDVETIDRFNNYRLFPRLQKL<br>LESDYFRYYKVNLKRPCPFWNDISQCGRRDCAVKPCQSDEVPDG<br>IKSASYKYSEEANNLIEECEQAERLGAVDESLSEETQKAVLQWTK<br>HDDSSDNFCEADDIQSPEAEYVDLLLNPERYTGYKGPDAWKIWN<br>VIYEENCFKPQTIKRPLNPLASGQGTSEENTFYSWLEGLCVEKRA<br>FYRLISGLHASINVHLSARYLLQETWLEKKWGHNITEFQQRFDGI<br>LTEGEGPRRLKNLYFLYLIELRALSKVLPFFERPDFQLFTGNKIQD<br>EENKMLLLEILHEIKSPPLHFDENSFFAGDKKEAHKLKEDFRLHF<br>RNISRIMDCVGCFKCRLWGKLQTQGLGTALKILFSEKLIANMPES<br>GPSYEFHLTRQEIVSLFNAFGRISTSVKELENFRNLLQNIH |
| 25 | human GRP94 Gene (DNA) | GATGATGAAGTTGACGTTGACGGTACTGTTGAAGAGGACTTG<br>GGAAAGTCTAGAGAGGGTTCCAGAACTGACGACGAAGTTGTT<br>CAGAGAGAGGAAGAGGCTATTCAGTTGGACGGATTGAACGCT<br>TCCCAAATCAGAGAGTTGAGAGAGAAGTCCGAGAAGTTCGCT<br>TTCCAAGCTGAGGTTAACAGAATGATGAAATTGATTATCAACT<br>CCTTGTACAAGAACAAAGAGATTTTCTTGAGAGAGTTGATCTC<br>TAACGCTTCTGACGCTTTGGACAAGATCAGATTGATCTCCTTG<br>ACTGACGAAAACGCTTTGTCCGGTAACGAAGAGTTGACTGTT<br>AAGATCAAGTGTGACAAAGAGAAGAACTTGTTGCACGTTACT<br>GACACTGGTGTTGGAATGACTAGAGAAGAGTTGGTTAAGAAC<br>TTGGGTACTATCGCTAAGTCTGGTACTTCCGAGTTCTTGAACA<br>AGATGACTGAGGCTCAAGAAGATGGTCAATCCACTTCCGAGT<br>TGATTGGTCAGTTCGGTGTTGGTTTCTACTCCGCTTTCTTGGTT<br>GCTGACAAGGTTATCGTTACTTCCAAGCACAACAACGACACTC<br>AACACATTTGGGAATCCGATTCCAACGAGTTCTCCGTTATTGC<br>TGACCCAAGAGGTAACACTTTGGGTAGAGGTACTACTATCACT<br>TTGGTTTTGAAAGAAGAGGCTTCCGACTACTTGGAGTTGGACA<br>CTATCAAGAACTTGGTTAAGAAGTACTCCCAGTTCATCAACTT<br>CCCAATCTATGTTTGGTCCTCCAAGACTGAGAC<br>TGTTGAGGAACCAATGGAAGAAGAAGAGGCTGCTAAAGAAG<br>AGAAAGAGGAATCTGACGACGAGGCTGCTGTTGAAGAAGAG<br>GAAGAAGAAAAGAAGCCAAAGACTAAGAAGGTTGAAAAGAC<br>TGTTTGGGACTGGGAGCTTATGAACGACATCAAGCCAATTTGG<br>CAGAGACCATCCAAAGAGGTTGAGGAGGACGAGTACAAGGCT<br>TTCTACAAGTCCTTCTCCAAAGAATCCGATGACCCAATGGCTT<br>ACATCCACTTCACTGCTGAGGGTGAAGTTACTTTCAAGTCCAT<br>CTTGTTCGTTCCAACTTCTGCTCCAAGAGGATTGTTCGACGAG<br>TACGGTTCTAAGAAGTCCGACTACATCAAACTTTATGTTAGAA<br>GAGTTTTCATCACTGACGACTTCCACGATATGATGCCAAAGTA<br>CTTGAACTTCGTTAAGGGTGTTGTTGATTCCGATGACTTGCCA<br>TTGAACGTTTCCAGAGAGACTTTGCAGCAGCACAAGTTGTTGA<br>AGGTTATCAGAAAGAAACTTGTTAGAAAGACTTTGGACATGA<br>TCAAGAAGATCGCTGACGACAAGTACAACGACACTTTCTGGA<br>AAGAGTTCGGAACTAACATCAAGTTGGGTGTTATTGAGGACC<br>ACTCCAACAGAACTAGATTGGCTAAGTTGTTGAGATTCCAGTC<br>CTCTCATCACCCAACTGACATCACTTCCTTGGACCAGTACGTT<br>GAGAGAATGAAAGAGAAGCAGGACAAAATCTACTTCATGGCT<br>GGTTCCTCTAGAAAAGAGGCTGAATCCTCCCCATTCGTTGAGA<br>GATTGTTGAAGAAGGGTTACGAGGTTATCTACTTGACTGAGCC<br>AGTTGACGAGTACTGTATCCAGGCTTTGCCAGAGTTTGACGGA<br>AAGAGATTCCAGAACGTTGCTAAAGAGGGTGTTAAGTTCGAC |

TABLE 9 -continued

BRIEF DESCRIPTION OF THE SEQUENCES

| SEQ ID NO: | Description | Sequence |
|---|---|---|
| | | GAATCCGAAAAGACTAAAGAATCCAGAGAGGCTGTTGAGAAA |
| | | GAGTTCGAGCCATTGTTGAACTGGATGAAGGACAAGGCTTTG |
| | | AAGGACAAGATCGAGAAGGCTGTTGTTTCCCAGAGATTGACT |
| | | GAATCCCCATGTGCTTTGGTTGCTTCCCAATACGGATGGAGTG |
| | | GTAACATGGAAAGAATCATGAAGGCTCAGGCTTACCAAACTG |
| | | GAAAGGACATCTCCACTAACTACTACGCTTCCCAGAAGAAAA |
| | | CTTTCGAGATCAACCCAAGACACCCATTGATCAGAGACATGTT |
| | | GAGAAGAATCAAAGAGGACGAGGACGACAAGACTGTTTTGG |
| | | ATTTGGCTGTTGTTTTGTTCGAGACTGCTACTTTGAGATCCGGT |
| | | TACTTGTTGCCAGACACTAAGGCTTACGGTGACAGAATCGAG |
| | | AGAATGTTGAGATTGTCCTTGAACATTGACCCAGACGCTAAG |
| | | GTTGAAGAAGAACCAGAAGAAGAGCCAGAGGAAACTGCTGA |
| | | AGATACTACTGAGGACACTGAACAAGACGAGGACGAAGAGA |
| | | TGGATGTTGGTACTGACGAAGAGGAAGAGACAGCAAAGGAAT |
| | | CCACTGCTGAACACGACGAGTTGTAA |
| 26 | human GRP94 Gene (protein) | DDEVDVDGTVEEDLGKSREGSRTDDEVVQREEEAIQLDGLNASQ IRELREKSEKFAFQAEVNRMMKLIINSLYKNKEIFLRELISNASDA LDKIRLISLTDENALSGNEELTVKIKCDKEKNLLHVTDTGVGMTR EELVKNLGTIAKSGTSEFLNKMTEAQEDGQSTSELIGQFGVGFYS AFLVADKVIVTSKHNNDTQHIWESDSNEFSVIADPRGNTLGRGTT ITLVLKEEASDYLELDTIKNLVKKYSQFINFPIYVWSSKTETVEEP MEEEEAAKEEKEESDDEAAVEEEEEEKKPKTKKVEKTVWDWEL MNDIKPIWQRPSKEVEEDEYKAFYKSFSKESDDPMAYIHFTAEGE VTFKSILFVPTSAPRGLFDEYGSKKSDYIKLYVRRVFITDDPHDM MPKYLNFVKGVVDSDDLPLNVSRETLQQHKLLKVIRKKLVRKTL DMIKKIADDKYNDTFWKEFGTNIKLGVIEDHSNRTRLAKLLRFQS SHHPTDITSLDQYVERMKEKQDKIYFMAGSSRKEAESSPFVERLL KKGYEVIYLTEPVDEYCIQALPEFDGKRFQNVAKEGVKFDESEK TKESREAVEKEFEPLLNWMKDKALKDKIEKAVVSQRLTESPCAL VASQYGWSGNMERIMKAQAYQTGKDISTNYYASQKKTFEINPR HPLIRDMLRRIKEDEDDKTVLDLAVVLFETATLRSGYLLPDTKAY GDRIERMLRLSLNIDPDAKVEEEPEEEPEETAEDTTEDTEQDEDE EMDVGTDEEEETAKESTAEHDEL |
| 27 | anti-DKK1 Heavy chain (VH + IgG2m4) (α-amylase encoding sequences underlined) (DNA) | <u>ACGATGGTCGCTTGGTGGTCTTTGTTTCTGTACGGTCTTCAGGT</u> <u>CGCTGCACCT</u>GCTTTGGCTGAGGTTCAGTTGGTTCAATCTGGT GCTGAGGTTAAGAAACCTGGTGCTTCCGTTAAGGTTTCCTGTA AGGCTTCCGGTTACACTTTCACTGACTACTACATCCACTGGGT TAGACAAGCTCCAGGTCAAGGATTGGAATGGATGGGATGGAT TCACTCTAACTCCGGTGCTACTACTTACGCTCAGAAGTTCCAG GCTAGAGTTACTATGTCCAGAGACACTTCTTCTTCCACTGCTT ACATGGAATTGTCCAGATTGGAATCCGATGACACTGCTATGTA CTTTTGTTCCAGAGAGGACTACTGGGGACAGGGAACTTTGGTT ACTGTTTCCTCCGCTTCTACTAAAGGGCCCTCTGTTTTTCCATT GGCTCCATGTTCTAGATCCACTTCCGAATCCACTGCTGCTTTG GGATGTTTGGTTAAGGACTACTTCCCAGAGCCAGTTACTGTTT CTTGGAACTCCGGTGCTTTGACTTCTGGTGTTCACACTTTCCCA GCTGTTTTGCAATCTTCCGGTTTGTACTCCTTGTCCTCCGTTGT TACTGTTACTTCCTCCAACTTCGGTACTCAGACTTACACTTGTA ACGTTGACCACAAGCCATCCAACACTAAGGTTGACAAGACTG TTGAGAGAAAGTGTTGTGTTGAGTGTCCACCATGTCCAGCTCC ACCAGTTGCTGGTCCATCCGTTTTTTTGTTCCCACCAAAGCCA AAGGACACTTTGATGATCTCCAGAACTCCAGAGGTTACATGTG TTGTTGTTGACGTTTCCAAGAGGACCCAGAGGTTCAATTCAA CTGGTACGTTGACGGTGTTGAAGTTCACAACGCTAAGACTAA GCCAAGAGAAGAGCAGTTCAACTCCACTTTCAGAGTTGTTTCC GTTTTGACTGTTTTGCACCAGGATTGGTTGAACGGTAAAGAAT ACAAGTGTAAGGTTTCCAACAAGGGATTGCCATCCTCCATCGA AAAGACTATCTCCAAGACTAAGGGACAACCAAGAGAGCCACA GGTTTACACTTTGCCACCATCCAGAGAAGAGATGACTAAGAA CCAGGTTTCCTTGACTTGTTTGGTTAAAGGATTCTACCCATCC GACATTGCTGTTGAGTGGGAATCTAACGGTCAACCAGAGAAC AACTACAAGACTACTCCACCAATGTTGGATTCTGACGGTTCCT TCTTCTTGTACTCCAAGTTGACTGTTGACAAGTCCAGATGGCA ACAGGGTAACGTTTTCTCCTGTTCCGTTATGCATGAGGCTTTG CACAACCACTACACTCAAAAGTCCTTGTCTTTGTCCCCTGGTA AGTAA |
| 28 | anti-DKK 1 Heavy chain (VH + IgG2m4) (protein) | EVQLVQSGAEVKKPGASVKVSCKASGYTFTDYYIHWVRQAPGQ GLEWMGWIHSNSGATTYAQKFQARVTMSRDTSSSTAYMELSRL ESDDTAMYFCSREDYWGQGTLVTVSSASTKGPSVFPLAPCSRST SESTAALGCLVKDYFPEPVTVSWNSGALTSGVHTFPAVLQSSGL YSLSSVVTVTSSNFGTQTYTCNVDHKPSNTKVDKTVERKCCVEC |

TABLE 9 -continued

BRIEF DESCRIPTION OF THE SEQUENCES

| SEQ ID NO: | Description | Sequence |
|---|---|---|
| | | PPCPAPPVAGPSVFLFPPKPKDTLMISRTPEVTCVVVDVSQEDPEV QFNWYVDGVEVHNAKTKPREEQFNSTFRVVSVLTVLHQDWLN GKEYKCKVSNKGLPSSIEKTISKTKGQPREPQVYTLPPSREEMTK NQVSLTCLVKGFYPSDIAVEWESNGQPENNYKTTPPMLDSDGSF FLYSKLTVDKSRWQQGNVFSCSVMHEALHNHYTQKSLSLSPGK |
| 29 | anti-DKK 1 Light chain (VL + lambda constant regions) (α-amylase encoding sequences underlined) (DNA) | <u>ACGATGGTCGCTTGGTGGTCTTTGTTTCTGTACGGTCTTCAGGT CGCTGCACCTGCTTTGGCT</u>CAGTCCGTTTTGACACAACCACCA TCTGTTTCTGGTGCTCCAGGACAGAGAGTTACTATCTCCTGTA CTGGTTCCTCTTCCAACATTGGTGCTGGTTACGATGTTCACTG GTATCAACAGTTGCCAGGTACTGCTCCAAAGTTGTTGATCTAC GGTTACTCCAACAGACCATCTGGTGTTCCAGACAGATTCTCTG GTTCTAAGTCTGGTGCTTCTGCTTCCTTGGCTATCACTGGATTG AGACCAGATGACGAGGCTGACTACTACTGTCAATCCTACGAC AACTCCTTGTCCTCTTACGTTTTCGGTGGTGGTACTCAGTTGAC TGTTTTGTCCCAGCCAAAGGCTAATCCAACTGTTACTTTGTTCC CACCATCTTCCGAAGAACTGCAGGCTAATAAGGCTACTTTGGT TTGTTTGATCTCCGACTTCTACCCAGGTGCTGTTACTGTTGCTT GGAAGGCTGATGGTTCTCCAGTTAAGGCTGGTGTTGAGACTAC TAAGCCATCCAAGCAGTCCAATAACAAGTACGCTGCTAGCTCT TACTTGTCCTTGACACCAGAACAATGGAAGTCCCACAGATCCT ACTCTTGTCAGGTTACACACGAGGGTTCTACTGTTGAAAAGAC TGTTGCTCCAACTGAGTGTTCCTAA |
| 30 | anti-DKK1 Light chain (VL + lambda constant regions) (protein) | QSVLTQPPSVSGAPGQRVTISCTGSSSNIGAGYDVHWYQQLPGTA PKLLIYGYSNRPSGVPDRFSGSKSGASASLAITGLRPDDEADYYC QSYDNSLSSYVFGGGTQLTVLSQPKANPTVTLFPPSSEELQANKA TLVCLISDFYPGAVTVAWKADGSPVKAGVETTKPSKQSNNKYA ASSYLSLTPEQWKSHRSYSCQVTHEGSTVEKTVAPTECS |
| 31 | PpPDI1 promoter | AACACGAACACTGTAAATAGAATAAAAGAAAACTTGGATAGT AGAACTTCAATGTAGTGTTTCTATTGTCTTACGCGGCT CTTTAGATTGCAATCCCCAGAATGGAATCGTCCATCTTTCTCA ACCCACTCAAAGATAATCTACCAGACATACCTACGCC CTCCATCCCAGCACCACGTCGCGATCACCCCTAAAACTTCAAT AATTGAACACGTACTGATTTCCAAACCTTCTTCTTCT TCCTATCTATAAGA |
| 32 | PpPMR1 | ATGACAGCTAATGAAAATCCTTTTGAGAATGAGCTGACAGGA TCTTCTGAATCTGCCCCCCCTGCATTGGAATCGAAGACTGGAG AGTCTCTTAAGTATTGCAAATATACCGTGGATCAGGTCATAGA AGAGTTTCAAACGGATGGTCTCAAAGGATTGTGCAATTCCCA GGACATCGTATATCGGAGGTCTGTTCATGGGCAAATGAAAT GGAAGTCGAAGAGGAAGAGAGTCTTTTTTCGAAATTCTTGTCA AGTTTCTACAGCGATCCATTGATTCTGTTACTGATGGGTTCCG CTGTGATTAGCTTTTTGATGTCTAACATTGATGATGCGATATCT ATCACTATGGCAATTACGATCGTTGTCACAGTTGGATTTGTTC AAGAGTATCGATCCGAGAAATCATTGGAGGCATTGAACAAGT TAGTCCCTGCCGAAGCTCATCTAACTAGGAATGGGAACACTG AAACTGTTCTTGCTGCCAACCTAGTCCCAGGAGACTTGGTGGA TTTTTCGGTTGGTGACAGAATTCCGGCTGATGTGAGAATTATT CACGCTTCCCACTTGAGTATCGACGAGAGCAACCTAACTGGTG AAAATGAACCAGTTTCTAAAGACAGCAAACCTGTTGAAAGTG ATGACCCAAACATTCCCTTGAACAGCCGTTCATGTATTGGGTA TATGGGCACTTTAGTTCGTGATGGTAATGGCAAAGGTATTGTC ATCGGAACAGCCAAAAACACAGCTTTTGGCTCTGTTTTCGAAA TGATGAGCTCTATTGAGAAACCAAAGACTCCTCTTCAACAGGC TATGGATAAACTTGGTAAGGATTTGTCTGCTTTTTCCTTCGGA ATCATCGGCCTTATTTGCTTGGTTGGTGTTTTTCAAGGTAGACC CTGGTTGGAAATGTTCCAGATCTCTGTATCCTTGGCTGTTGCT GCGATTCCAGAAGGTCTTCCTATTATTGTGACTGTGACTCTTG CTCTTGGTGTGTTGCGTATGGCTAAACAGAGGGCCATCGTCAA AAGACTGCCTAGTGTTGAAACTTTGGGATCCGTCAATGTTATC TGTAGTGATAAGACGGGAACATTGACCCAAAATCATATGACC GTTAACAGATTATGGACTGTGGATATGGGCGATGAATTCTTGA AAATTGAACAAGGGGAGTCCTATGCCAATTATCTCAAACCCG ATACGCTAAAAGTTCTGCAAACTGGTAATATAGTCAACAATG CCAAATATTCAAATGAAAAGGAAAAATACCTCGGAACCCGA CTGATATTGCAATTATTGAATCTTTAGAAAAATTTGATTTGCA GGACATTAGAGCAACAAAGGAAAGAATGTTGGAGATTCCATT TTCTTCGTCCAAGAAATATCAGGCCGTCAGTGTTCACTCTGGA GACAAAAGCAAATCTGAATTTTTGTTAAAGGCGCTCTGAAC AAAGTTTTGGAAAGATGTTCAAGATATTACAATGCTGAAGGT |

TABLE 9 -continued

BRIEF DESCRIPTION OF THE SEQUENCES

| SEQ ID NO: | Description | Sequence |
|---|---|---|
| | | ATCGCCACTCCACTCACAGATGAAATTAGAAGAAAATCCTTG<br>CAAATGGCCGATACGTTAGCATCTTCAGGATTGAGAATACTGT<br>CGTTTGCTTACGACAAAGGCAATTTTGAAGAAACTGGCGATG<br>GACCATCGGATATGATCTTTTGTGGTCTTTTAGGTATGAACGA<br>TCCTCCTAGACCATCTGTAAGTAAATCAATTTTGAAATTCATG<br>AGAGGTGGGGTTCACATTATTATGATTACAGGAGATTCAGAA<br>TCCACGGCCGTAGCCGTTGCCAAACAGGTCGGAATGGTAATT<br>GACAATTCAAAATATGCTGTCCTCAGTGGAGACGATATAGAT<br>GCTATGAGTACAGAGCAACTGTCTCAGGCGATCTCACATTGTT<br>CTGTATTTGCCCGGACTACTCCAAAACATAAGGTGTCCATTGT<br>AAGAGCACTACAGGCCAGAGGAGATATTGTTGCAATGACTGG<br>TGACGGTGTCAATGATGCCCCAGCTCTAAAACTGGCCGACATC<br>GGAATTGCCATGGGTAATATGGGGACCGATGTTGCCAAAGAG<br>GCAGCCGACATGGTTTTGACTGATGATGACTTTTCTACAATCT<br>TATCTGCAATCCAGGAGGGTAAAGGTATTTTCTACAACATCCA<br>GAACTTTTTAACGTTCCAACTTTCTACTTCAATTGCTGCTCTTT<br>CGTTAATTGCTCTGAGTACTGCTTTCAACCTGCCAAATCCATT<br>GAATGCCATGCAGATTTTGTGGATCAATATTATCATGGATGGA<br>CCTCCAGCTCAGTCTTTGGGTGTTGAGCCAGTTGATAAAGCTG<br>TGATGAACAAACCACCAAGAAAGCGAAATGATAAAATTCTGA<br>CAGGTAAGGTGATTCAAAGGGTAGTACAAAGTAGTTTTATCA<br>TTGTTTGTGGTACTCTGTACGTATACATGCATGAGATCAAAGA<br>TAATGAGGTCACAGCAAGAGACACTACGATGACCTTTACATG<br>CTTTGTATTCTTTGACATGTTCAACGCATTAACGACAAGACAC<br>CATTCTAAAAGTATTGCAGAACTTGGATGGAATAATACTATGT<br>TCAACTTTTCCGTTGCAGCTTCTATTTTGGGTCAACTAGGAGCT<br>ATTTACATTCCATTTTTGCAGTCTATTTTCCAGACTGAACCTCT<br>GAGCCTCAAAGATTTGGTCCATTTATTGTTGTTATCGAGTTCA<br>GTATGGATTGTAGACGAGCTTCGAAAACTCTACGTCAGGAGA<br>CGTGACGCATCCCCATACAATGGATACAGCATGGCTGTTTGA |
| 33 | PpPMR1 | MTANENPFENELTGSSESAPPALESKTGESLKYCKYTVDQVIEEF<br>QTDGLKGLCNSQDIVYRRSVHGPNEMEVEEEESLFSKFLSSFYSD<br>PLILLLMGSAVISFLMSNIDDAISITMAITIVVTVGFVQEYRSEKSL<br>EALNKLVPAEAHLTRNGNTETVLAANLVPGDLVDFSVGDRIPAD<br>VRIIHASHLSIDESNLTGENEPVSKDSKPVESDDPNIPLNSRSCIGY<br>MGTLVRDGNGKGIVIGTAKNTAFGSVFEMMSSIEKPKTPLQQAM<br>DKLGKDLSAFSFGIIGLICLVGVFQGRPWLEMFQISVSLAVAAIPE<br>GLPIIVTVTLALGVLRMAKQRAIVKRLPSVETLGSVNVICSDKTG<br>TLTQNHMTVNRLWTVDMGDEFLKIEQGESYANYLKPDTLKVLQ<br>TGNIVNNAKYSNEKEKYLGNPTDIAIIESLEKFDLQDIRATKERML<br>EIPPFSSSKKYQAVSVHSGDKSKSEIFVKGALNKVLERCSRYYNAE<br>GIATPLTDEIRRKSLQMADTLASSGLRILSFAYDKGNFEETGDGPS<br>DMIFCGLLGMNDPPRPSVSKSILKFMRGGVHIIMITGDSESTAVA<br>VAKQVGMVIDNSKYAVLSGDDIDAMSTEQLSQAISHCSVFARTT<br>PKHKVSIVRALQARGDIVAMTGDGVNDAPALKLADIGIAMGNM<br>GTDVAKEAADMVLTDDDFSTILSAIQEGKGIFYNIQNFLTFQLSTS<br>IAALSLIALSTAFNLPNPLNAMQILWINIIMDGPPAQSLGVEPVDK<br>AVMNKPPRKRNDKILTGKVIQRVVQSSFIIVCGTLYVYMHEIKDN<br>EVTARDTTMTFTCFVFFDMFNALTTRHHSKSIAELGWNNTMFNF<br>SVAASILGQLGAIYIPFLQSIFQTEPLSLKDLVHLLLLSSSVWIVDE<br>LRKLYVRRRDASPYNGYSMAV |
| 34 | Arabidopsis Thaliana AtECA1 (codon optimized for Pichia pastoris) | ATGGGAAAGGGTTCCGAGGACCTGGTTAAGAAAGAATCCCTG<br>AACTCCACTCCAGTTAACTCTGACACTTTCCCAGCTTGGGCTA<br>AGGATGTTGCTGAGTGCGAAGAGCACTTCGTTGTTTCCAGAGA<br>GAAGGGTTTGTCCTCCGACGAAGTCTTGAAGAGACACCAAAT<br>CTACGGACTGAACGAGTTGGAAAAGCCAGAGGGAACCTCCAT<br>CTTCAAGCTGATCTTGGAGCAGTTCAACGACACCCTTGTCAGA<br>ATTTTGTTGGCTGCCGCTGTTATTTCCTTCGTCCTGGCTTTTTT<br>GATGGTGACGAGGGTGGTGAAATGGGTATCACTGCCTTCGTT<br>GAGCCTTTGGTCATCTTCCTGATCTTGATCGTTAACGCCATCGT<br>TGGTATCTGGCAAGAGACTAACGCTGAAAAGGCTTTGGAGGC<br>CTTGAAAGAGATTCAATCCCAGCAGGCTACCGTTATGAGAGA<br>TGGTACTAAGGTTTCCTCCTTGCCAGCTAAAGAATTGGTTCCA<br>GGTGACATCGTTGAGCTGAGAGTTGGTGATAAGGTTCCAGCC<br>GACATGAGAGTTGTTGCTTTGATCTCCTCCACCTTGAGAGTTG<br>AACAAGGTTCCTGACTGGTGAATCTGAGGCTGTTTCCAAGAC<br>TACTAAGCACGTTGACGAGAACGCTGACATCCAGGGTAAAAA<br>GTGCATGGTTTTCGCCGGTACTACCGTTGTTAACGGTAACTGC<br>ATCGTGTTGGTCACTGACACTGGAATGAACACCGAGATCGGTA<br>GAGTTCACTCCCAAATCCAAGAAGCTGCTAACACGAAGAGG<br>ACACCCCATTGAAGAAGAAGCTGAACGAGTTCGGAGAGGTCT<br>TGACCATGATCATCGGATTGATCTGTGCCCTGGTCTGGTTGAT |

TABLE 9 -continued

BRIEF DESCRIPTION OF THE SEQUENCES

| SEQ ID NO: | Description | Sequence |
|---|---|---|
| | | CAACGTCAAGTACTTCTTGTCCTGGGAATACGTTGATGGATGG<br>CCAAGAAACTTCAAGTTCTCCTTCGAGAAGTGCACCTACTACT<br>TCGAGATCGCTGTTGCTTTGGCTGTTGCTGCTATTCCAGAGGG<br>ATTGCCAGCTGTTATCACCACTTGCTTGGCCTTGGGTACTAGA<br>AAGATGGCTCAGAAGAACGCCCTTGTTAGAAAGTTGCCATCC<br>GTTGAGACTTTGGGTTGTACTACCGTCATCTGTTCCGACAAGA<br>CTGGTACTTTGACTACCAACCAGATGGCCGTTTCCAAATTGGT<br>TGCCATGGGTTCCAGAATCGGTACTCTGAGATCCTTCAACGTC<br>GAGGGAACTTCTTTTGACCCAAGAGATGGAAAGATTGAGGAC<br>TGGCCAATGGGTAGAATGGACGCCAACTTGCAGATGATTGCT<br>AAGATCGCCGCTATCTGTAACGACGCTAACGTTGAGCAATCC<br>GACCAACAGTTCGTTTCCAGAGGAATGCCAACTGAGGCTGCC<br>TTGAAGGTTTTGGTCGAGAAGATGGGTTTCCCAGAAGGATTG<br>AACGAGGCTTCTTCCGATGGTGACGTCTTGAGATGTTGCAGAC<br>TGTGGAGTGAGTTGGAGCAGAGAATCGCTACTTTGGAGTTCG<br>ACAGAGATAGAAAGTCCATGGGTGTCATGGTTGATTCTTCCTC<br>CGGTAACAAGTTGTTGTTGGTCAAAGGAGCAGTTGAAAACGT<br>TTTGGAGAGATCCACCCACATTCAATTGCTGGACGGTTCCAAG<br>AGAGAATTGGACCAGTACTCCAGAGACTTGATCTTGCAGTCCT<br>TGAGAGACATGTCCTTGTCCGCCTTGAGATGTTTGGGTTTCGC<br>TTACTCTGACGTTCCATCCGATTTCGCTACTTACGATGGTTCTG<br>AGGATCATCCAGCTCACCAACAGTTGCTGAACCCATCCAACTA<br>CTCCTCCATCGAATCCAACCTGATCTTCGTTGGTTTCGTCGGTC<br>TTAGAGACCCACCAAGAAAAGAAGTTAGACAGGCCATCGCTG<br>ATTGTAGAACCGCCGGTATCAGAGTTATGGTCATCACCGGAG<br>ATAACAAGTCCACTGCCGAGGCTATTTGTAGAGAGATCGGAG<br>TTTTCGAGGCTGACGAGGACATTTCTTCCAGATCCCTGACCGG<br>TATTGAGTTCATGGACGTCCAAGACCAGAAGAACCACTTGAG<br>ACAGACCGGTGGTTTGTTGTTCTCCAGAGCCGAACCAAAGCA<br>CAAGCAAGAGATTGTCAGACTGCTGAAAGAGGACGGAGAAGT<br>TGTTGCTATGACCGGTGATGGTGTTAATGACGCCCCAGCTTTG<br>AAGTTGGCTGACATCGGTGTTGCTATGGGAATTTCCGGTACTG<br>AAGTTGCTAAGGAAGCCTCCGATATGGTTTTGGCTGACGACA<br>ACTTTTCAACTATCGTTGCTGCTGTCGGAGAAGGTAGAAGTAT<br>CTACAACAACATGAAAGCCTTTATCAGATACATGATTTCCTCC<br>AACATCGGTGAAGTTGCCTCCATTTTCTTGACTGCTGCCTTGG<br>GTATTCCTGAGGGAATGATCCCAGTTCAGTTGTTGTGGGTTAA<br>CTTGGTTACTGACGGTCCACCTGCTACTGCTTTGGGTTTCAAC<br>CCACCAGACAAAGACATTATGAAGAAGCCACCAAGAAGATCC<br>GACGATTCCTTGATCACCGCCTGGATCTTGTTCAGATACATGG<br>TCATCGGTCTTTATGTTGGTGTTGCCACCGTCGGTGTTTTCATC<br>ATCTGGTACACCCACTCTTCCTTCATGGGTATTGACTTGTCTCA<br>AGATGGTCATTCTTTGGTTTCCTACTCCCAATTGGCTCATTGGG<br>GACAATGTTCTTCCTGGGAGGGTTTCAAGGTTTCCCCATTCAC<br>TGCTGGTTCCCAGACTTTCTCCTTCGATTCCAACCCATGTGACT<br>ACTTCCAGCAGGGAAAGATCAAGGCTTCCACCTTGTCTTTGTC<br>CGTTTTTGGTCGCCATTGAGATGTTCAACTCCCTGAACGCTTTG<br>TCTGAGGACGGTTCCTTGGTTACTATGCCACCTTGGGTGAACC<br>CATGGTTGTTGTTGGCTATGGCTGTTTCCTTCGGATTGCACTTC<br>GTCATCCTGTACGTTCCATTCTTGGCCCAGGTTTTCGGTATTGT<br>TCCACTGTCCTTGAACGAGTGGTTGTTGGTCTTGGCCGTTTCTT<br>TGCCAGTTATCCTGATCGACGAGGTTTTGAAGTTCGTTGGTAG<br>ATGCACCTCTGGTTACAGATACTCCCCAAGAACTCTGTCCACC<br>AAGCAGAAAGAAGAGTAA |
| 35 | AtECA1 | MGKGSEDLVKKESLNSTPVNSDTFPAWAKDVAECEEHFVVSRE<br>KGLSSDEVLKRHQIYGLNELEKPEGTSIFKLILEQFNDTLVRILLA<br>AAVISFVLAFFDGDEGGEMGITAFVEPLVIFLILIVNAIVGIWQETN<br>AEKALEALKEIQSQQATVMRDGTKVSSLPAKELVPGDIVELRVG<br>DKVPADMRVVALISSTLRVEQGSLTGESEAVSKTTKHVDENADI<br>QGKKCMVFAGTTVVNGNCICLVTDTGMNTEIGRVHSQIQEAAQ<br>HEEDTPLKKKLNEFGEVLTMIIGLICALVWLINVKYFLSWEYVDG<br>WPRNFKFSFEKCTYYFEIAVALAVAAIPEGLPAVITTCLALGTRK<br>MAQKNALVRKLPSVETLGCTTVICSDKTGTLTTNQMAVSKLVA<br>MGSRIGTLRSFNVEGTSFDPRDGKIEDWPMGRMDANLQMIAKIA<br>AICNDANVEQSDQQFVSRGMPTEAALKVLVEKMGFPEGLNEASS<br>DGDVLRCCRLWSELEQRIATLEFDRDRKSMGVMVDSSSGNKLL<br>LVKGAVENVLERSTHIQLLDGSKRELDQYSRDLILQSLRDMSLSA<br>LRCLGFAYSDVPSDFATYDGSEDHPAHQQLLNPSNYSSIESNLIFV<br>GFVGLRDPPRKEVRQAIADCRTAGIRVMVITGDNKSTAEAICREI<br>GVFEADEDISSRSLTGIEFMDVQDQKNHLRQTGGLLFSRAEPKHK<br>QEIVRLLKEDGEVVAMTDGDVNDAPALKLADIGVAMGISGTEV<br>AKEASDMVLADDNFSTIVAAVGEGRSIYNNMKAFIRYMISSNIGE<br>VASIFLTAALGIPEGMIPVQLLWVNLVTDGPPATALGFNPPDKDI |

TABLE 9 -continued

BRIEF DESCRIPTION OF THE SEQUENCES

| SEQ ID NO: | Description | Sequence |
|---|---|---|
| | | MKKPPRRSDDSLITAWILFRYMVIGLYVGVATVGVFIIWYTHSSF MGIDLSQDGHSLVSYSQLAHWGQCSSWEGFKVSPFTAGSQTFSF DSNPCDYFQQGKIKASTLSLSVLVAIEMFNSLNALSEDGSLVTMP PWVNPWLLLAMAVSFGLHFVILYVPFLAQVFGIVPLSLNEWLLV LAVSLPVILIDEVLKFVGRCTSGYRYSPRTLSTKQKEE |
| 36 | PpPMR1/UP | GAATTCATGACAGCTAATGAAAATCCTTTTGAGAATGAG |
| 37 | PpPMR1/LP | GGCCGGCCTCAAACAGCCATGCTGTATCCATTGTATG |
| 38 | 5'AOX1 | GCGACTGGTTCCAATTGACAAGCTT |
| 39 | PpPMR1/cLP | GGTTGCTCTCGTCGATACTCAAGTGGGAAG |
| 40 | AtECA1/cLP | GTCGGCTGGAACCTTATCACCAACTCTCAG |
| 41 | Human calreticulin (hCRT) | ATGGAGATTTCCTTCAATTTTTACTGCTGTTTTATTCGCAGCATC CTCCGCATTAGCTTACCCATACGACGTCCCAGACTACGCTTAC CCATACGACGTCCCAGACTACGCTGAGCCCGCCGTCTACTTCA AGGAGCAGTTTCTGGACGGAGACGGGTGGACTTCCCGCTGGA TCGAATCCAAACACAAGTCAGATTTTGGCAAATTCGTTCTCAG TTCCGGCAAGTTCTACGGTGACGAGGAGAAAGATAAAGGTTT GCAGACAAGCCAGGATGCACGCTTTTATGCTCTGTCGGCCAGT TTCGAGCCTTTCAGCAACAAAGGCCAGACGCTGGTGGTGCAG TTCACGGTGAAACATGAGCAGAACATCGACTGTGGGGGCGGC TATGTGAAGCTGTTTCCTAATAGTTTGGACCAGACAGACATGC ACGGAGACTCAGAATACAACATCATGTTTGGTCCCGACATCTG TGGCCCTGGCACCAAGAAGGTTCATGTCATCTTCAACTACAAG GGCAAGAACGTGCTGATCAACAAGGACATCCGTTGCAAGGAT GATGAGTTTACACACCTGTACACACTGATTGTGCGGCCAGACA ACACCTATGAGGTGAAGATTGACAACAGCCAGGTGGAGTCCG GCTCCTTGGAAGACGATTGGGACTTCCTGCCACCCAAGAAGA TAAAGGATCCTGATGCTTCAAAACCGGAAGACTGGGATGAGC GGGCCAAGATCGATGATCCCACAGACTCCAAGCCTGAGGACT GGGACAAGCCCGAGCATATCCCTGACCCTGATGCTAAGAAGC CCGAGGACTGGGATGAAGAGATGGACGGAGAGTGGGAACCC CCAGTGATTCAGAACCCTGAGTACAAGGGTGAGTGGAAGCCC CGGCAGATCGACAACCCAGATTACAAGGGCACTTGGATCCAC CCAGAAATTGACAACCCCGAGTATTCTCCCGATCCCAGTATCT ATGCCTATGATAACTTTGGCGTGCTGGGCCTGGACCTCTGGCA GGTCAAGTCTGGCACCATCTTTGACAACTTCCTCATCACCAAC GATGAGGCATACGCTGAGGAGTTTGGCAACGAGACGTGGGGC GTAACAAAGGCAGCAGAGAAACAAATGAAGGACAAACAGGA CGAGGAGCAGAGGCTTAAGGAGGAGGAAGAAGACAAGAAAC GCAAAGAGGAGGAGGAGGCAGAGGACAAGGAGGATGATGAG GACAAAGATGAGGATGAGGAGGATGAGGAGGACAAGGAGGA AGATGAGGAGGAAGATGTCCCCGGCCAGGCCCATGACGAGCT GTAG |
| 42 | Human calreticulin (hCRT) | MRFPSIFTAVLFAASSALAYPYDVPDYAYPYDVPDYAEPAVYFK EQFLDGDGWTSRWIESKHKSDFGKFVLSSGKFYGDEEKDKGLQT SQDARFYALSASFEPFSNKGQTLVVQFTVKHEQNIDCGGGYVKL FPNSLDQTDMHGDSEYNIMFGPDICGPGTKKVHVIFNYKGKNVLI NKDIRCKDDEFTHLYTLIVRPDNTYEVKIDNSQVESGSLEDDWDF LPPKKIKDPDASKPEDWDERAKIDDPTDSKPEDWDKPEHIPDPDA KKPEDWDEEMDGEWEPPVIQNPEYKGEWKPRQIDNPDYKGTWI HPEIDNPEYSPDPSIYAYDNFGVLGLDLWQVKSGTIFDNFLITNDE AYAEEFGNETWGVTKAAEKQMKDKQDEEQRLKEEEEDKKRKE EEEAEDKEDDEDKDEDEEDEEDKEEDEEEDVPGQAHDEL |
| 43 | Human ERp57 | ATGCAATTCAACTGGAACATCAAGACTGTTGCTTCCATCTTGT CCGCTTTGACTTTGGCTCAAGCTTCTGACGTTTTGGAGTTGACT GACGACAACTTCGAGTCCAGAATTTCTGACACTGGTTCCGCTG GATTGATGTTGGTTGAGTTCTTCGCTCCATGGTGTGGTCATTGT AAGAGATTGGCTCCAGAATACGAAGCTGCTGCTACTAGATTG AAGGGTATCGTTCCATTGGCTAAGGTTGACTGTACTGCTAACA CTAACACTTGTAACAAGTACGGTGTTTCCGGTTACCCAACTTT GAAGATCTTCAGAGATGGTGAAGAAGCTGGAGCTTACGACGG TCCAAGAACTGCTGACGGTATCGTTTCCCACTTGAAGAAGCAA GCTGGTCCAGCTTCTGTTCCATTGAGAACTGAGGAGGAGTTCA AGAAGTTCATCTCCGACAAGGACGCTTCTATCGTTGGTTTCTT CGACGATTCTTTCTCTGAAGCTCACTCCGAATTCTTGAAGGCT |

TABLE 9 -continued

BRIEF DESCRIPTION OF THE SEQUENCES

| SEQ ID NO: | Description | Sequence |
|---|---|---|
| | | GCTTCCAACTTGAGAGACAACTACAGATTCGCTCACACTAACG TTGAGTCCTTGGTTAACGAGTACGACGATAACGGTGAAGGTA TCATCTTGTTCAGACCATCCCACTTGACTAACAAGTTCGAGGA CAAGACAGTTGCTTACACTGAGCAGAAGATGACTTCCGGAAA GATCAAGAAGTTTATCCAAGAGAACATCTTCGGTATCTGTCCA CACATGACTGAGGACAACAAGGACTTGATTCAGGGAAAGGAC TTGTTGATCGCTTACTACGACGTTGACTACGAGAAGAACGCTA AGGGTTCCAACTACTGGAGAAACAGAGTTATGATGGTTGCTA AGAAGTTCTTGGACGCTGGTCACAAGTTGAACTTCGCTGTTGC TTCTAGAAAGACTTTCTCCCACGAGTTGTCTGATTTCGGATTG GAATCCACTGCTGGAGAGATTCCAGTTGTTGCTATCAGAACTG CTAAGGGAGAGAAGTTCGTTATGCAAGAGGAGTTCTCCAGAG ATGGAAAGGCTTTGGAGAGATTCTTGCAGGATTACTTCGACG GTAACTTGAAGAGATACTTGAAGTCCGAGCCAATTCCAGAAT CTAACGACGGTCCAGTTAAAGTTGTTGTTGCTGAGAACTTCGA CGAGATCGTTAACAACGAGAACAAGGACGTTTTGATCGAGTT TTACGCTCCTTGGTGTGGACACTGTAAAAACTTGGAGCCAAAG TACAAGGAATTGGGTGAAAAGTTGTCCAAGGACCCAAACATC GTTATCGCTAAGATGGACGCTACTGCTAACGATGTTCCATCCC CATACGAAGTTAGAGGTTTCCCAACTATCTACTTCTCCCCAGC TAACAAGAAGTTGAACCCAAAGAAGTACGAGGGAGGTAGAG AATTGTCCGACTTCATCTCCTACTTGCAGAGAGAGGCTACTAA TCCACCAGTTATCCAAGAGGAGAAGCCAAAGAAGAAGAAGA AAGCTCACGACGAGTTGTAG |
| 44 | Human ERp57 | MQFNWNIKTVASILSALTLAQASDVLELTDDNFESRISDTGSAGL MLVEFFAPWCGHCKRLAPEYEAAATRLKGIVPLAKVDCTANTN TCNKYGVSGYPTLKIFRDGEEAGAYDGPRTADGIVSHLKKQAGP ASVPLRTEEEFKKFISDKDASIVGFFDDSFSEAHSEFLKAASNLRD NYRFAHTNVESLVNEYDDNGEGIILFRPSHLTNKFEDKTVAYTEQ KMTSGKIKKFIQENIFGICPHMTEDNKDLIQGKDLLIAYYDVDYE KNAKGSNYWRNRVMMVAKKFLDAGHKLNFAVASRKTFSHELS DFGLESTAGEIPVVAIRTAKGEKFVMQEEFSRDGKALERFLQDYF DGNLKRYLKSEPIPESNDGPVKVVVAENFDEIVNNENKDVLIEFY APWCGHCKNLEPKYKELGEKLSKDPNIVIAKMDATANDVPSPYE VRGFPTIYFSPANKKLNPKKYEGGRELSDFISYLQREATNPPVIQE EKPKKKKAHDEL |
| 45 | hCRT-BstZ17I-HA/UP | GTATACCCATACGACGTCCCAGACTACGCTGAGCCCGCCGTCT ACTTCAAGGAGC |
| 46 | hCRT-PacI/LP | TTAATTAACTACAGCTCGTCATGGGCCTGGCCGGGGACATCTT CC |
| 47 | Synthetic peptide that binds CRT | KLGFFKR |
| 48 | Alpha amylase signal peptide (from *Aspergillus niger* α-amylase) (DNA) | ATGGTTGCTT GGTGGTCCTT GTTCTTGTAC GGATTGCAAG TTGCTGCTCC AGCTTTGGCT |
| 49 | Alpha amylase signal peptide (from *Aspergillus niger* α-amylase) | MVAWWSLFLY GLQVAAPALA |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed is:

1. A method for producing a recombinant antibody having reduced O-glycosylation comprising:
   (a) providing a *Pichia pastoris* host comprising a deletion or disruption of a β-mannosyltransferase gene and at least one phosphomannosyl transferase gene and a nucleic acid molecule encoding at least one endogenous or exogenous $Ca^{2+}$ ATPase wherein expression of the $Ca^{2+}$ ATPase in the host cell is ectopic;
   (b) introducing a nucleic acid molecule into the host cell encoding the recombinant antibody: and
   (c) growing the host cell under conditions suitable for producing the recombinant antibody.

2. The method of claim 1, wherein the nucleic acid molecule comprises an open reading frame encoding the $Ca^{2+}$ ATPase operably linked to a heterologous promoter.

3. The method of claim 1, wherein the function of at least one endogenous gene encoding a chaperone protein has been reduced, disrupted, or deleted; and a nucleic acid molecule encoding at least one mammalian homolog of the chaperone protein is expressed in the host cell.

4. The method of claim 1, wherein the host cell further includes a nucleic acid molecule encoding an Erp57 protein and/or a nucleic acid molecule encoding a calreticulin protein.

5. The method of claim 1, wherein the host cell is engineered to reduce or eliminate the function of at least one endogenous *Pichia pastoris* gene encoding a protein O-mannosyltransferase (PMT) protein.

6. The method of claim 5, wherein the PMT protein is selected from the group consisting of PMT1 and PMT4.

7. The method of claim 3, wherein the wherein heterologous chaperone protein is human PDI.

* * * * *